United States Patent
Xia

(10) Patent No.: US 11,839,147 B2
(45) Date of Patent: Dec. 5, 2023

(54) HOLE INJECTION LAYER AND CHARGE GENERATION LAYER CONTAINING A TRUXENE BASED COMPOUND

(71) Applicant: BEIJING SUMMER SPROUT TECHNOLOGY CO., LTD., Beijing (CN)

(72) Inventor: Chuanjun Xia, Lawrenceville, NJ (US)

(73) Assignee: BEIJING SUMMER SPROUT TECHNOLOGY CO., LTD., Beijing (CN)

( * ) Notice: Subject to any disclaimer, the term of this patent is extended or adjusted under 35 U.S.C. 154(b) by 778 days.

(21) Appl. No.: 16/101,565

(22) Filed: Aug. 13, 2018

(65) Prior Publication Data

US 2019/0074446 A1 Mar. 7, 2019

Related U.S. Application Data

(60) Provisional application No. 62/553,919, filed on Sep. 4, 2017.

(51) Int. Cl.
*C07C 211/54* (2006.01)
*C07C 211/58* (2006.01)
(Continued)

(52) U.S. Cl.
CPC ......... *H10K 85/624* (2023.02); *C07C 255/34* (2013.01); *C07C 255/37* (2013.01);
(Continued)

(58) Field of Classification Search
CPC ............. H01L 51/5088; H01L 51/0056; H01L 51/0051; H01L 51/0072; H01L 51/0052; H01L 51/0067; H01L 51/5012; H01L 51/5056; H01L 51/5092; H01L 51/0071; H01L 51/006; H01L 51/0061; H01L 51/504; H01L 51/0059; H01L 51/0058; H01L 51/0068; H01L 51/0073; H01L 51/0074; C07C 381/00; C07C 255/37; C07C 255/51; C07C 255/34; C07C 2603/54; C07C 211/54; C07C 211/58;
(Continued)

(56) References Cited

U.S. PATENT DOCUMENTS

| 5,703,436 A | 12/1997 | Forrest et al. |
| 5,707,745 A | 1/1998 | Forrest et al. |

(Continued)

OTHER PUBLICATIONS

Tang, C. W. et al., "Organic electroluminescent diodes", Applied Physics Letters, 51(12): 913-915 (1987).

(Continued)

*Primary Examiner* — Sean M DeGuire
*Assistant Examiner* — Rachel Simbana
(74) *Attorney, Agent, or Firm* — Workman Nydegger

(57) ABSTRACT

Hole injection layer and charge generation layer containing a truxene based compound are disclosed for organic electronic devices. By applying the truxene based compound for the hole injection layer, low driving voltage, high efficiency and long lifetime of the device can be achieved. In addition, a P-type charge generation layer comprising the truxene based compound can be used in tandem OLEDs structure and can further improve the voltage, efficiency and lifetime of the device.

12 Claims, 4 Drawing Sheets

Figure 1:
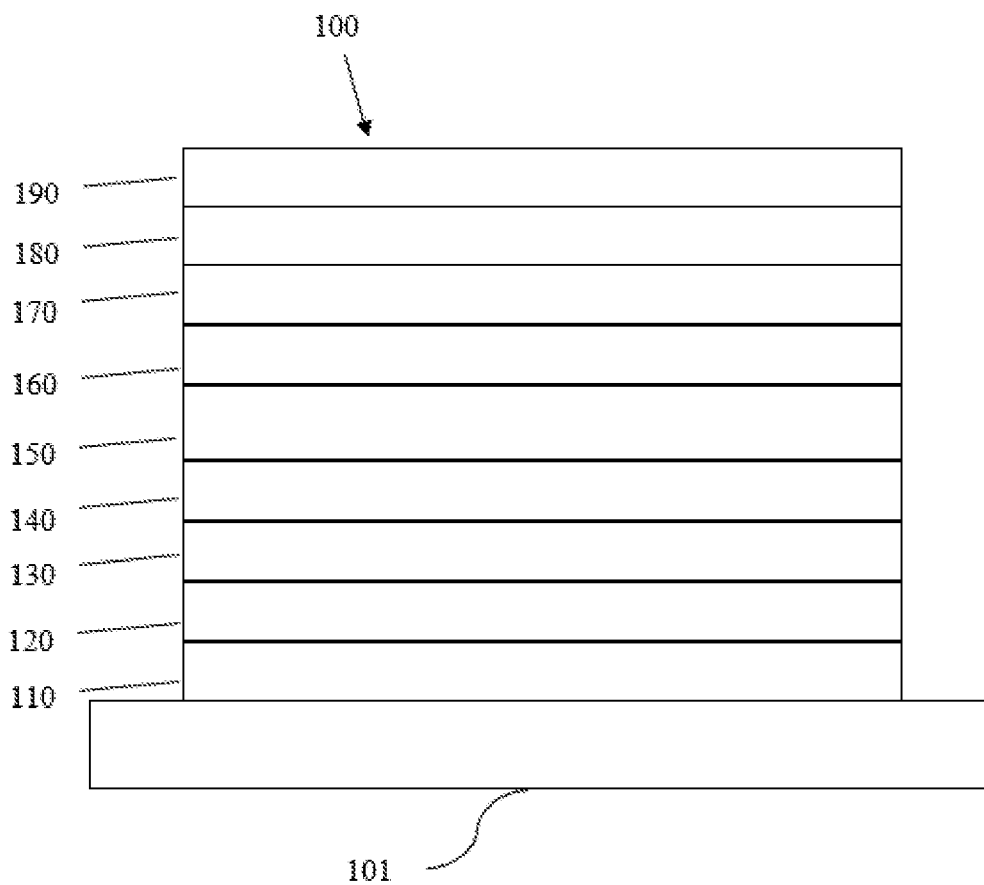

(51) Int. Cl.

| | | |
|---|---|---|
| *C07C 211/61* | (2006.01) | |
| *C07C 255/31* | (2006.01) | |
| *C07C 255/34* | (2006.01) | |
| *C07C 255/37* | (2006.01) | |
| *C07C 255/51* | (2006.01) | |
| *C07C 321/26* | (2006.01) | |
| *C07C 381/00* | (2006.01) | |
| *C07D 209/86* | (2006.01) | |
| *C07D 209/88* | (2006.01) | |
| *C07D 307/52* | (2006.01) | |
| *C07D 307/91* | (2006.01) | |
| *C07D 333/20* | (2006.01) | |
| *C07D 333/76* | (2006.01) | |
| *C07D 405/12* | (2006.01) | |
| *C07D 409/12* | (2006.01) | |
| *C07D 409/14* | (2006.01) | |
| *C07D 471/14* | (2006.01) | |
| *C07D 487/04* | (2006.01) | |
| *C07D 487/06* | (2006.01) | |
| *C07D 487/14* | (2006.01) | |
| *C09K 11/06* | (2006.01) | |
| *H10K 50/11* | (2023.01) | |
| *H10K 50/13* | (2023.01) | |
| *H10K 50/15* | (2023.01) | |
| *H10K 50/17* | (2023.01) | |
| *H10K 85/60* | (2023.01) | |

(52) U.S. Cl.
CPC .......... *C07C 255/51* (2013.01); *C07C 381/00* (2013.01); *H10K 50/13* (2023.02); *H10K 85/611* (2023.02); *H10K 85/633* (2023.02); *H10K 85/636* (2023.02); *H10K 85/6572* (2023.02); *C07C 2603/54* (2017.05); *H10K 50/17* (2023.02); *H10K 85/631* (2023.02)

(58) Field of Classification Search
CPC ... C07C 211/61; C07C 255/31; C07C 321/26; C07D 209/86; C07D 209/88; C07D 307/52; C07D 307/91; C07D 333/20; C07D 333/76; C07D 405/12; C07D 409/12; C07D 409/14; C07D 471/14; C07D 487/04; C07D 487/06; C07D 487/14; C09K 11/06; C09K 2211/1029; C09K 2211/1007; C09K 2211/1014; C09K 2211/1011; C09K 2211/1044; C09K 2211/1088; C09K 2211/1092; H10K 85/615; H10K 85/624; H10K 85/626

See application file for complete search history.

(56) References Cited

U.S. PATENT DOCUMENTS

| | | | |
|---|---|---|---|
| 5,844,363 A | 12/1998 | Gu et al. | |
| 6,097,147 A | 8/2000 | Baldo et al. | |
| 6,303,238 B1 | 10/2001 | Thompson et al. | |
| 7,279,704 B2 | 10/2007 | Walters et al. | |
| 7,968,146 B2 | 6/2011 | Wagner et al. | |
| 2003/0008174 A1* | 1/2003 | Suzuki ................ | C09K 11/06 428/690 |
| 2003/0230980 A1 | 12/2003 | Forrest et al. | |
| 2004/0174116 A1 | 9/2004 | Lu et al. | |
| 2008/0087879 A1* | 4/2008 | Ionkin .................... | C07C 17/25 313/506 |
| 2008/0093980 A1* | 4/2008 | Stoessel ................ | C07C 13/72 313/504 |
| 2010/0288362 A1* | 11/2010 | Hatwar ............... | H01L 51/5278 136/263 |
| 2014/0144509 A1 | 5/2014 | Fadhel et al. | |
| 2015/0155513 A1* | 6/2015 | Pieh .................... | H01L 27/3209 257/40 |
| 2015/0349273 A1 | 12/2015 | Hung et al. | |
| 2016/0359122 A1 | 12/2016 | Boudreault et al. | |
| 2017/0054080 A1* | 2/2017 | Sato ................... | H01L 51/0072 |

OTHER PUBLICATIONS

Christian B. Nielsen et al., "Efficient truxenone-based acceptors for organic photovoltaics", Journal of Materials Chemistry A, 1(1), 73-76. (2013).

Kyosuke Isoda et al., "Truxene-Based Columnar Liquid Crystals: Self-Assembled Structures and Electro-Active Properties", Chemistry an Asian Journal, 2009, 4, 1619-1625.

Lionel Sanguinet et al., "Synthesis and Characterization of New Truxenones for Nonlinear Optical Applications", Chemistry of Materials. 2006, 18, 4259-4269.

Kochurani Jacob et al., "Synthesis of Novel Truxenequinone Based Electron Acceptors", Tetrahedron Letters, 40 (1999), 8625-8628.

* cited by examiner

HOLE INJECTION LAYER AND CHARGE GENERATION LAYER CONTAINING A TRUXENE BASED COMPOUND

This application claims the benefit of U.S. Provisional Application No. 62/553,919, filed Sep. 4, 2017, the entire content of which is incorporated herein by reference.

1 FIELD OF THE INVENTION

The present invention relates to a hole injection layer and a charge generation layer for organic electronic devices, such as organic light emitting devices. More specifically, the present invention relates to a hole injection layer and a charge generation layer which contain a truxene based compound.

2 BACKGROUND ART

An organic electronic device is preferably selected from the group consisting of organic light-emitting diodes (OLEDs), organic field-effect transistors (O-FETs), organic light-emitting transistors (OLETs), organic photovoltaic devices (OPVs), dye-sensitized solar cells (DSSCs), organic optical detectors, organic photoreceptors, organic field-quench devices (OFQDs), light-emitting electrochemical cells (LECs), organic laser diodes and organic plasmon emitting devices.

In 1987, Tang and Van Slyke of Eastman Kodak reported a bilayer organic electroluminescent device, which comprises an arylamine hole transporting layer and a tris-8-hydroxyquinolato-aluminum layer as the electron and emitting layer (Applied Physics Letters, 1987, 51 (12):913-915). Once a bias is applied to the device, green light was emitted from the device. This invention laid the foundation for the development of modern organic light-emitting diodes (OLEDs). State-of-the-art OLEDs may comprise multiple layers such as charge injection and transporting layers, charge and exciton blocking layers, and one or multiple emissive layers between the cathode and anode. Since OLED is a self-emitting solid state device, it offers tremendous potential for display and lighting applications. In addition, the inherent properties of organic materials, such as their flexibility, may make them well suited for particular applications such as fabrication on flexible substrates.

OLED can be categorized as three different types according to its emitting mechanism. The OLED invented by Tang and van Slyke is a fluorescent OLED. It only utilizes singlet emission. The triplets generated in the device are wasted through nonradiative decay channels. Therefore, the internal quantum efficiency (IQE) of a fluorescent OLED is only 25%. This limitation hindered the commercialization of OLED. In 1997, Forrest and Thompson reported phosphorescent OLED, which uses triplet emission from heave metal containing complexes as the emitter. As a result, both singlet and triplets can be harvested, achieving 100% IQE. The discovery and development of phosphorescent OLED contributed directly to the commercialization of active-matrix OLED (AMOLED) due to its high efficiency. Recently, Adachi achieved high efficiency through thermally activated delayed fluorescence (TADF) of organic compounds. These emitters have small singlet-triplet gap that makes the transition from triplet back to singlet possible. In the TADF device, the triplet excitons can go through reverse intersystem crossing to generate singlet excitons, resulting in high IQE.

OLEDs can also be classified as small molecule and polymer OLEDs according to the forms of the materials used. Small molecule refers to any organic or organometallic material that is not a polymer. The molecular weight of a small molecule can be large as long as it has well defined structure. Dendrimers with well-defined structures are considered as small molecules. Polymer OLEDs include conjugated polymers and non-conjugated polymers with pendant emitting groups. Small molecule OLED can become a polymer OLED if post polymerization occurred during the fabrication process.

There are various methods for OLED fabrication. Small molecule OLEDs are generally fabricated by vacuum thermal evaporation. Polymer OLEDs are fabricated by solution process, such as spin-coating, ink-jet printing, and nozzle printing. Small molecule OLEDs can also be fabricated by solution process if the materials can be dissolved or dispersed in solvents.

The emitting color of an OLED can be achieved by emitter structural design. An OLED may comprise one emitting layer or a plurality of emitting layers to achieve desired spectrum. In the case of green, yellow, and red OLEDs, phosphorescent emitters have successfully reached commercialization. Blue phosphorescent emitters still suffer from non-saturated blue color, short device lifetime, and high operating voltage. Commercial full-color OLED displays normally adopt a hybrid strategy, using fluorescent blue and phosphorescent yellow, or red and green. At present, efficiency roll-off of phosphorescent OLEDs at high brightness remains a problem. In addition, it is desirable to have more saturated emitting color, higher efficiency, and longer device lifetime. For fluorescent blue OLEDs, the color saturation, device efficiency, and device lifetime need to be improved to reduce power consumption. In the meantime, TADF devices haven't reached the lifetime goal for commercialization. TADF emitters also need to improve their color purity, severe efficiency roll-off, and device lifetime.

In an OLED device, hole injection layer (HIL) facilitates hole injection from the ITO anode to the organic layers. To achieve low device driving voltage, it is critical to have minimum charge injection barrier from the anode. Various HIL materials has been developed such as triarylamine compounds with shallow HOMO energy levels, very electron deficient heterocycles, and triarylamine amine compounds doped with p-type conductivity dopants. To improve OLED performance such as longer device lifetime, higher efficiency, and lower voltage, it is crucial to develop more robust HIL materials.

3 SUMMARY OF THE INVENTION

The present invention aims to improve the voltage, efficiency and lifetime of OLEDs by using a hole injection layer comprising a truxene based compound. In addition, a charge generation layer comprising a truxene based compound is provided, which can be used for the P-type charge generation layer in tandem OLEDs structure to further improve the voltage, efficiency and lifetime of the OLEDs.

According to an embodiment of the present invention, an organic electroluminescent device is disclosed, which comprises:
  an anode,
  a cathode,
  a hole injection layer disposed between the anode and cathode, wherein the hole injection layer comprises a compound represented by formula 1:

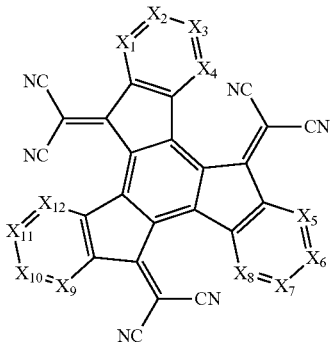

Formula 1

Wherein

X₁ to X₁₂ are independently selected from CR or N;

R is selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, nitrile, isonitrile, sulfanyl, sulfinyl, sulfonyl, phosphino, and combinations thereof;

R can be the same or different when there are multiple R groups present;

Any adjacent R groups are optionally joined to form a ring or a fused structure.

According to another embodiment, a tandem organic electroluminescent device is disclosed, which comprising:

an anode, a cathode, a charge generation layer disposed between the anode and cathode, wherein the charge generation layer comprises a compound represented by formula 1:

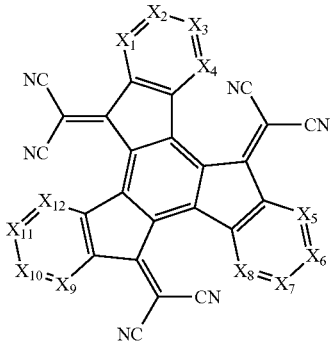

Formula 1

Wherein

X₁ to X₁₂ are independently selected from CR or N;

R is selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, nitrile, isonitrile, sulfanyl, sulfinyl, sulfonyl, phosphino, and combinations thereof;

R can be the same or different when there are multiple R groups present;

Any adjacent R groups are optionally joined to form a ring or a fused structure.

According to another embodiment of the present invention, a compound having any structure of Compound 4 to Compound 11 is disclosed.

The hole injection layer and the charge generation layer disclosed in the present invention comprise a truxene based compound, which can reduce the voltage of the OLED device and improve the efficiency and lifetime of the device.

4 BRIEF DESCRIPTION OF THE DRAWINGS

FIG. 1 schematically shows an organic light emitting device that can incorporate the compound material disclosed herein.

Figure 2:
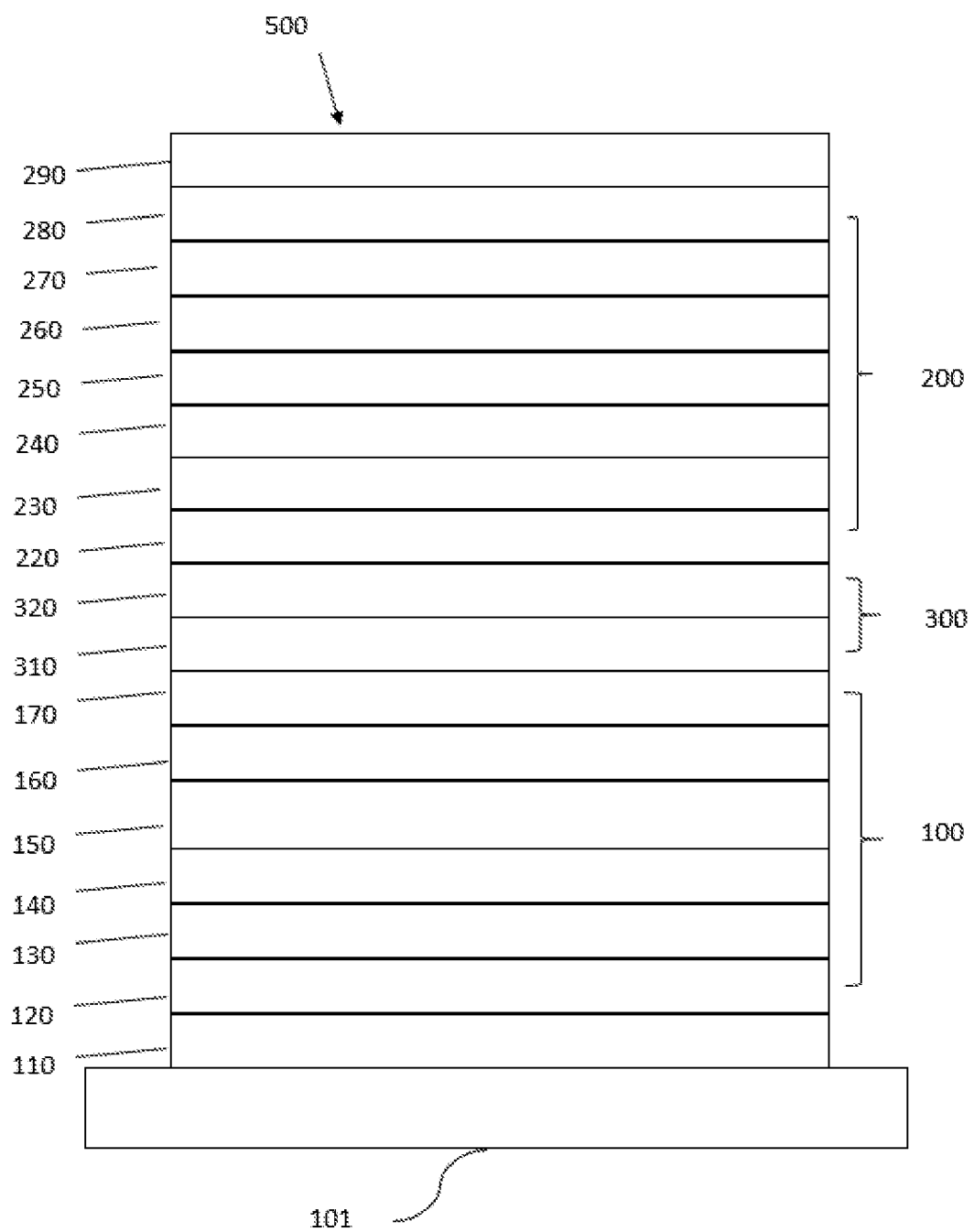

FIG. 2 schematically shows a tandem organic electroluminescent device that can incorporate the compound material disclosed herein.

Figure 3:
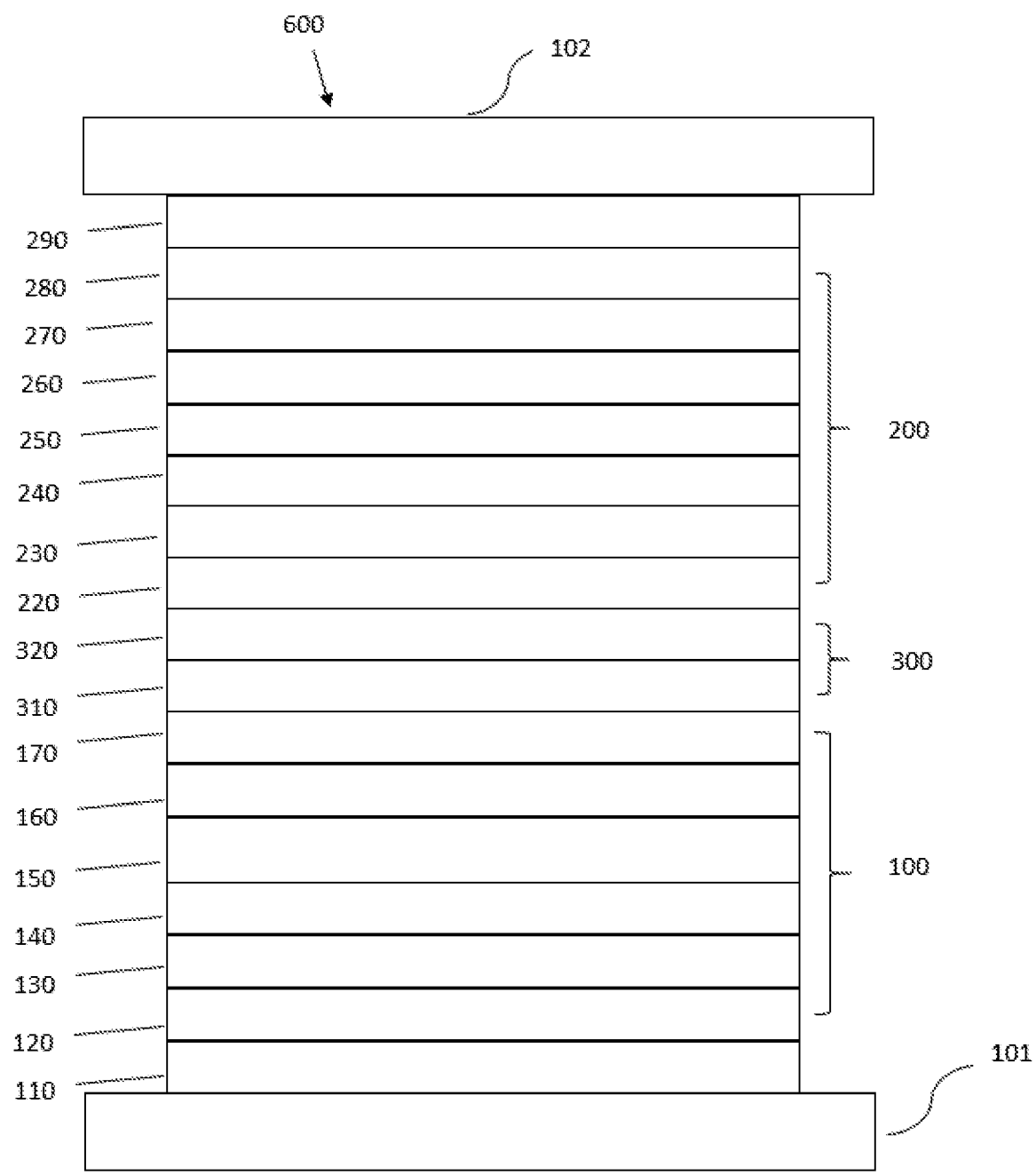

FIG. 3 schematically shows another tandem organic electroluminescent device that can incorporate the compound material disclosed herein.

Figure 4:
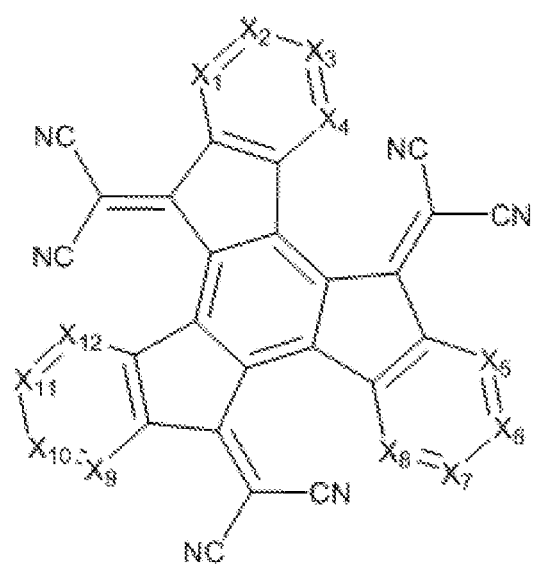

FIG. 4 shows the compound of Formula 1 disclosed herein.

5 DETAILED DESCRIPTION

OLEDs can be fabricated on various types of substrates such as glass, plastic, and metal foil. FIG. 1 schematically shows the organic light emitting device 100 without limitation. The figures are not necessarily drawn to scale. Some of the layer in the figure can also be omitted as needed. Device 100 may include a substrate 101, an anode 110, a hole injection layer 120, a hole transport layer 130, an electron blocking layer 140, an emissive layer 150, a hole blocking layer 160, an electron transport layer 170, an electron injection layer 180 and a cathode 190. Device 100 may be fabricated by depositing the layers described in order. The properties and functions of these various layers, as well as example materials, are described in more detail in U.S. Pat. No. 7,279,704 at cols. 6-10, which are incorporated by reference in its entirety.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F4-TCNQ at a molar ratio of 50:1, as disclosed in U.S. Patent Application Publication No. 2003/0230980, which is incorporated by reference in its entirety. Examples of host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

The layered structure described above is provided by way of non-limiting example. Functional OLEDs may be achieved by combining the various layers described in different ways, or layers may be omitted entirely. It may also include other layers not specifically described. Within each layer, a single material or a mixture of multiple materials can be used to achieve optimum performance. Any functional layer may include several sublayers. For example, the emissive layer may have a two layers of different emitting materials to achieve desired emission spectrum.

In one embodiment, an OLED may be described as having an "organic layer" disposed between a cathode and an anode. This organic layer may comprise a single layer or multiple layers.

In one embodiment, two or more OLED units may be series connection to form a tandem OLED, FIG. 2 schematically shows the tandem organic light emitting device 500 without limitation. The device 500 may include a substrate 101, an anode 110, a first unit 100, a charge generation layer 300, a second unit 200, and a cathode 290. Wherein the first unit 100 includes a hole injection layer 120, a hole transport layer 130, an electron blocking layer 140, an emissive layer 150, a hole blocking layer 160, an electron transport layer 170, and the second unit 200 includes a hole injection layer 220, a hole transport layer 230, an electron blocking layer 240, an emissive layer 250, a hole blocking layer 260, an electron transport layer 270, and an electron injection layer 280. The charge generation layers 300 include a N type charge generation layer 310 and a P type charge generation layer 320. The device 500 may be manufactured by sequentially depositing the described layers.

An OLED can be encapsulated by a barrier layer to protect it from harmful species from the environment such as moisture and oxygen. FIG. 3 schematically shows the organic light emitting device 600 without limitation. FIG. 3 differs from FIG. 2 in that the organic light emitting device 600 include a barrier layer 102, which is above the cathode 290. Any material that can provide the barrier function can be used as the barrier layer such as glass and organic-inorganic hybrid layers. The barrier layer should be placed directly or indirectly outside of the OLED device. Multi-layer thin film encapsulation was described in U.S. Pat. No. 7,968,146, which is herein incorporated by reference in its entirety.

Devices fabricated in accordance with embodiments of the invention can be incorporated into a wide variety of consumer products that have one or more of the electronic component modules (or units) incorporated therein. Some examples of such consumer products include flat panel displays, monitors, medical monitors, televisions, billboards, lights for interior or exterior illumination and/or signaling, heads-up displays, fully or partially transparent displays, flexible displays, smart phones, tablets, phablets, wearable devices, smart watches, laptop computers, digital cameras, camcorders, viewfinders, micro-displays, 3-D displays, vehicles displays, and vehicle tail lights.

The materials and structures described herein may be used in other organic electronic devices listed above.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

It is believed that the internal quantum efficiency (IQE) of fluorescent OLEDs can exceed the 25% spin statistics limit through delayed fluorescence. As used herein, there are two types of delayed fluorescence, i.e. P-type delayed fluorescence and E-type delayed fluorescence. P-type delayed fluorescence is generated from triplet-triplet annihilation (TTA).

On the other hand, E-type delayed fluorescence does not rely on the collision of two triplets, but rather on the transition between the triplet states and the singlet excited states. Compounds that are capable of generating E-type delayed fluorescence are required to have very small singlet-triplet gaps to convert between energy states. Thermal energy can activate the transition from the triplet state back to the singlet state. This type of delayed fluorescence is also known as thermally activated delayed fluorescence (TADF). A distinctive feature of TADF is that the delayed component increases as temperature rises. If the reverse intersystem crossing rate is fast enough to minimize the non-radiative decay from the triplet state, the fraction of back populated singlet excited states can potentially reach 75%. The total singlet fraction can be 100%, far exceeding 25% of the spin statistics limit for electrically generated excitons.

E-type delayed fluorescence characteristics can be found in an exciplex system or in a single compound. Without being bound by theory, it is believed that E-type delayed fluorescence requires the luminescent material to have a small singlet-triplet energy gap ($\Delta E_{S-T}$). Organic, non-metal containing, donor-acceptor luminescent materials may be able to achieve this. The emission in these materials is often characterized as a donor-acceptor charge-transfer (CT) type emission. The spatial separation of the HOMO and LUMO in these donor-acceptor type compounds often results in small ΔES-T. These states may involve CT states. Often, donor-acceptor luminescent materials are constructed by connecting an electron donor moiety such as amino- or carbazole-derivatives and an electron acceptor moiety such as N-containing six-membered aromatic rings.

Definition of Terms of Substituents halogen or halide—as used herein includes fluorine, chlorine, bromine, and iodine.

Alkyl—contemplates both straight and branched chain alkyl groups. Examples of the alkyl group include methyl group, ethyl group, propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, 1-methylpentyl group, 2-methylpentyl group, 1-pentylhexyl group, 1-butylpentyl group, 1-heptyloctyl group, 3-methylpentyl group. Additionally, the alkyl group may be optionally substituted. The carbons in the alkyl chain can be replaced by other hetero atoms. Of the above, preferred are methyl group, ethyl group, propyl group, isopropyl group, n-butyl group, s-butyl group, isobutyl group, t-butyl group, n-pentyl group, and neopentyl group.

Cycloalkyl—as used herein contemplates cyclic alkyl groups. Preferred cycloalkyl groups are those containing 4 to 10 ring carbon atoms and includes cyclobutyl, cyclopentyl, cyclohexyl, 4-methylcyclohexyl, 4,4-dimethylcylcohexyl, 1-adamantyl, 2-adamantyl, 1-norbornyl, 2-norbornyl and the like. Additionally, the cycloalkyl group may be optionally substituted. The carbons in the ring can be replaced by other hetero atoms.

Alkenyl—as used herein contemplates both straight and branched chain alkene groups. Preferred alkenyl groups are those containing two to fifteen carbon atoms. Examples of the alkenyl group include vinyl group, allyl group, 1-butenyl group, 2-butenyl group, 3-butenyl group, 1,3-butandienyl group, 1-methylvinyl group, styryl group, 2,2-diphenylvinyl group, 1,2-diphenylvinyl group, 1-methylallyl group, 1,1-dimethylallyl group, 2-methylallyl group, 1-phenylallyl group, 2-phenylallyl group, 3-phenylallyl group, 3,3-diphenylallyl group, 1,2-dimethylallyl group, 1-phenyl 1-butenyl group, and 3-phenyl-1-butenyl group. Additionally, the alkenyl group may be optionally substituted.

Alkynyl—as used herein contemplates both straight and branched chain alkyne groups. Preferred alkynyl groups are those containing two to fifteen carbon atoms. Additionally, the alkynyl group may be optionally substituted.

Aryl or aromatic group—as used herein contemplates noncondensed and condensed systems. Preferred aryl groups are those containing six to sixty carbon atoms, preferably six to twenty carbon atoms, more preferably six to twelve carbon atoms. Examples of the aryl group include phenyl, biphenyl, terphenyl, triphenylene, tetraphenylene, naphthalene, anthracene, phenalene, phenanthrene, fluorene, pyrene, chrysene, perylene, and azulene, preferably phenyl, biphenyl, terphenyl, triphenylene, fluorene, and naphthalene. Additionally, the aryl group may be optionally substituted. Examples of the non-condensed aryl group include phenyl group, biphenyl-2-yl group, biphenyl-3-yl group, biphenyl-4-yl group, p-terphenyl-4-yl group, p-terphenyl-3-yl group, p-terphenyl-2-yl group, m-terphenyl-4-yl group, m-terphenyl-3-yl group, m-terphenyl-2-yl group, o-tolyl group, m-tolyl group, p-tolyl group, p-t-butylphenyl group, p-(2-phenylpropyl)phenyl group, 4'-methylbiphenylyl group, 4"-t-butyl p-terphenyl-4-yl group, o-cumenyl group, m-cumenyl group, p-cumenyl group, 2,3-xylyl group, 3,4-xylyl group, 2,5-xylyl group, mesityl group, and m-quarterphenyl group.

Heterocyclic group or heterocycle—as used herein contemplates aromatic and non-aromatic cyclic groups. Heteroaromatic also means heteroaryl. Preferred non-aromatic heterocyclic groups are those containing 3 to 7 ring atoms which includes at least one hetero atom such as nitrogen, oxygen, and sulfur. The heterocyclic group can also be an aromatic heterocyclic group having at least one heteroatom selected from nitrogen atom, oxygen atom, sulfur atom, and selenium atom.

Heteroaryl—as used herein contemplates noncondensed and condensed hetero-aromatic groups that may include from one to five heteroatoms. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Alkoxy—it is represented by —O-Alkyl. Examples and preferred examples thereof are the same as those described above. Examples of the alkoxy group having 1 to 20 carbon atoms, preferably 1 to 6 carbon atoms include methoxy group, ethoxy group, propoxy group, butoxy group, pentyloxy group, and hexyloxy group. The alkoxy group having 3 or more carbon atoms may be linear, cyclic or branched.

Aryloxy—it is represented by —O-Aryl or —O-heteroaryl. Examples and preferred examples thereof are the same as those described above. Examples of the aryloxy group having 6 to 40 carbon atoms include phenoxy group and biphenyloxy group.

Arylalkyl—as used herein contemplates an alkyl group that has an aryl substituent. Additionally, the arylalkyl group may be optionally substituted. Examples of the arylalkyl group include benzyl group, 1-phenylethyl group, 2-phenylethyl group, 1-phenylisopropyl group, 2-phenylisopropyl group, phenyl-t-butyl group, alpha.-naphthylmethyl group, 1-alpha.-naphthylethyl group, 2-alpha-naphthylethyl group, 1-alpha-naphthylisopropyl group, 2-alpha-naphthylisopropyl group, beta-naphthylmethyl group, 1-beta-naphthylethyl group, 2-beta-naphthylethyl group, 1-beta-naphthylisopropyl group, 2-beta-naphthylisopropyl group, p-methylbenzyl group, m-methylbenzyl group, o-methylbenzyl group, p-chlorobenzyl group, m-chlorobenzyl group, o-chlorobenzyl group, p-bromobenzyl group, m-bromobenzyl group, o-bromobenzyl group, p-iodobenzyl group, m-iodobenzyl group, o-iodobenzyl group, p-hydroxybenzyl group, m-hydroxybenzyl group, o-hydroxybenzyl group, p-aminobenzyl group, m-aminobenzyl group, o-aminobenzyl group, p-nitrobenzyl group, m-nitrobenzyl group, o-nitrobenzyl group, p-cyanobenzyl group, m-cyanobenzyl group, o-cyanobenzyl group, 1-hydroxy-2-phenylisopropyl group, and 1-chloro2-phenylisopropyl group. Of the above, preferred are benzyl group, p-cyanobenzyl group, m-cyanobenzyl group, o-cyanobenzyl group, 1-phenylethyl group, 2-phenylethyl group, 1-phenylisopropyl group, and 2-phenylisopropyl group.

The term "aza" in azadibenzofuran, aza-dibenzothiophene, etc. means that one or more of the C—H groups in the respective aromatic fragment are replaced by a nitrogen atom. For example, azatriphenylene encompasses dibenzo[f,h]quinoxaline,dibenzo[f,h]quinoline and other analogues with two or more nitrogens in the ring system. One of ordinary skill in the art can readily envision other nitrogen analogs of the aza-derivatives described above, and all such analogs are intended to be encompassed by the terms as set forth herein.

The alkyl, cycloalkyl, alkenyl, alkynyl, aralkyl, heterocyclic group, aryl, and heteroaryl may be unsubstituted or may be substituted with one or more substituents selected from the group consisting of deuterium, halogen, alkyl, cycloalkyl, arylalkyl, alkoxy, aryloxy, amino, cyclic amino, silyl, alkenyl, cycloalkenyl, heteroalkenyl, alkynyl, aryl, heteroaryl, an acyl group, a carbonyl group, a carboxylic acid group, an ether group, an ester group, a nitrile group, an isonitrile group, a sulfanyl group, a sulfinyl group, a sulfonyl group, a phosphino group, and combinations thereof.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In the compounds mentioned in this disclosure, the hydrogen atoms can be partially or fully replaced by deuterium. Other atoms such as carbon and nitrogen, can also be replaced by their other stable isotopes. The replacement by other stable isotopes in the compounds may be preferred due to its enhancements of device efficiency and stability.

In the compounds mentioned in this disclosure, multiple substitutions refer to a range that includes a double substitution, up to the maximum available substitutions.

In the compounds mentioned in this disclosure, the expression that adjacent substituents are optionally joined to form a ring is intended to be taken to mean that two radicals are linked to each other by a chemical bond. This is illustrated by the following scheme:

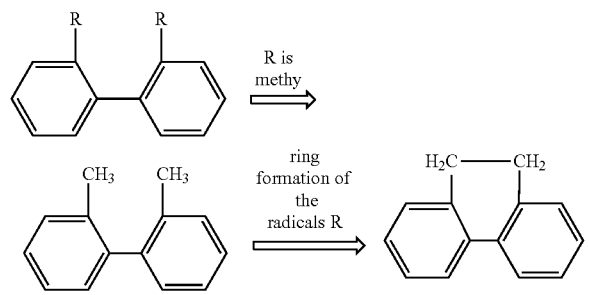

Futhermore, the expression that adjacent substituents are optionally joined to form a ring is also intended to be taken to mean that in the case where one of the two radicals represents hydrogen, the second radical is bonded at a position to which the hydrogen atom was bonded, with formation of a ring. This is illustrated by the following scheme:

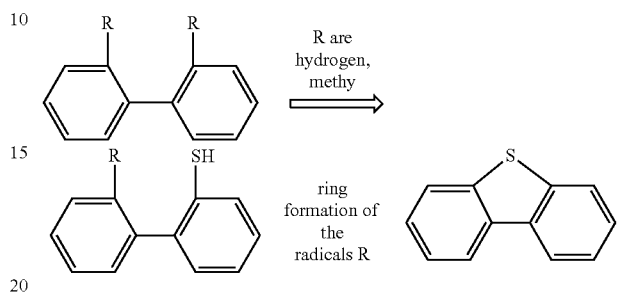

According to an embodiment of the present invention, an organic electroluminescent device is disclosed. The organic electroluminescent device comprises: an anode, a cathode, a hole injection layer disposed between the anode and cathode, wherein the hole injection layer comprises a compound represented by formula 1:

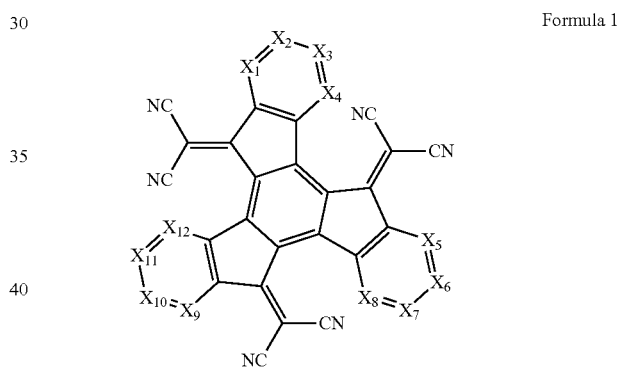

Formula 1

Wherein $X_1$ to $X_{12}$ are independently selected from CR or N;

R is selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, nitrile, isonitrile, sulfanyl, sulfinyl, sulfonyl, phosphino, and combinations thereof;

R can be the same or different when there are multiple R groups present;

Any adjacent R groups are optionally joined to form a ring or a fused structure.

In one embodiment, wherein the hole injection layer comprising the compound of formula 1 is in contact with the anode.

In one embodiment, wherein R is selected from the group consisting of nitro, fluorine, cyano, trifluoromethyl, trifluoromethoxy, and pentafluorosulfide.

In one preferred embodiment, wherein the compound having formula 1 is selected from the group consisting of:

Compound 1
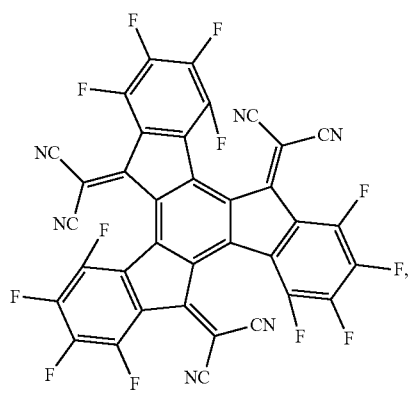

Compound 2
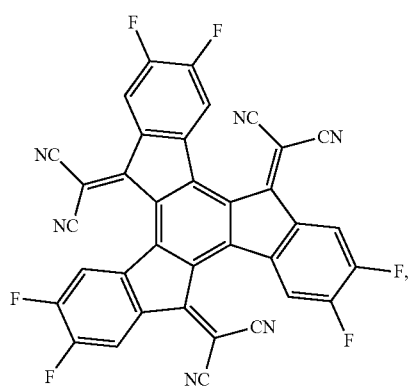

Compound 3
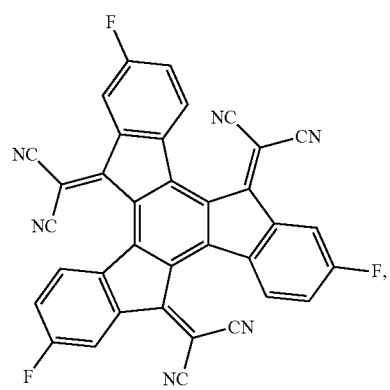

Compound 4
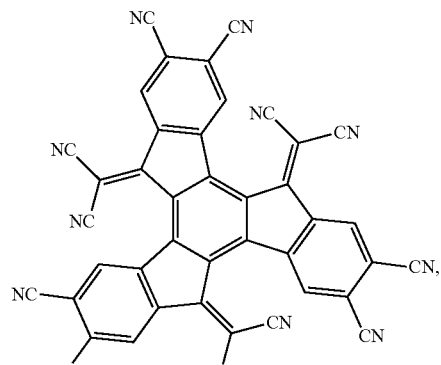

Compound 5
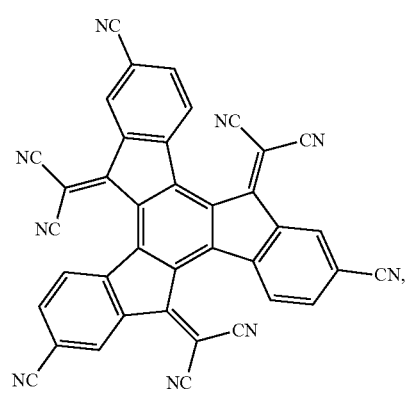

Compound 6
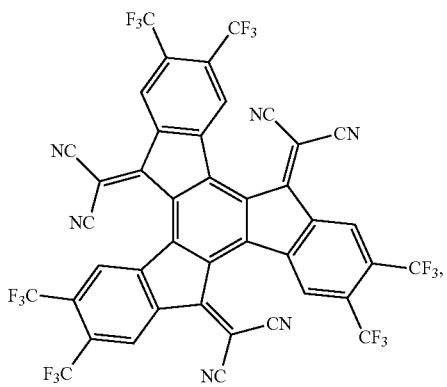

Compound 7
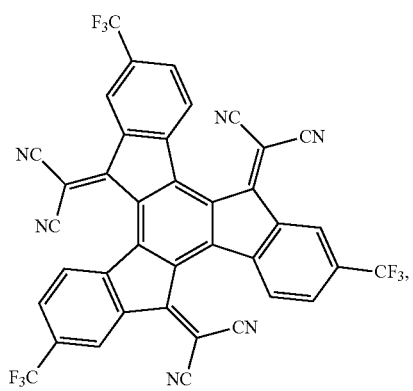

-continued
Compound 8
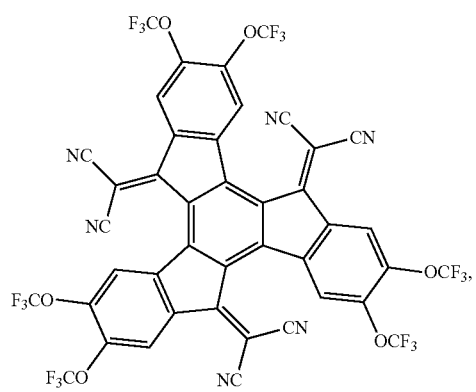
Compound 9
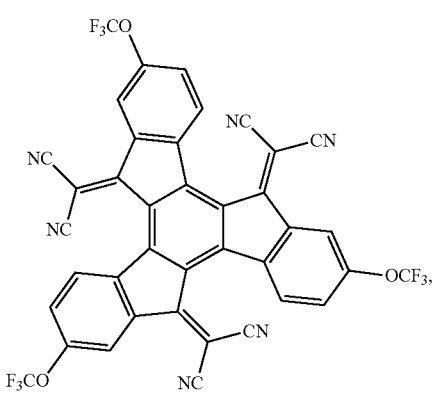
Compound 10
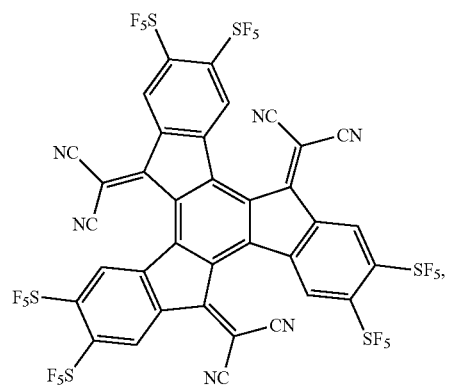
Compound 11
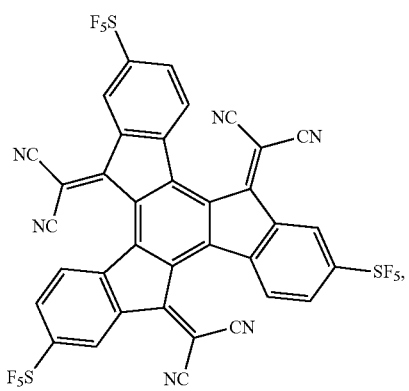
-continued
Compound 12
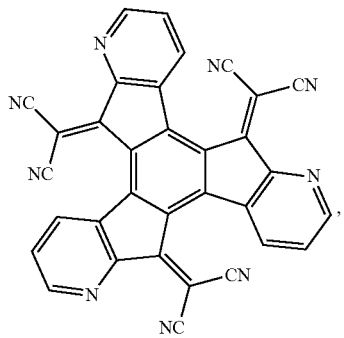
Compound 13
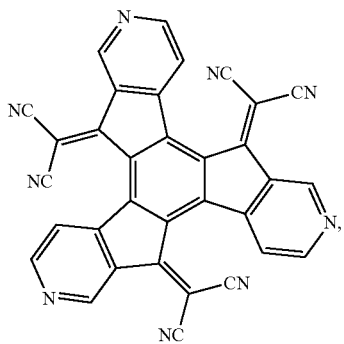
Compound 14
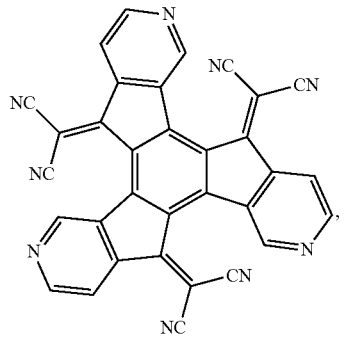
Compound 15
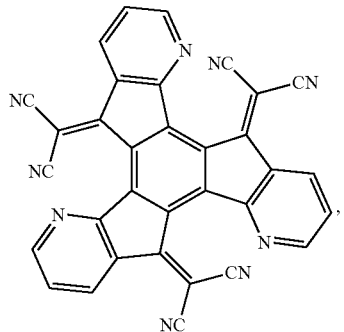

Compound 16

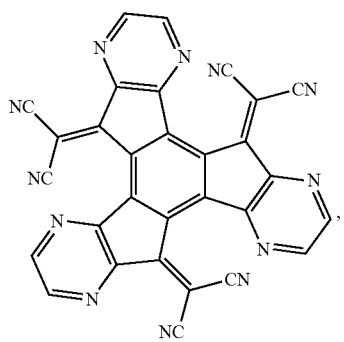

Compound 17

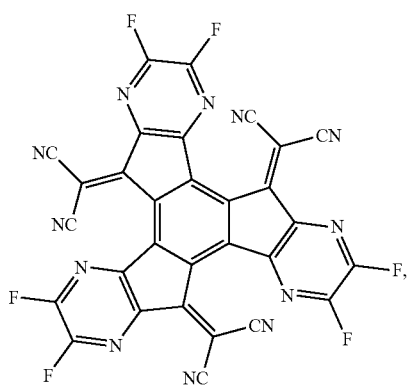

Compound 18

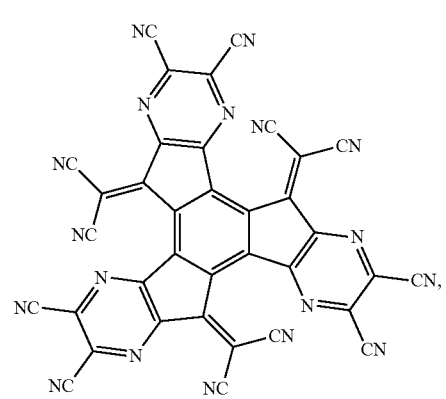

Compound 19

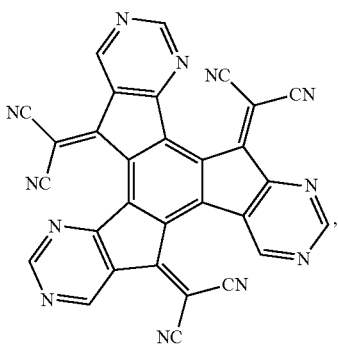

Compound 20

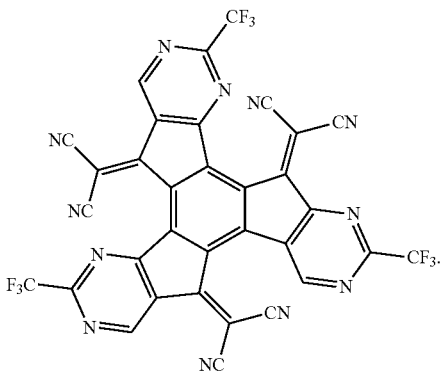

In one embodiment, wherein the hole injecting layer is a layer consisting entirely of the compound having formula 1.

In one embodiment, wherein the hole injection layer further comprises an aromatic amine compound.

In one preferred embodiment, wherein the hole injection layer further comprises an aromatic amine compound, and the aromatic amine compound is selected from the group consisting of:

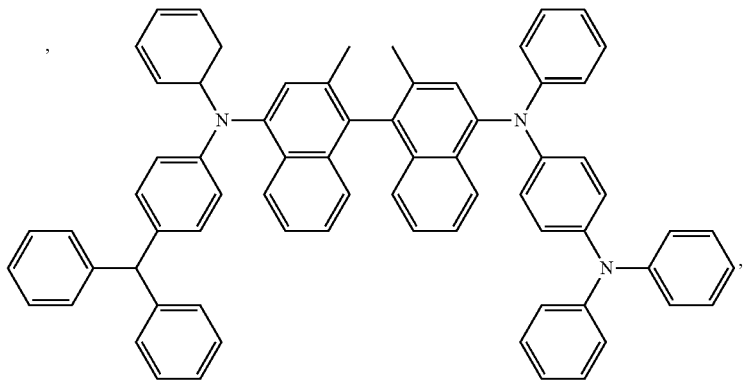

-continued
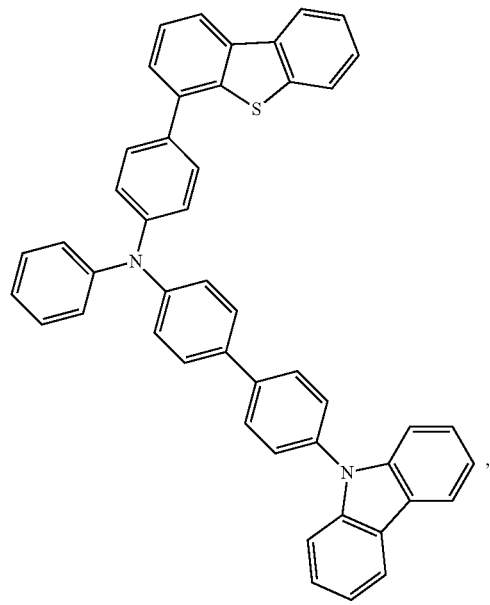
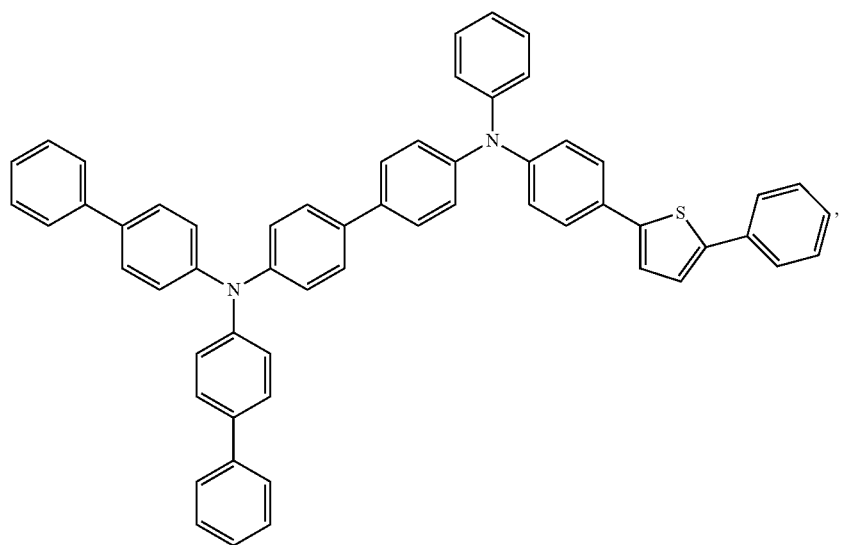
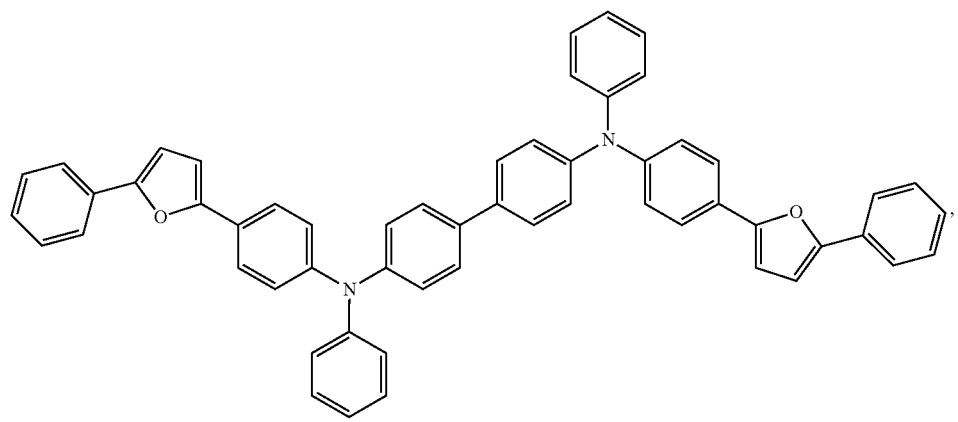

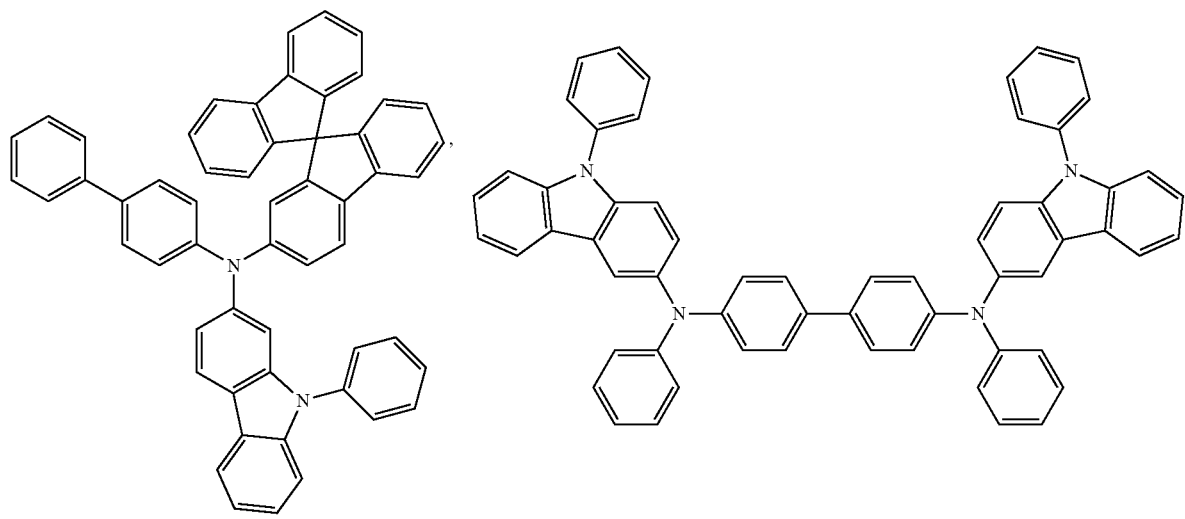
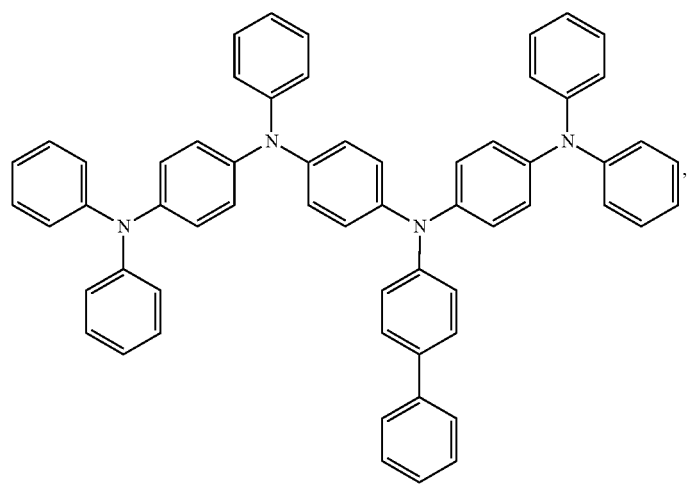
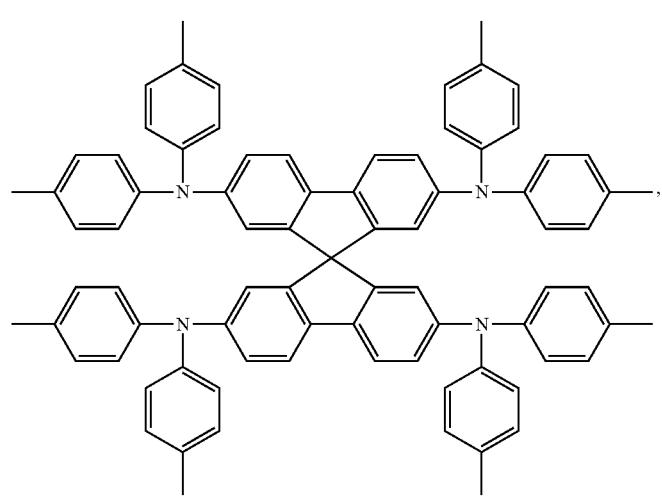

-continued
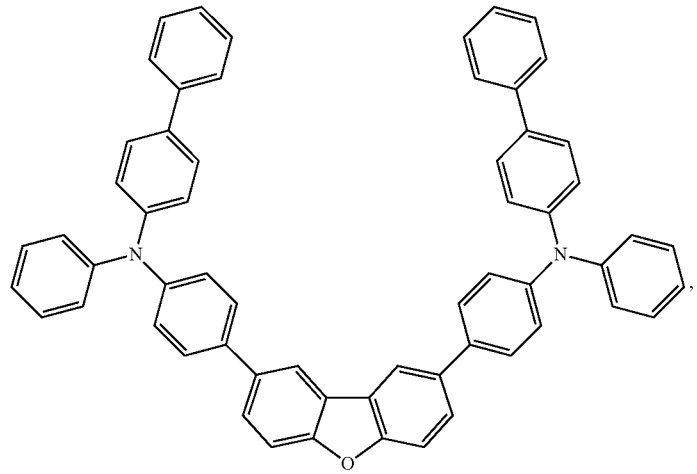
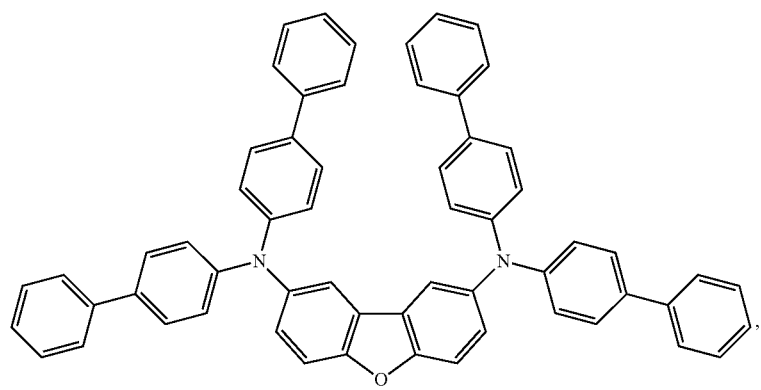
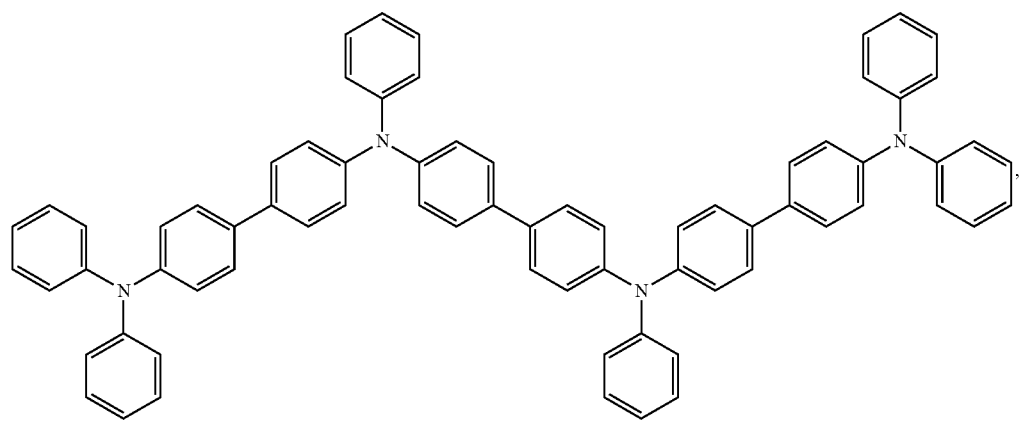

-continued
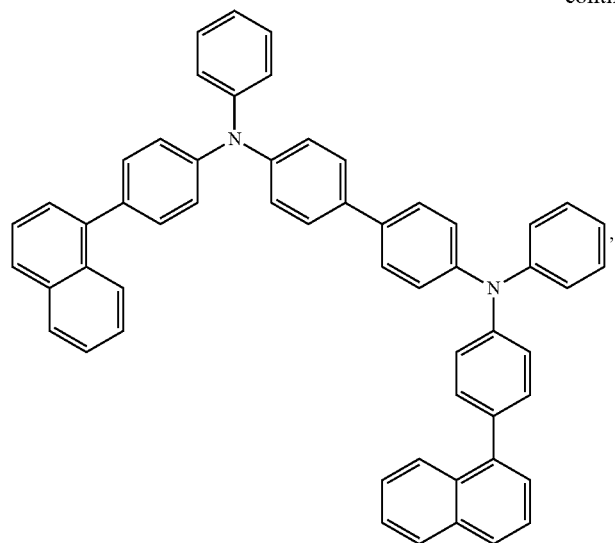
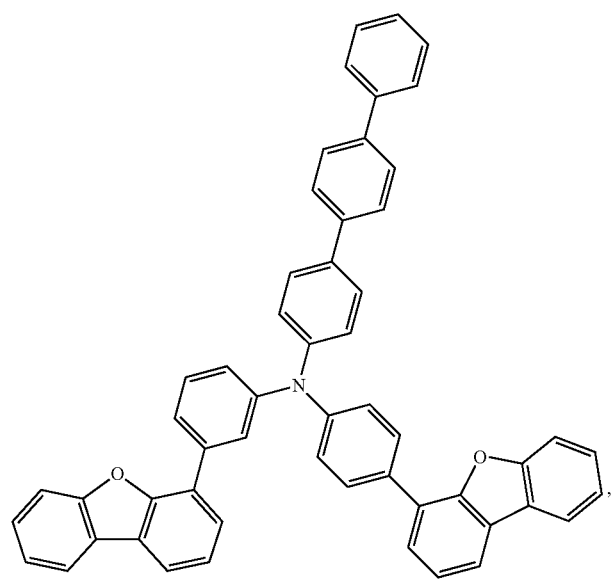
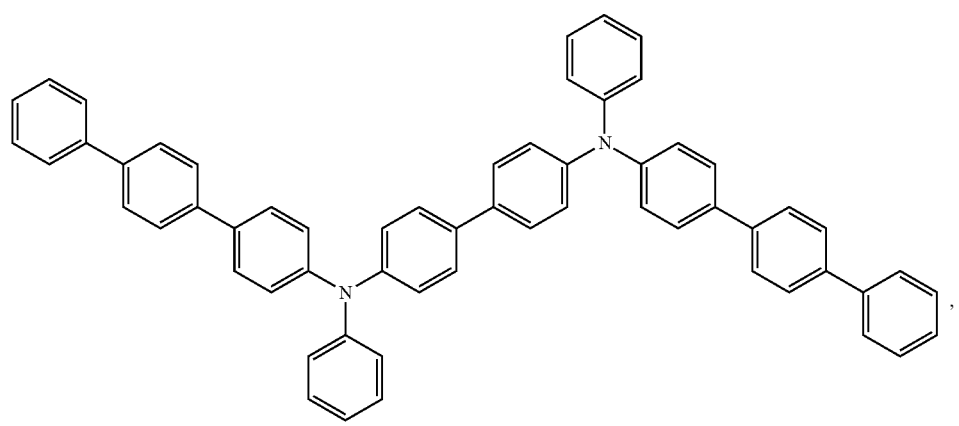

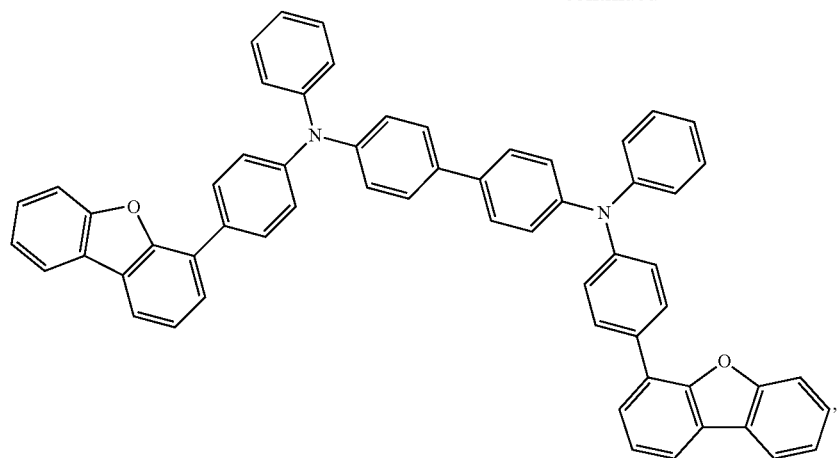
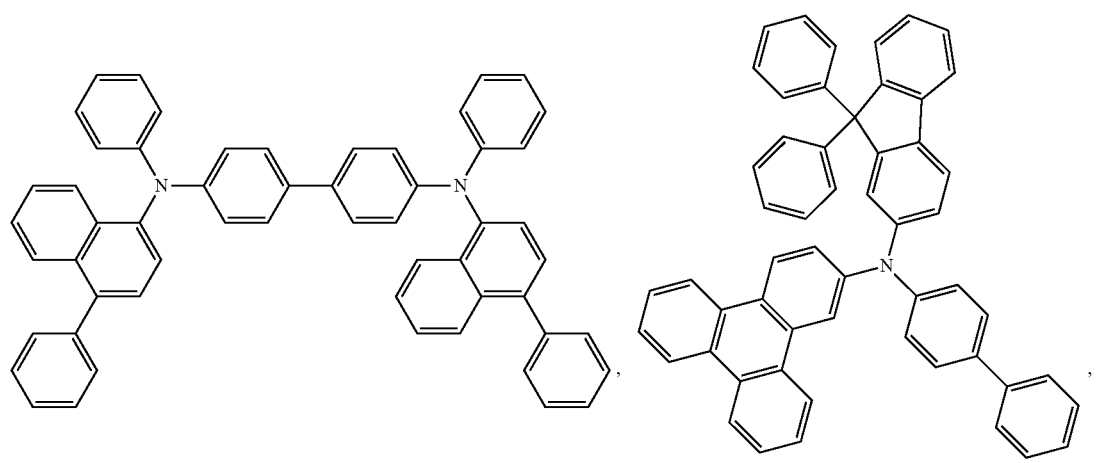
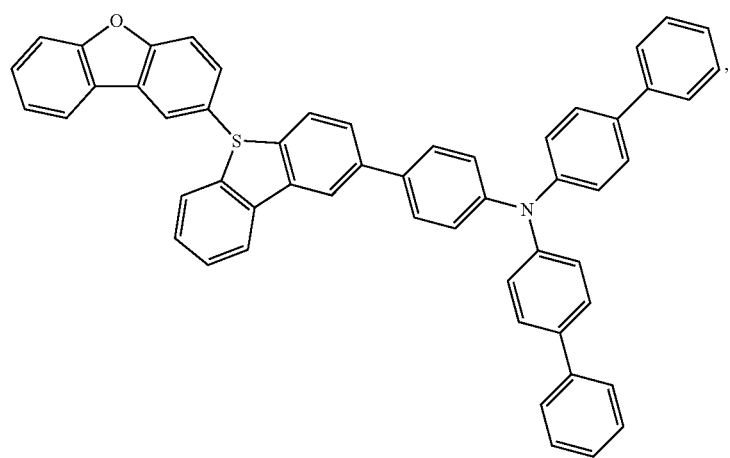

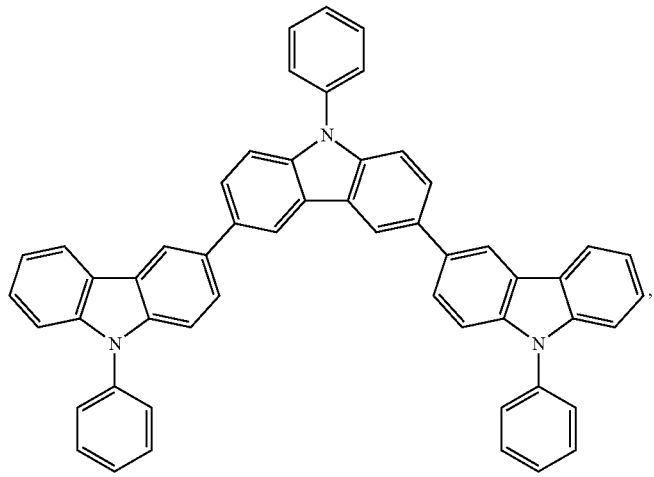
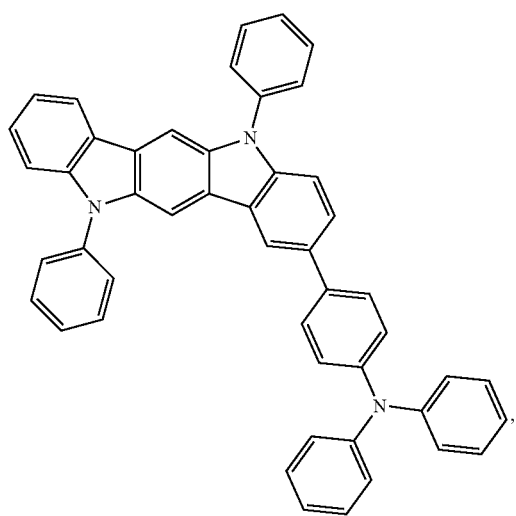
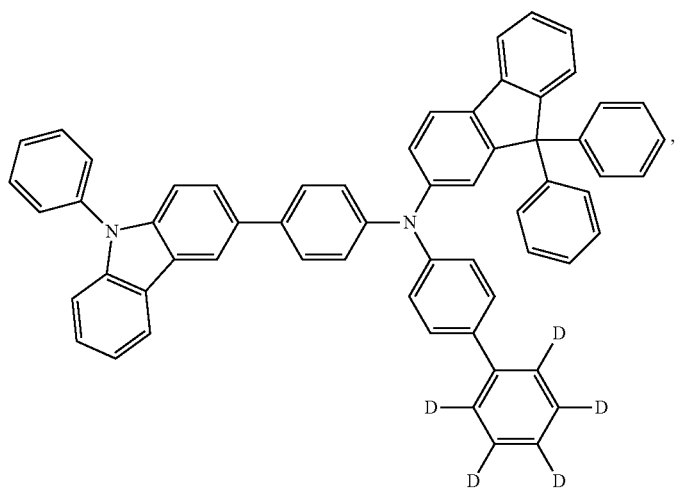

-continued
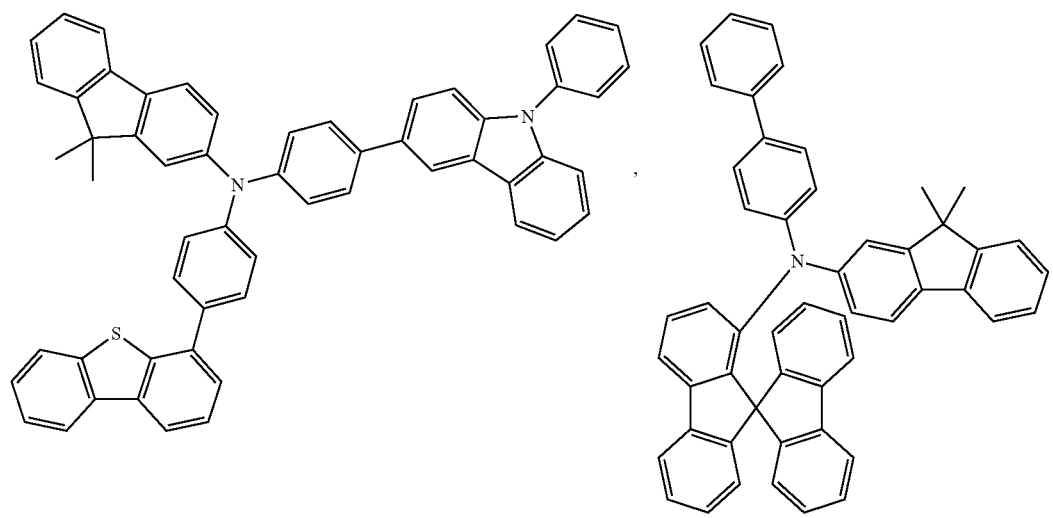
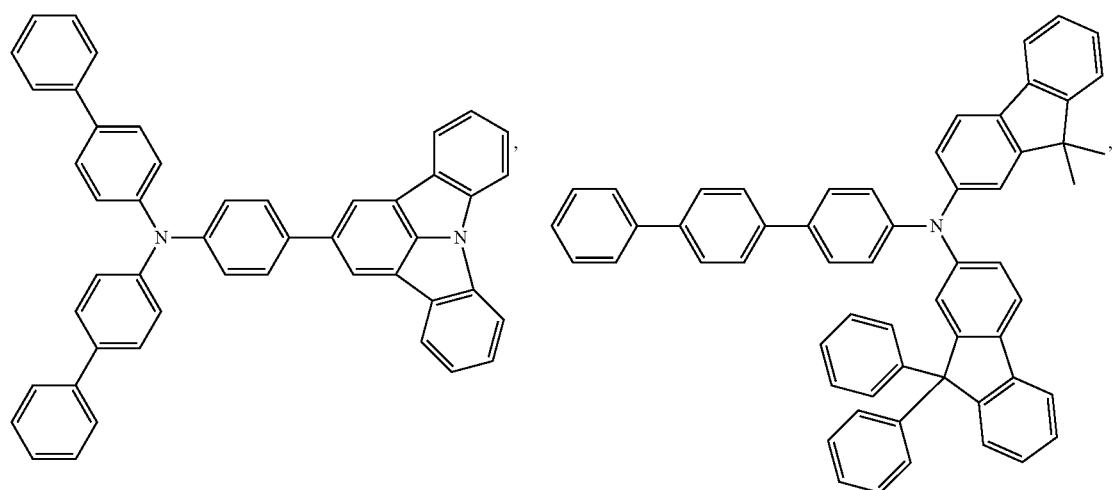
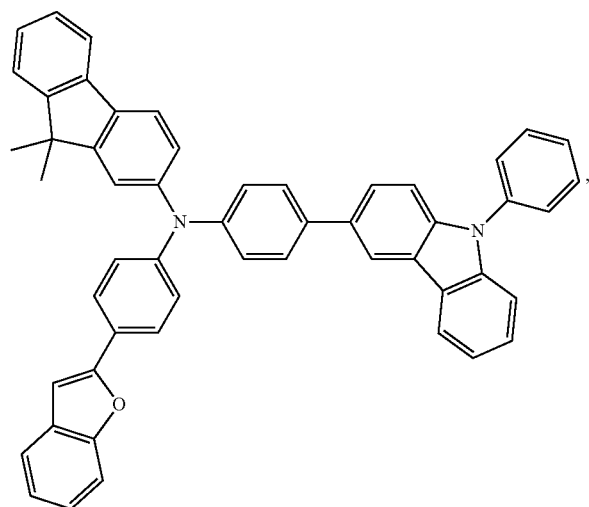

-continued
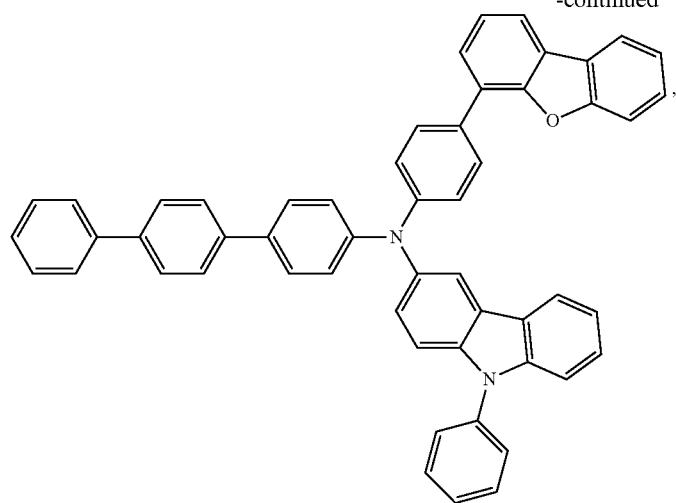
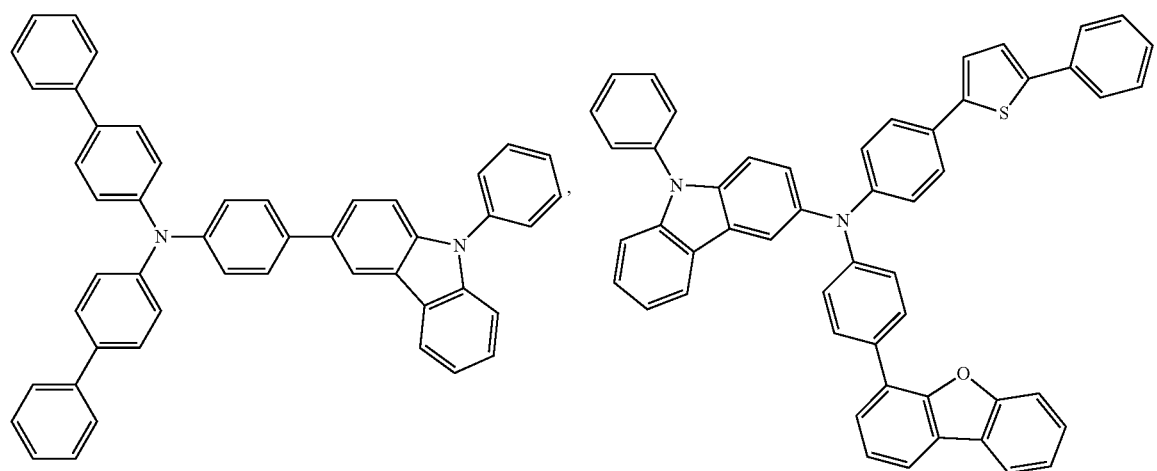
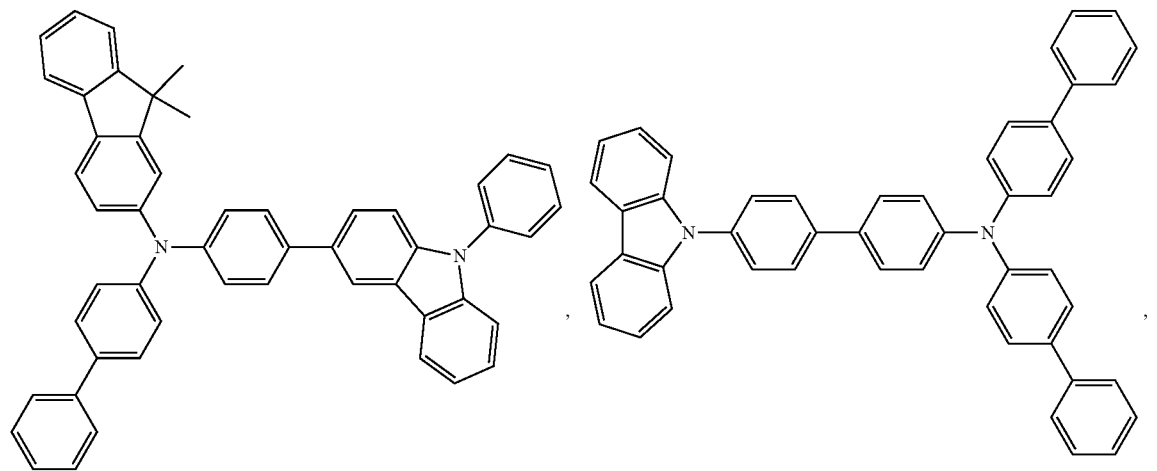

-continued
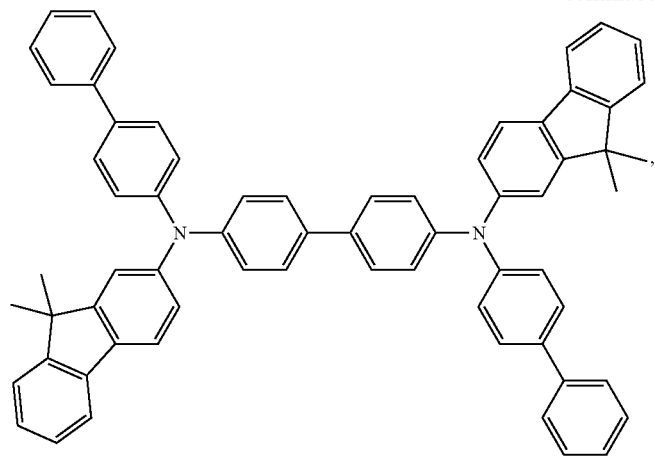
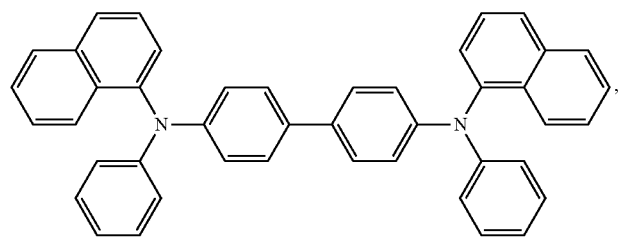
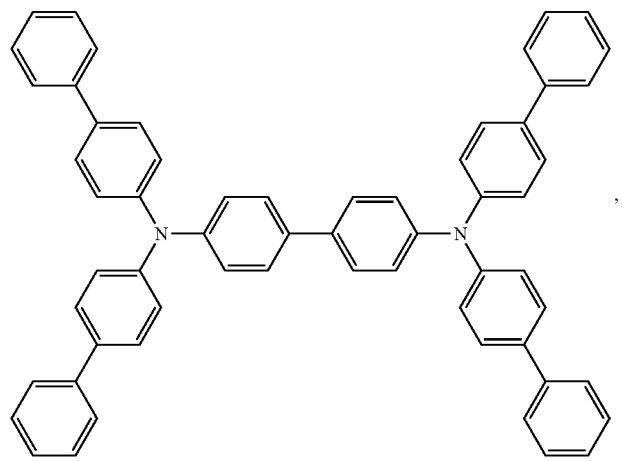
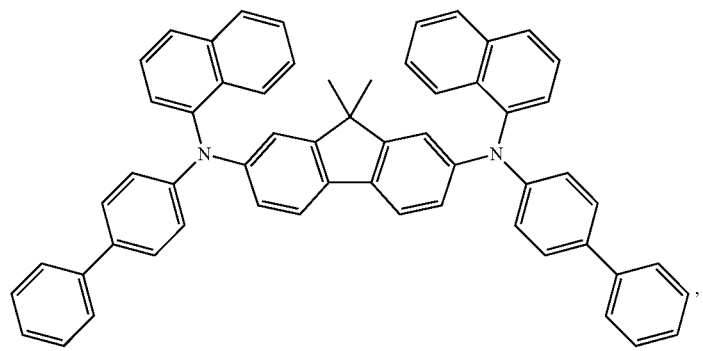

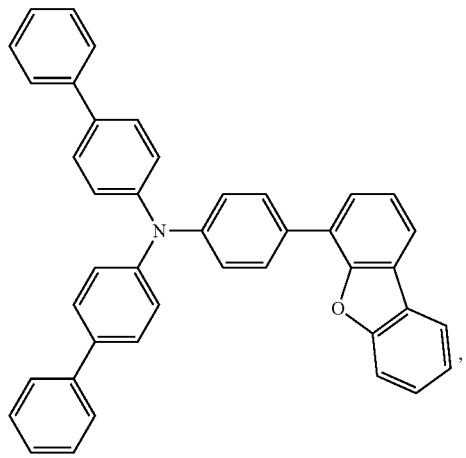

According to another embodiment, a tandem organic electroluminescent device is disclosed. The tandem organic electroluminescent device comprises: an anode, a cathode, a charge generation layer disposed between the anode and cathode, wherein the charge generation layer comprises a compound represented by formula 1:

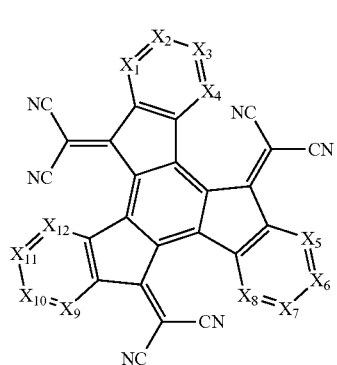

Formula 1

Wherein $X_1$ to $X_{12}$ are independently selected from CR or N;

R is selected from the group consisting of hydrogen, deuterium, halogen, a substituted or unsubstituted alkyl group having 1 to 20 carbon atoms, a substituted or unsubstituted cycloalkyl group having 3 to 20 ring carbon atoms, a substituted or unsubstituted heteroalkyl group having 1 to 20 carbon atoms, a substituted or unsubstituted arylalkyl group having 7 to 30 carbon atoms, a substituted or unsubstituted alkoxy group having 1 to 20 carbon atoms, a substituted or unsubstituted aryloxy group having 6 to 30 carbon atoms, a substituted or unsubstituted alkenyl group having 2 to 20 carbon atoms, a substituted or unsubstituted aryl group having 6 to 30 carbon atoms, a substituted or unsubstituted heteroaryl group having 3 to 30 carbon atoms, a substituted or unsubstituted alkylsilyl group having 3 to 20 carbon atoms, a substituted or unsubstituted arylsilyl group having 6 to 20 carbon atoms, a substituted or unsubstituted amino group having 0 to 20 carbon atoms, an acyl group, a carbonyl group, a carboxylic acid group, an ester group, nitrile, isonitrile, sulfanyl, sulfinyl, sulfonyl, phosphino, and combinations thereof;

R can be the same or different when there are multiple R groups present;

Any adjacent R groups are optionally joined to form a ring or a fused structure.

In one embodiment, wherein R is selected from the group consisting of nitro, fluorine, cyano, trifluoromethyl, trifluoromethoxy, and pentafluorosulfide.

In one preferred embodiment, wherein the compound having formula 1 is selected from the group consisting of:

Compound 1

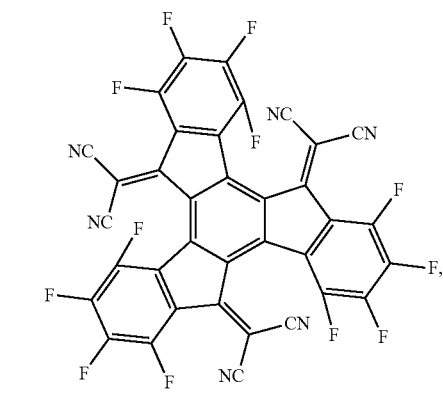

Compound 2

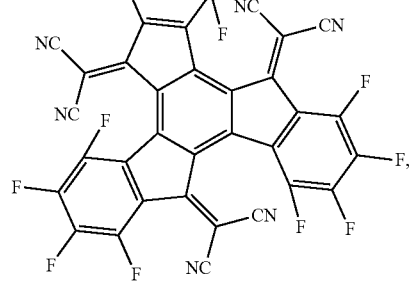

-continued
Compound 3
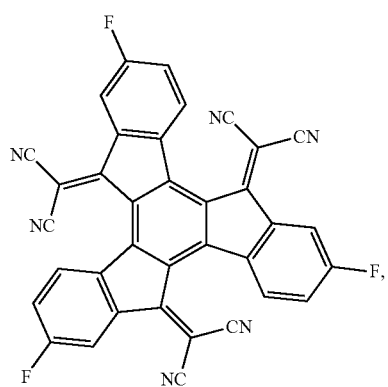
Compound 4
Compound 5
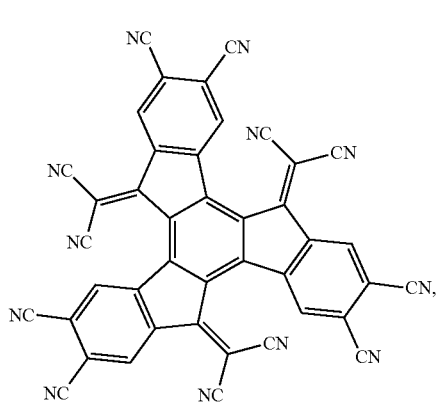
Compound 6
-continued
Compound 7
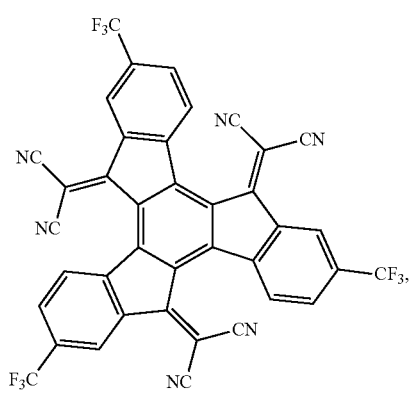
Compound 8
Compound 9
Compound 10

Compound 11
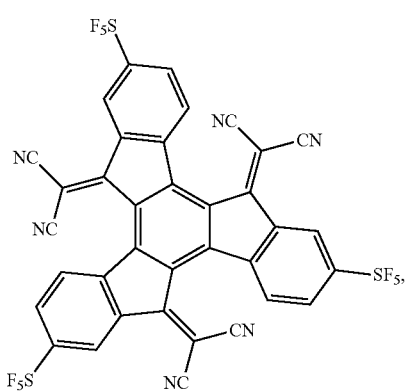
Compound 12
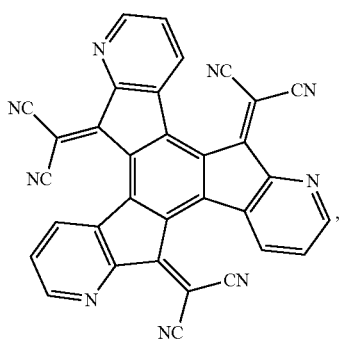
Compound 13
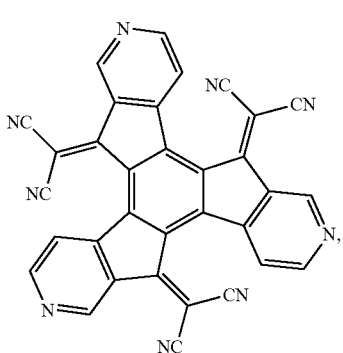
Compound 14
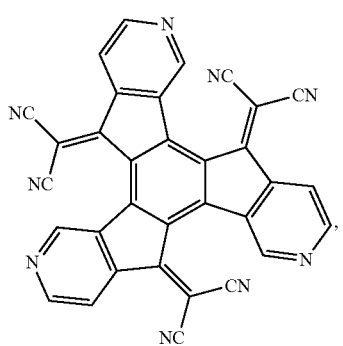
Compound 15
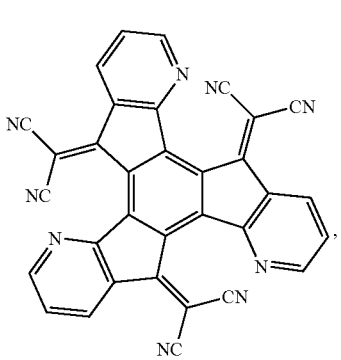
Compound 16
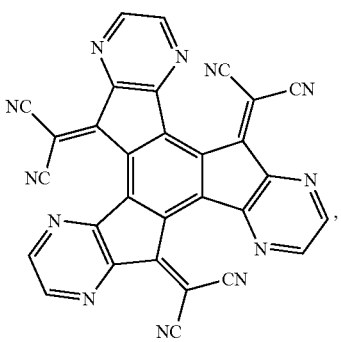
Compound 17
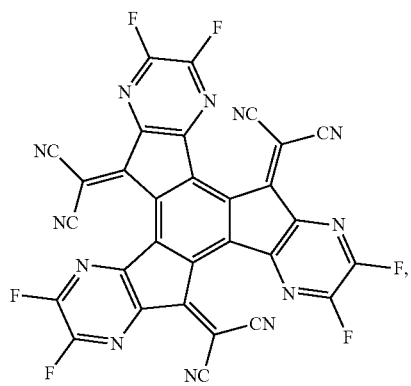

Compound 18

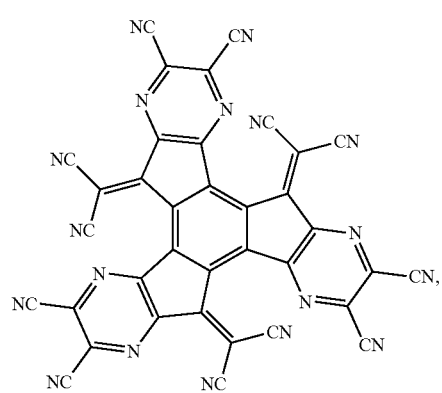

Compound 19

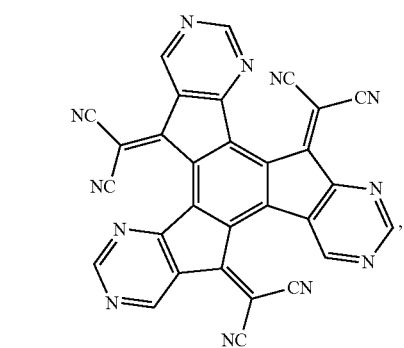

Compound 20

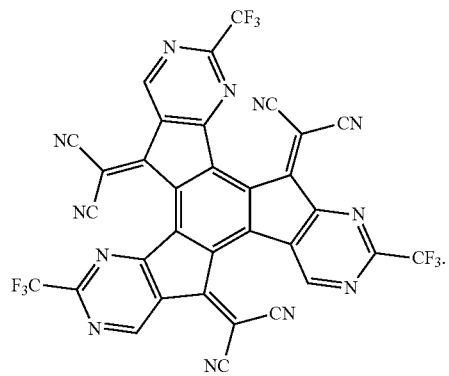

In one embodiment, wherein the charge generation layer is a layer consisting entirely of the compound having formula 1.

In one embodiment, wherein the charge generation layer is a P-type charge generation layer.

In one embodiment, wherein the charge generation layer further comprises an aromatic amine compound.

In one preferred embodiment, wherein the charge generation layer further comprises an aromatic amine compound, and the aromatic amine compound is selected from the group consisting of:

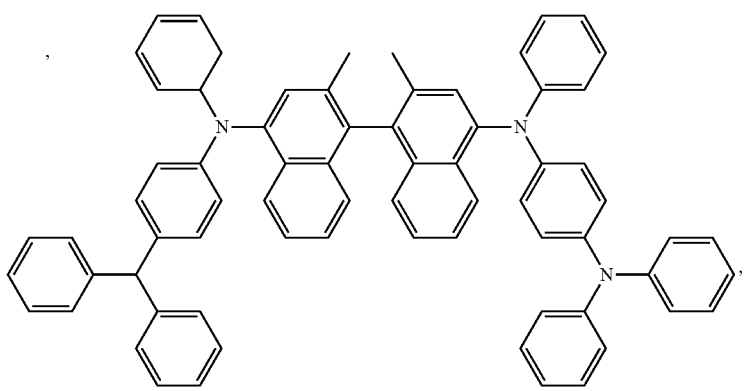

-continued
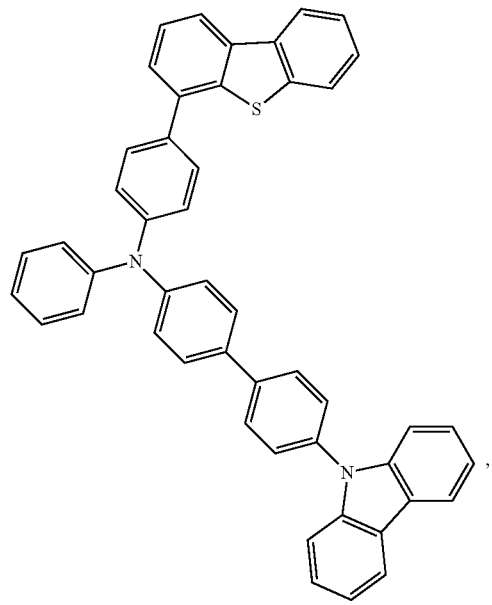
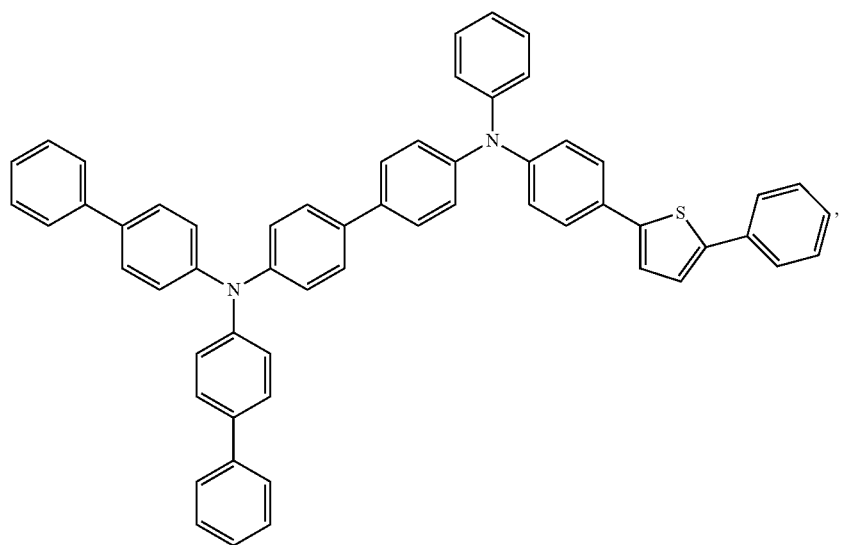
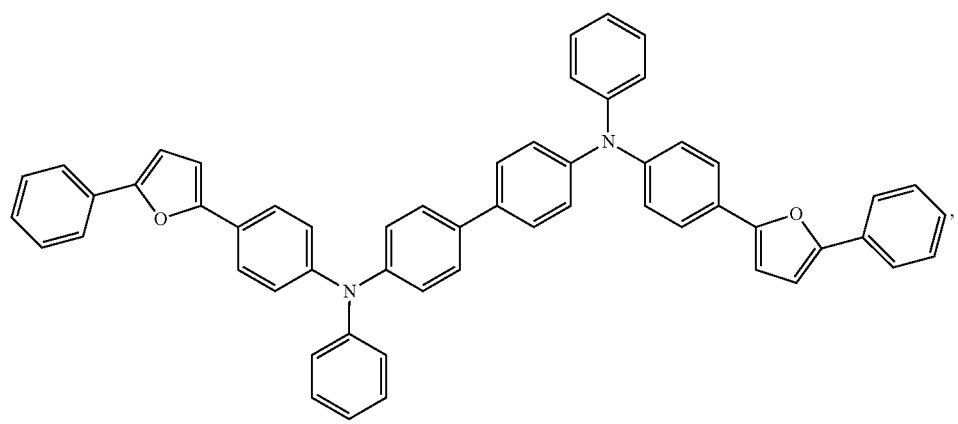

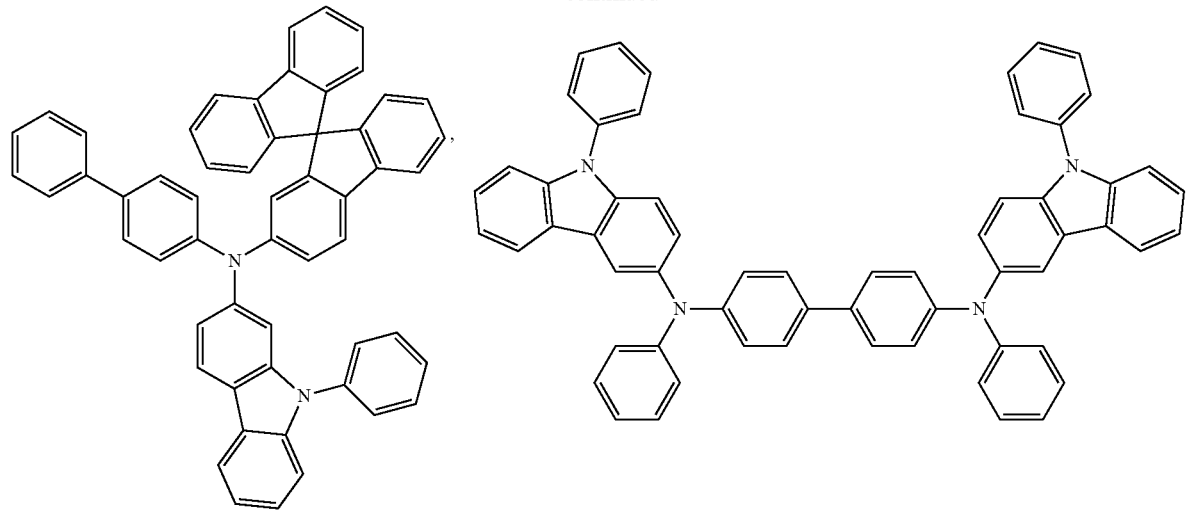
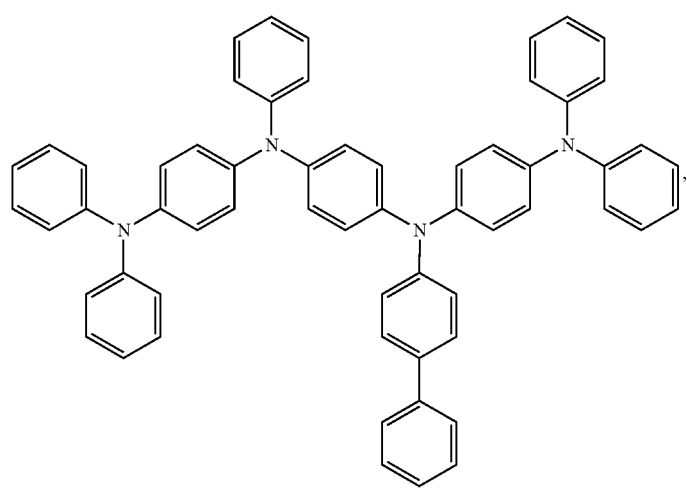
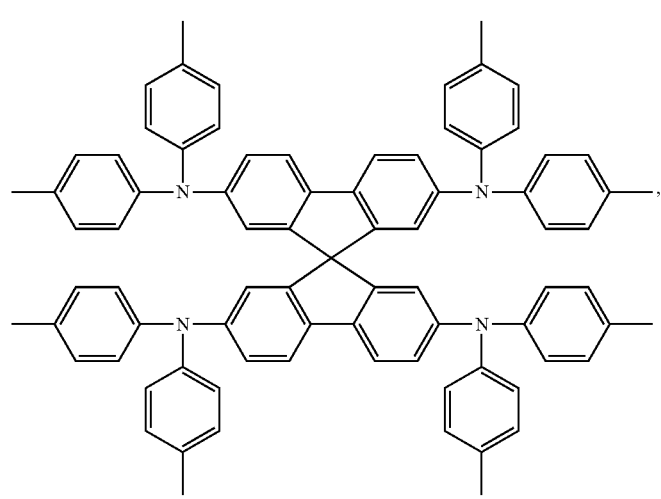

-continued
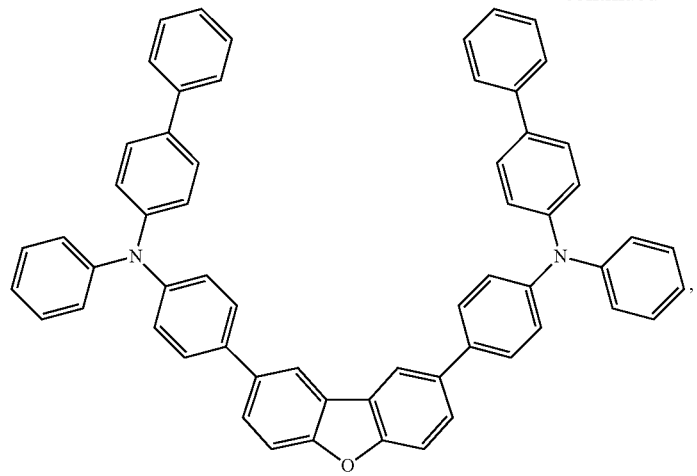
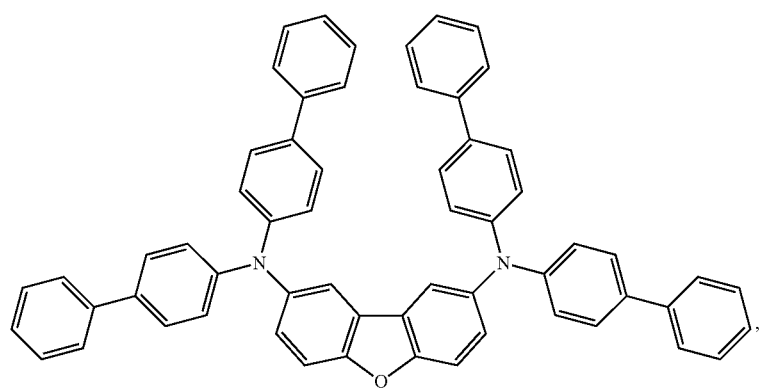
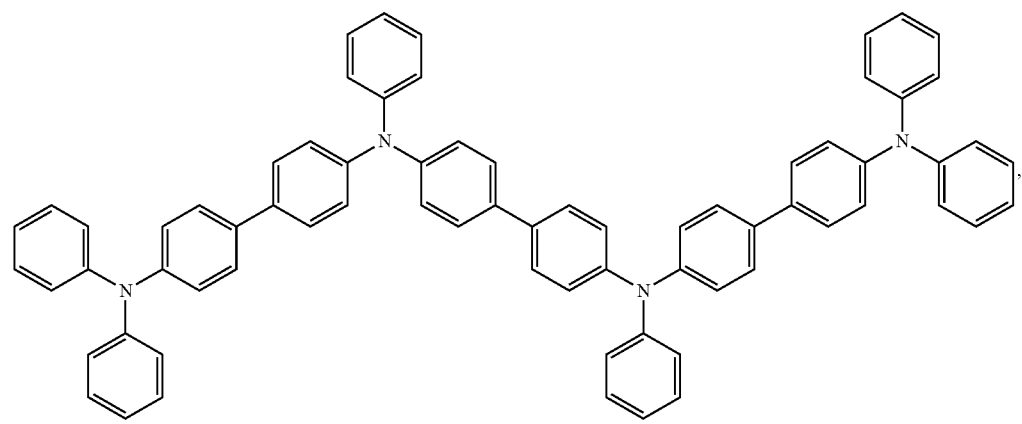

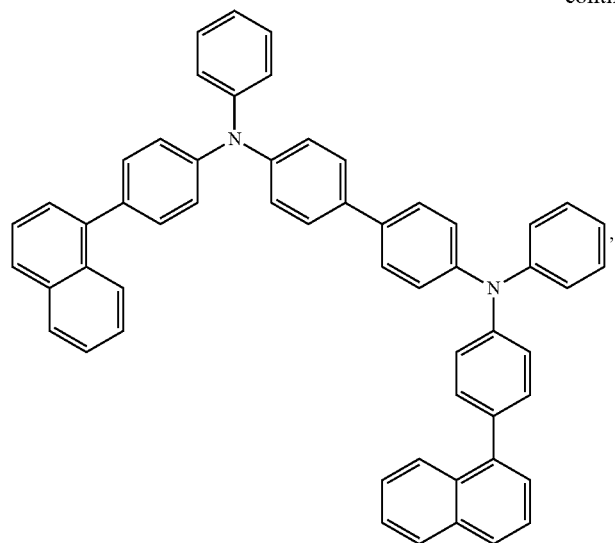
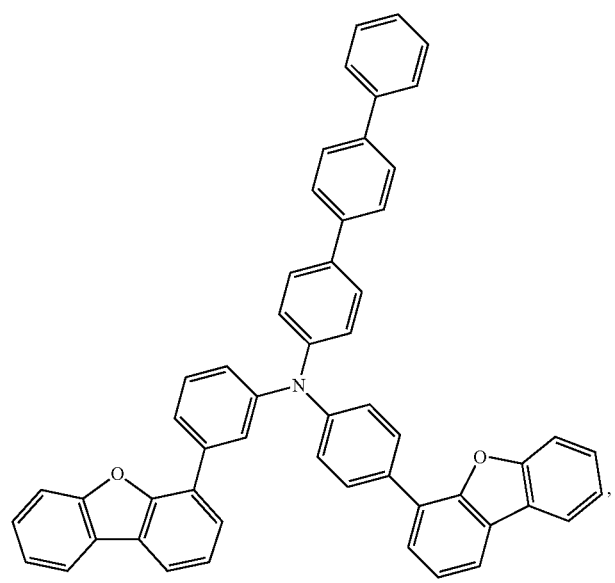
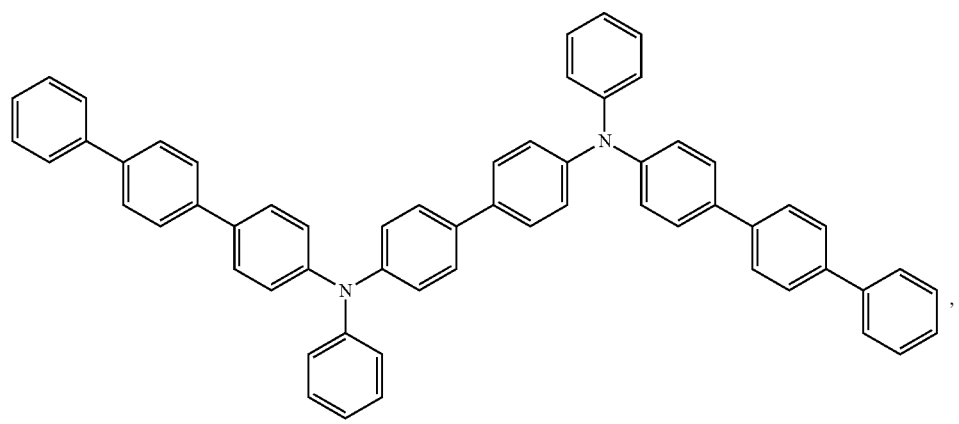

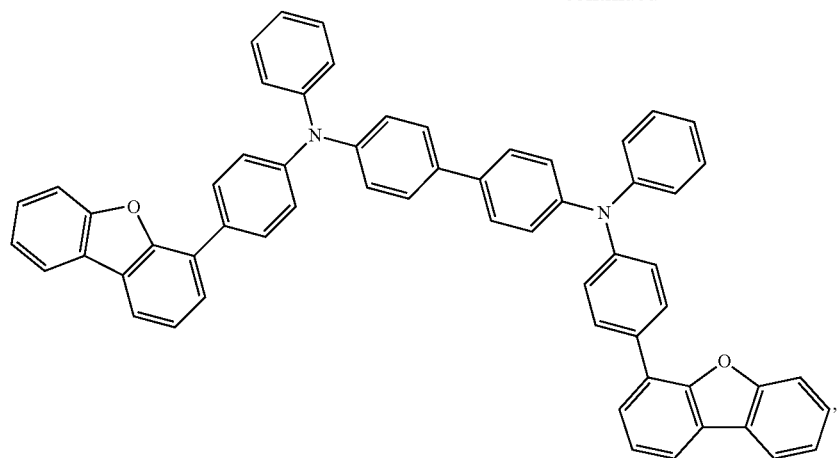
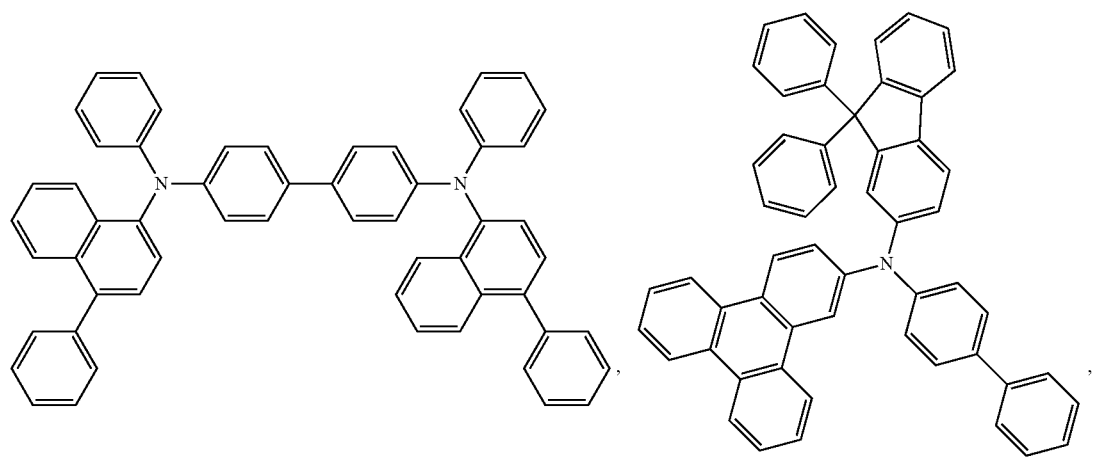
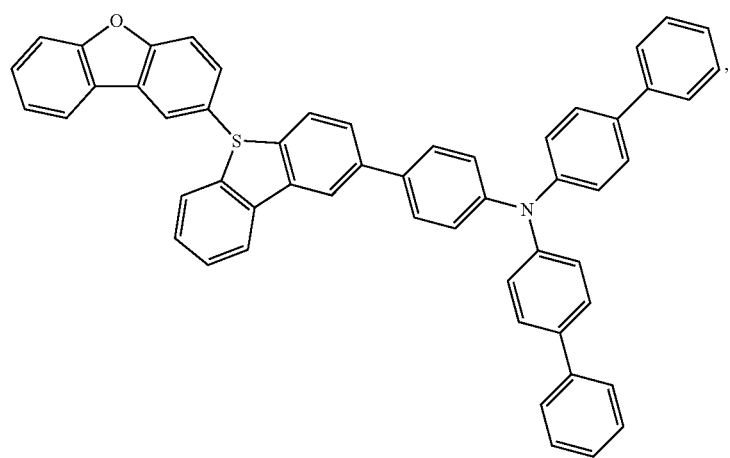

-continued
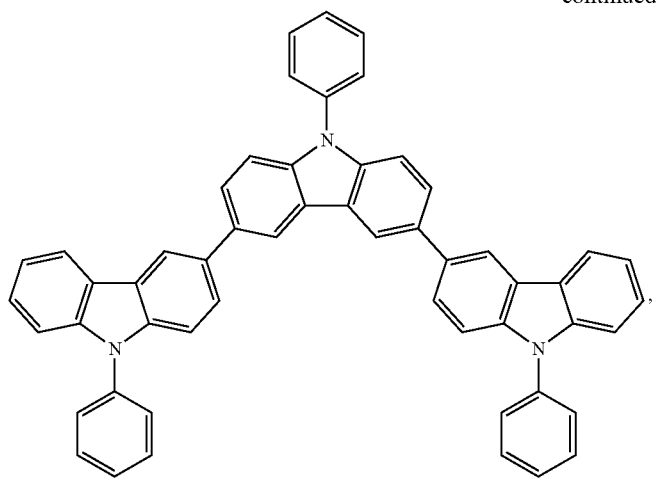
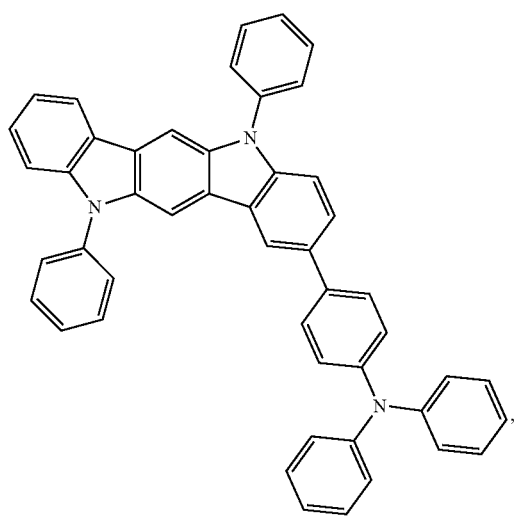
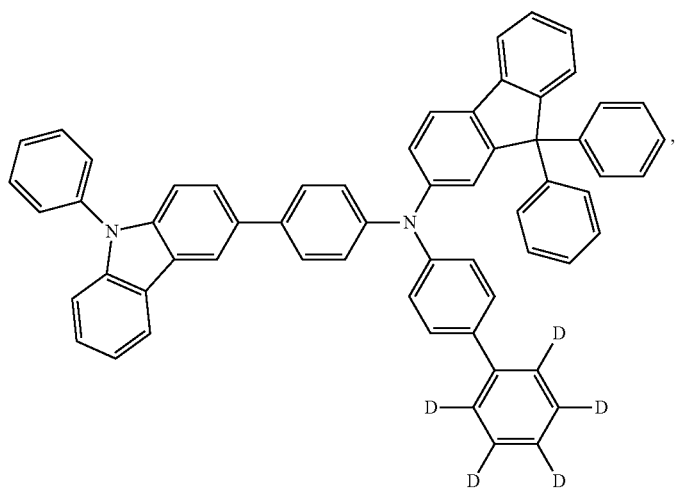

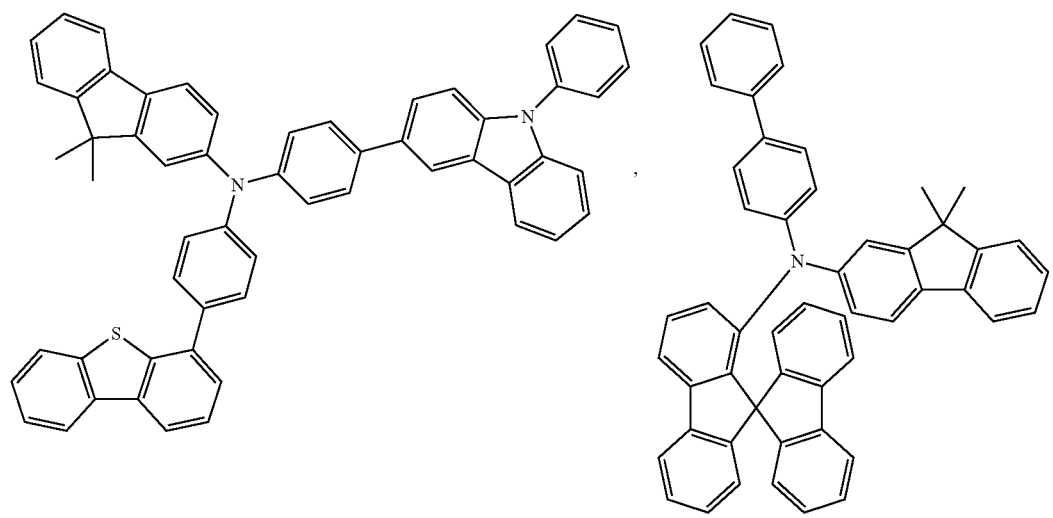
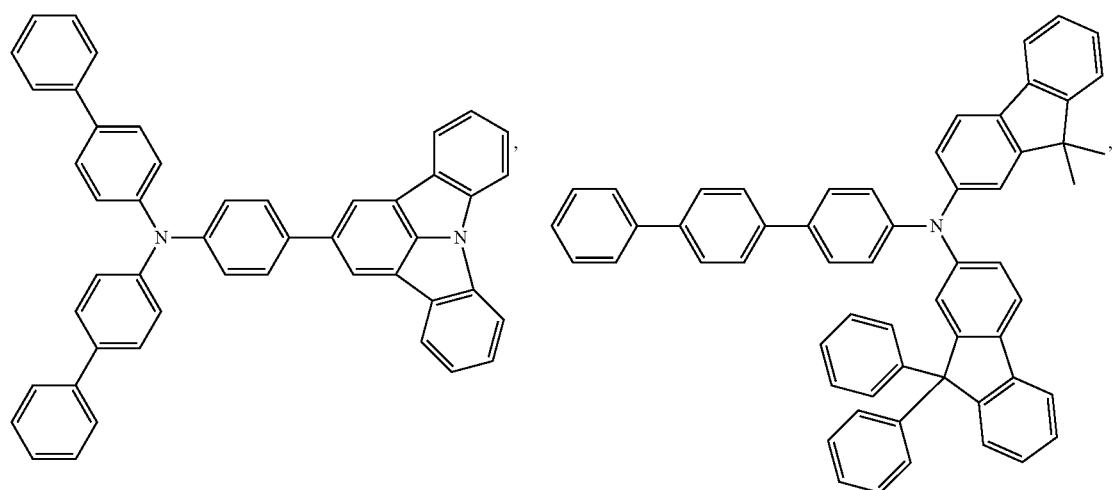
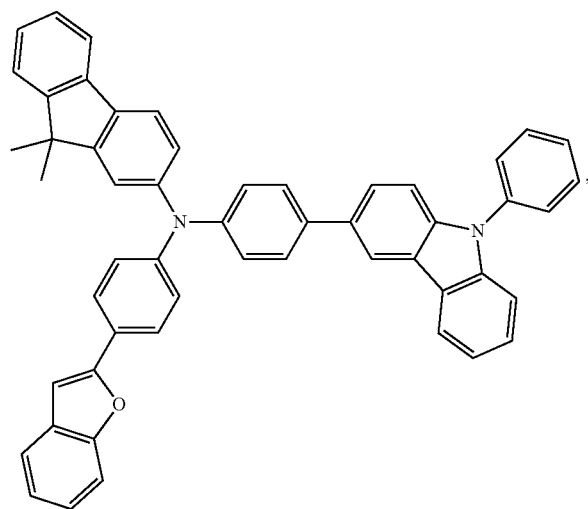

-continued
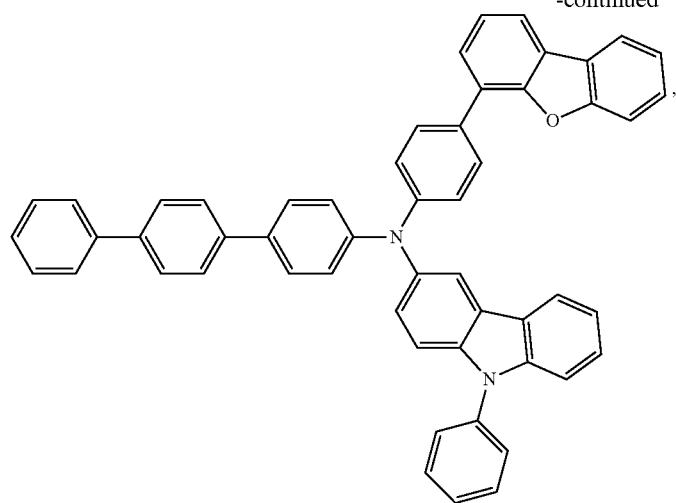
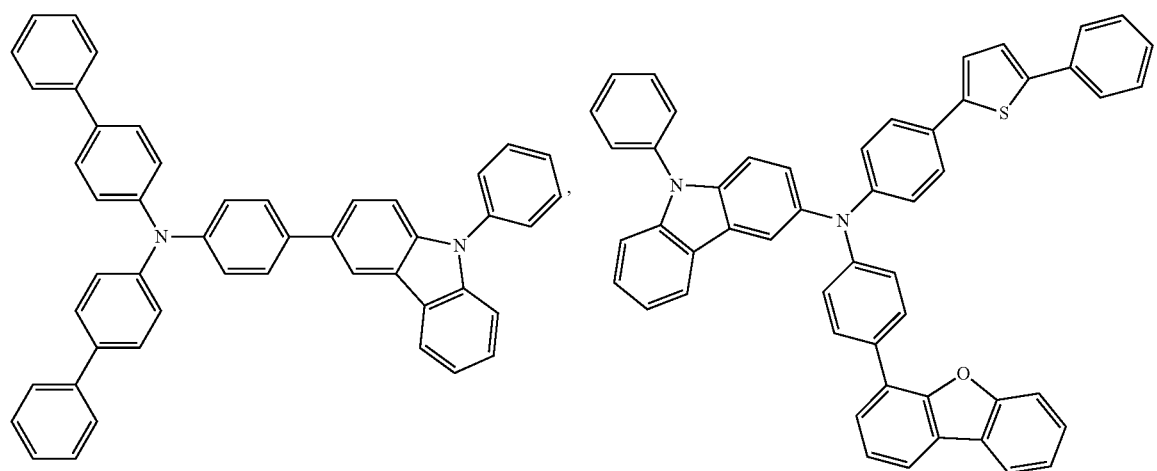
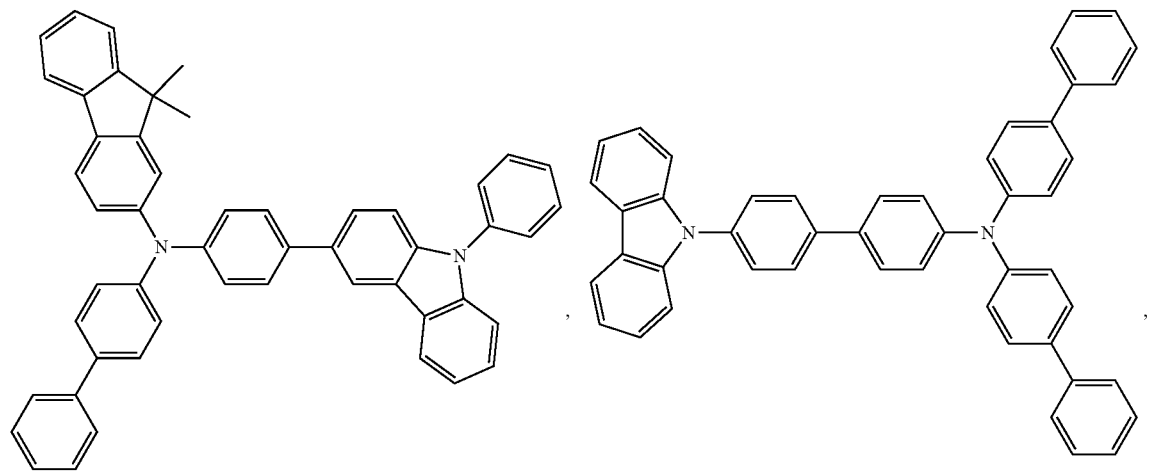

-continued
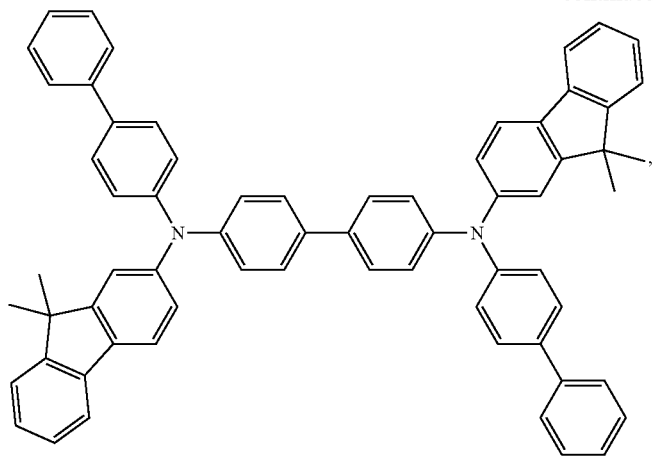
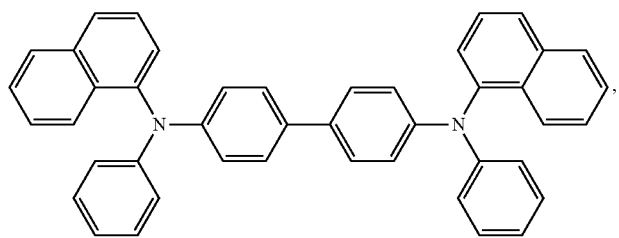
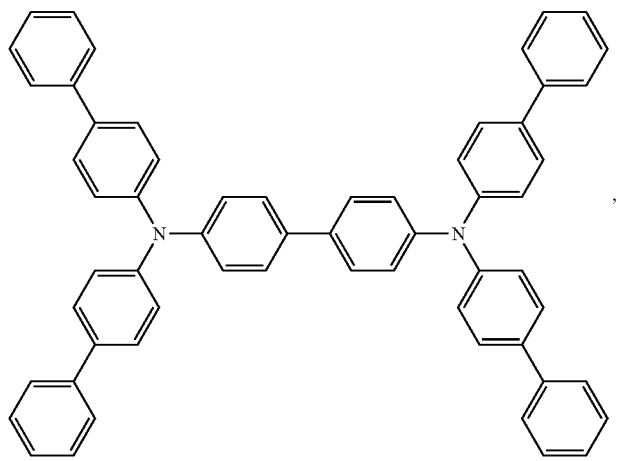
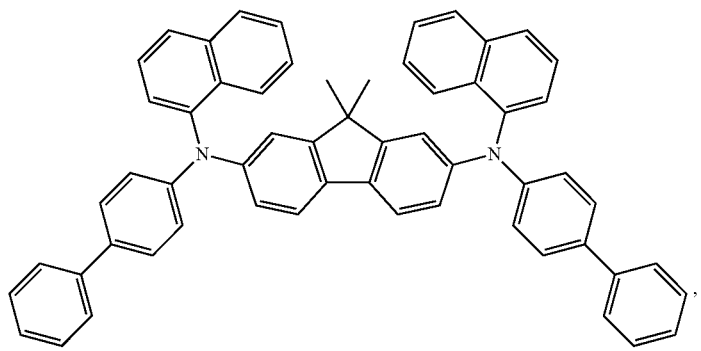

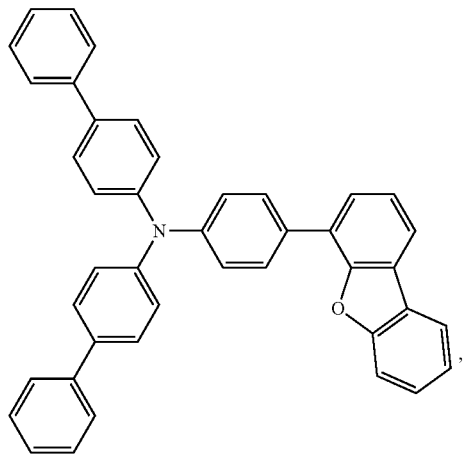
According to an embodiment of the present invention, there is also disclosed a compound having a structure selected from the group consisting of:
Compound 4
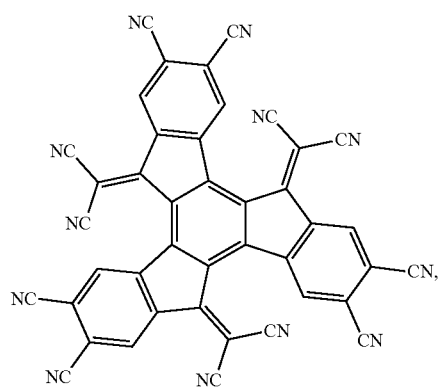
Compound 5
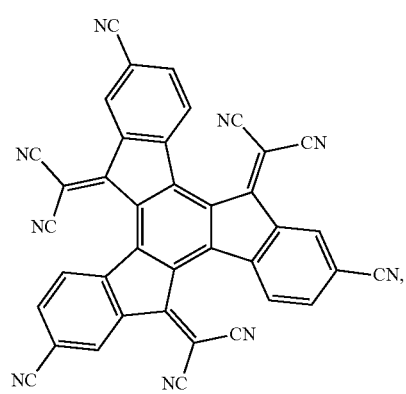
Compound 6
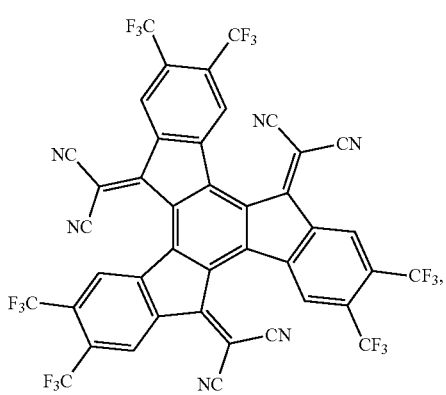
Compound 7
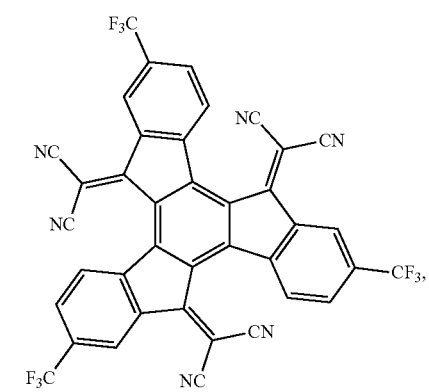

Compound 8

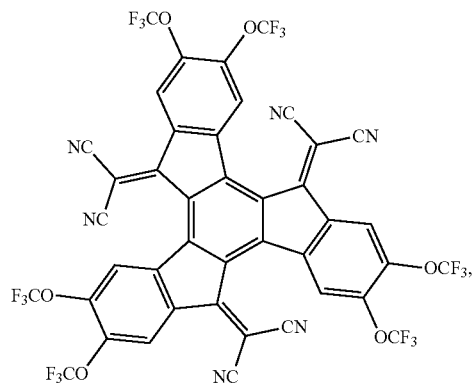

Compound 9

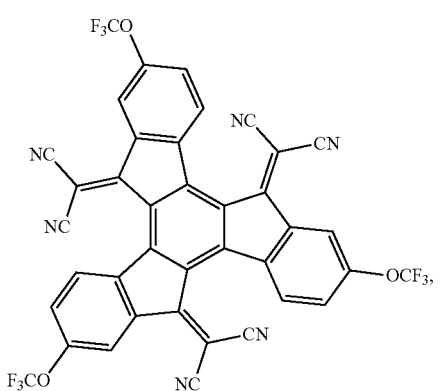

Compound 10

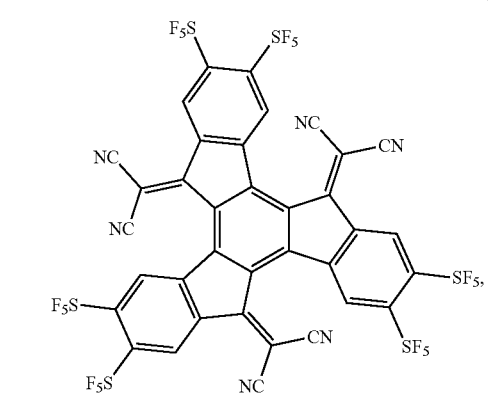

Compound 11

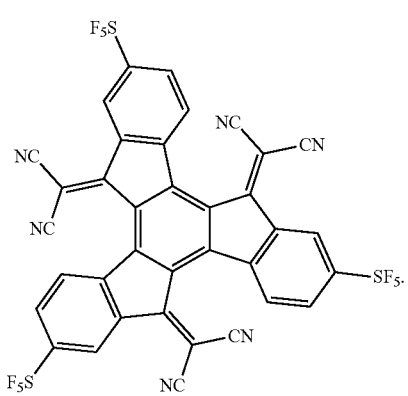

Combination with Other Materials

The materials described herein as useful for a particular layer in an organic light emitting device may be used in combination with a wide variety of other materials present in the device. The combinations of these materials are described in more detail in U.S. Pat. App. No. 20160359122 at paragraphs 0132-0161, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

The materials described herein as useful for a particular layer in an organic light emitting device may be used in combination with a variety of other materials present in the device. For example, emissive dopants disclosed herein may be used in combination with a wide variety of hosts, transport layers, blocking layers, injection layers, electrodes and other layers that may be present. The combination of these materials is described in detail in paragraphs 0080-0101 of U.S. Pat. App. No. 20150349273, which are incorporated by reference in its entirety. The materials described or referred to the disclosure are non-limiting examples of materials that may be useful in combination with the compounds disclosed herein, and one of skill in the art can readily consult the literature to identify other materials that may be useful in combination.

In the embodiments of material synthesis, all reactions were performed under nitrogen protection unless otherwise stated. All reaction solvents were anhydrous and used as received from commercial sources. Synthetic products were structurally confirmed and tested for properties using one or more conventional equipment in the art (including, but not limited to, nuclear magnetic resonance instrument produced by BRUKER, liquid chromatograph produced by SHIMADZU, liquid chromatography-mass spectrometer produced by SHIMADZU, gas chromatography-mass spectrometer produced by SHIMADZU, differential Scanning calorimeters produced by SHIMADZU, fluorescence spectrophotometer produced by SHANGHAI LENGGUANG TECH., electrochemical workstation produced by WUHAN CORRTEST, and sublimation apparatus produced by ANHUI BEQ, etc.) by methods well known to the persons skilled in the art. In the embodiments of the device, the characteristics of the device were also tested using conventional equipment in the art (including, but not limited to, evaporator produced by ANGSTROM ENGINEERING, optical testing system produced by SUZHOU FATAR, life testing system produced by SUZHOU FATAR, and ellipsometer produced by BEIJING ELLITOP, etc.) by methods well known to the persons skilled in the art. As the persons skilled in the art are aware of the above-mentioned equipment use, test methods and other related contents, the inherent data of the sample can be obtained with certainty and without influence, so the above related contents are not further described in this patent.

Material Synthesis Example

The method for preparing the compounds of the present invention is not limited. The compound 9 is exemplified as a typical but non-limiting example, and its synthesis route and preparation method are as follows:

Synthesis of Compound 9

Step 1: Synthesis of 1,3,5-tribromo-2,4,6-tris(bromomethyl)benzene

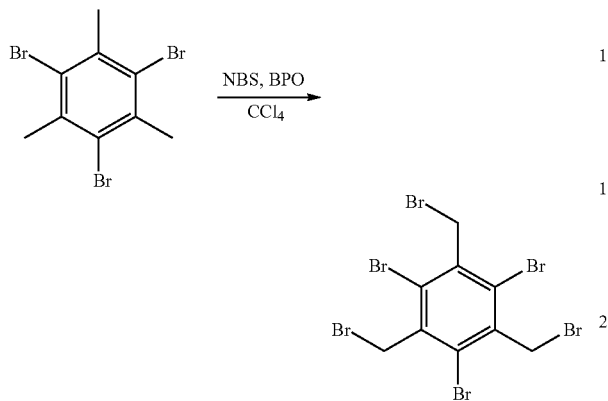

In a three-neck flask was added 1,3,5-tribromo-2,4,6-trimethylbenzene (20 g, 56 mmol), 1-bromopyrrolidine-2,5-dione (NBS) (36 g, 201.7 mmol), Dibenzoyl peroxide (BPO) (1.36 g, 5.6 mmol, 10 mol %), and $CCl_4$ (600 mL). The reaction mixture was refluxed overnight and the reaction was stopped. After cooled to room temperature, the solvent was evaporated. The crude product was added 400 mL of methanol and refluxed for 1 h. The solid was then collected by filtration and dried to obtain desired product (31.6 g, 95% yield).

Step 2: Synthesis of (2,4,6-tribromobenzene-1,3,5-triyl)tris(methylene) triacetate

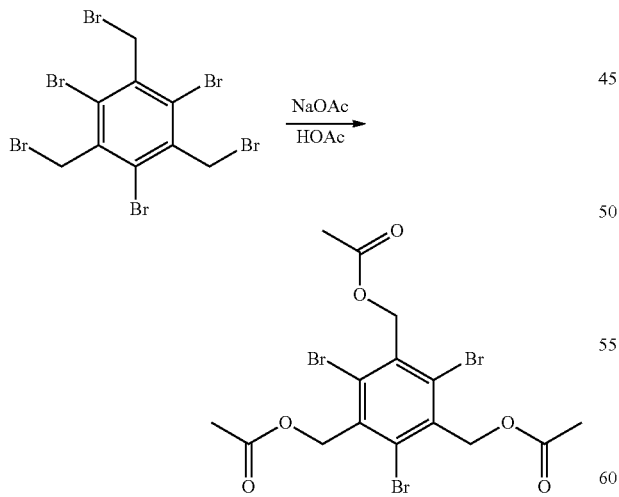

1,3,5-tribromo-2,4,6-tris(bromomethyl)benzene (31.2 g, 53.2 mmol), sodium acetate (26.2 g, 319 mmol) and acetic acid (500 mL) were added to a three-neck flask. The mixture was refluxed overnight. After cooled to room temperature, the reaction mixture was added 500 mL of water. The white precipitate was collected by filtration. The crude was purified by a silica gel plug to afford desired product (26.8 g, 94.8% yield).

Step 3: Synthesis of (4,4''-bis(trifluoromethoxy)-5'-(4-(trifluoromethoxy)phenyl)-[1,1':3',1''-terphenyl]-2',4',6'-triyl)tris(methylene) triacetate

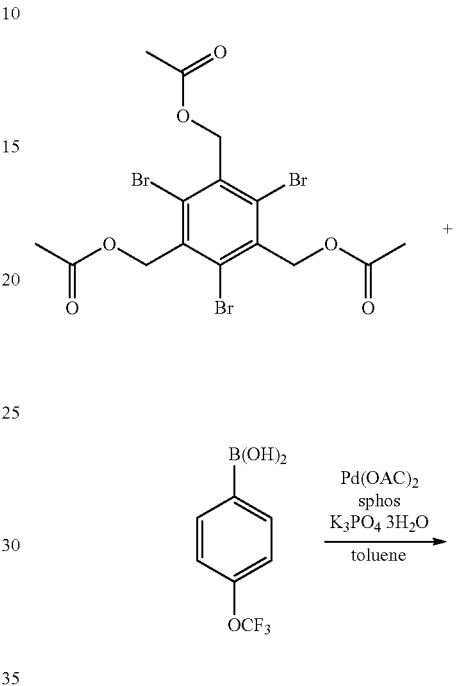

(2,4,6-tribromobenzene-1,3,5-triyl)tris(methylene) triacetate (26.8 g, 50.47 mmol), 4-trifluoromethoxyphenyl boronic acid (52 g, 252 mmol), potassium phosphate trihydrate (80.6 g, 303 mmol), palladium acetate (1.13 g, 5 mmol), 2-Dicyclohexylphosphino-2',6'-dimethoxybiphenyl (Sphos) (3.1 g, 7.6 mmol), and toluene (1 L) were added to a three-neck flask in sequence. The reaction was refluxed under nitrogen overnight. After the reaction went to completion, it was cooled to room temperature. Water was added and the organic phase was separated. The crude product was purified by column chromatography to give desired product (36.4 g, 94% yield).

Step 4: Synthesis of 4,4"-bis(trifluoromethoxy)-5'-(4-(trifluoromethoxy)phenyl)-[1,1':3',1"-terphenyl]-2',4',6'-tricarbo xylic acid

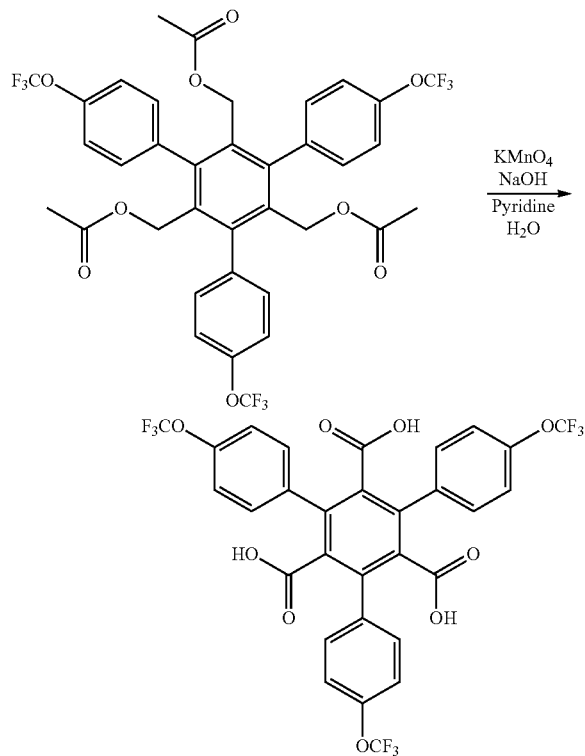

(4,4"-bis(trifluoromethoxy)-5'-(4-(trifluoromethoxy)phenyl)-[1,1':3',1"-terphenyl]-2',4',6'-tri yl)tris(methylene) triacetate (36.6 g, 47,3 mmol) was dissolved in pyridine (500 mL). Potassium permanganate (60 g, 378 mmol) in water and sodium hydroxide (15.1 g, 378 mmol) in water were added to the solution. The mixture was refluxed overnight. The reaction was cooled to room temperature. The solid was filtered off. The filtrate was acidified to afford white precipitate. The precipitate was collected by filtration and dried under vacuum to give desired product (30 g, 92% yield).

Step 5: Synthesis of 2,7,12-tris(trifluoromethoxy)-5H-diindeno [1,2-a:1',2'-c]fluorene-5,10,15 -trione

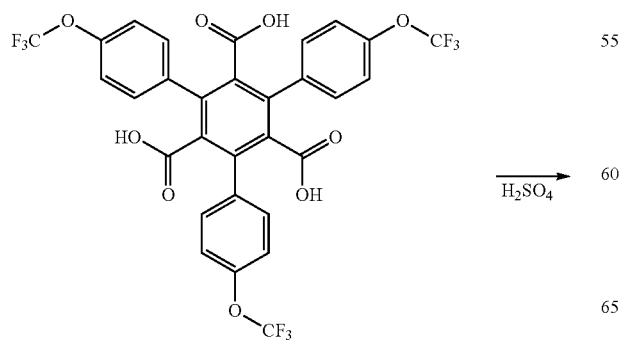

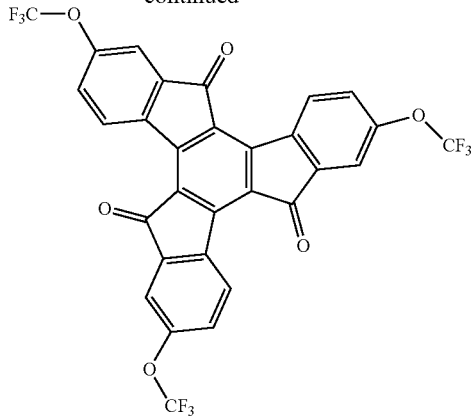

4,4"-bis(trifluoromethoxy)-5'-(4-(trifluoromethoxy)phenyl)-[1,1':3',1"-terphenyl]-2',4',6'-tricarboxylic acid (6.9 g, 10 mmol) was added to sulfuric acid (100 mL). The reaction was heated to 100° C. for 5 h. The reaction mixture was poured carefully to ice water and stirred at room temperature for 30 min. The solid was then collected by filtration to obtain desired product (4.5 g, 70% yield).

Step 6: Synthesis of Compound 9

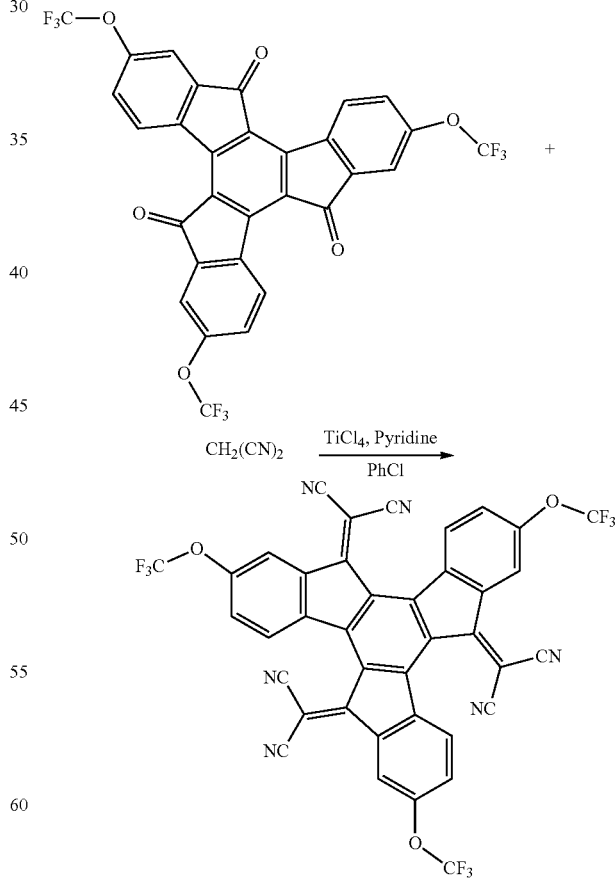

2,7,12-tris(trifluoromethoxy)-5H-diindeno[1,2-a:1',2'-c]fluorene-5,10,15-trione (6 g, 9.43 mmol) was dispersed in anhydrous chlorobenzene (500 mL), malononitrile (6.2 g, 94.3 mmol) was added under nitrogen. To the mixture as added titanium tetrachloride (35.8 g, 189 mmol) and anhydrous pyridine (29.8 g, 377 mmol) sequentially. The reaction mixture was refluxed for 29 h. After cooled to room temperature, water was added. The organic phase was extracted with dichloromethane and the crude product was further purified by column chromatography and recrystallization from chlorobenzene. The structure of the compound was confirmed by NMR and MALDI-TOF. 1H NMR (CDCl3, 400 MHz): δ (ppm)=9.21 (d, 3H), 7.64 (s, 3H), 7.53 (d, 3H). The compound has a molecular weight of 780, identified as the target product.

The persons skilled in the art should know that the above preparation method is only an illustrative example, and the persons skilled in the art can obtain the structure of other compounds of the present invention by modifying the above preparation method.

Device Examples:

A glass substrate with 80 nm thick indium-tin-oxide (ITO) anode was first cleaned and then treated with oxygen plasma and UV ozone. After the treatments, the substrate was baked dry in a glovebox to remove moisture. The substrate was then mounted on a substrate holder and loaded into a vacuum chamber. The organic layers specified below were deposited in sequence by thermal vacuum deposition on the ITO anode at a rate of 0.2-2 Å/s at a vacuum of around $10^{-8}$ torr. 3% of Compound 9 doped in Compound HT was used as the hole injection layer (HIL). Compound HT was used as the hole transporting layer (HTL). Then Compound YD was doped in the hosts Compound H1 and Compound H2 as the emitting layer (EML). On the emitting layer, Compound H2 was used as the hole blocking layer (HBL). A mixture of Compound ET and 8-hydroxyquinolinolato-lithium (Liq) was deposited as the electron transporting layer (ETL). Finally, 10 Å-thick Liq was deposited as the electron injection layer and 1000 Å of Al was deposited as the cathode. The device was then transferred back to the glovebox and encapsulated with a glass lid and a moisture getter to complete the device. The comparative example was made the same way except that Compound 9 was replaced by Compound A.

The detailed device layer structure and thicknesses are shown in the table below. When more than one kind of materials are used in one layer, they are obtained by doping different compounds in their weight ratios.

The structures of the materials used in the devices are shown below:

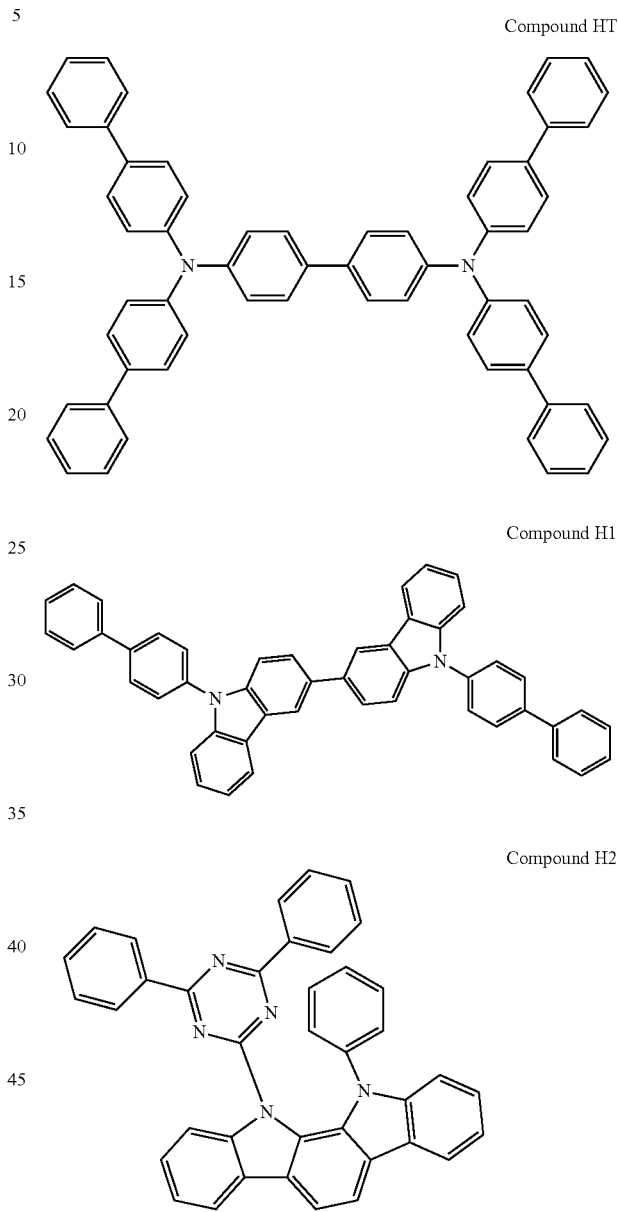

Compound HT

Compound H1

Compound H2

TABLE 1

| Device structure of device examples | | | | | |
|---|---|---|---|---|---|
| Device ID | HIL | HTL | EML | HBL | ETL |
| Example 1 | Compound HT:Compound 9 (97:3) (100 Å) | Compound HT (400 Å) | Compound H1:Compound H2:Compound YD (45:45:10) (400 Å) | Compound H2 (100 Å) | Compound ET:Liq (35:65) (350 Å) |
| Comparative Example 1 | Compound HT:Compound A (97:3) (100 Å) | Compound HT (400 Å) | Compound H1:Compound H2:Compound YD (45:45:10) (400 Å) | Compound H2 (100 Å) | Compound ET:Liq (35:65) (350 Å) |

Compound YD

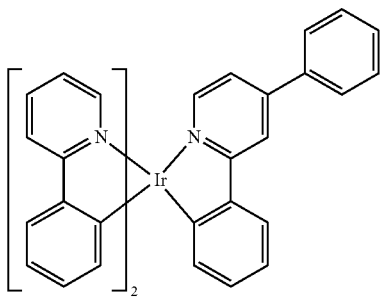

Compound ET

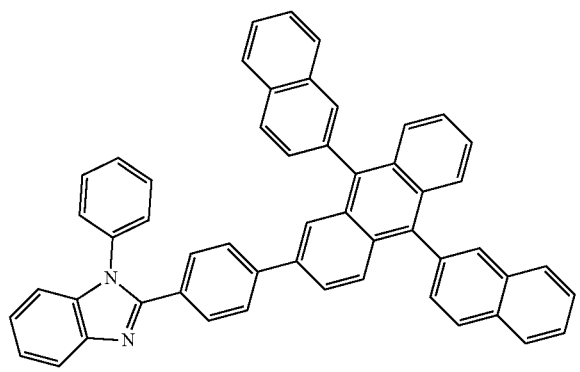

Compound 9

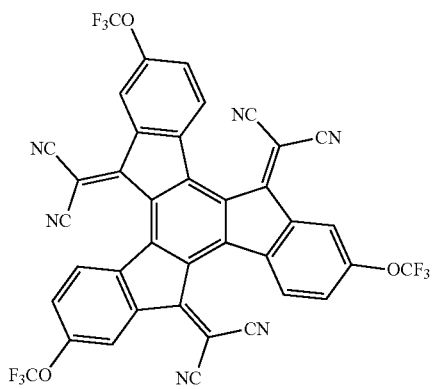

Compound A

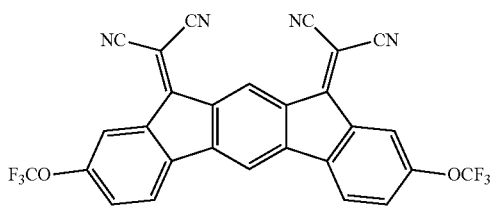

The IVL and lifetime characteristics of the devices were measured at various current densities and voltages. The luminance efficiency (LE), external quantum efficiency (EQE), λ max, full width at half maximum (FWHM), voltage (V) and CIE data were measured at 1000 nits. The lifetime was tested at a constant current from an initial brightness of 21,750 nits.

TABLE 2

| | | | | Device data | | | |
|---|---|---|---|---|---|---|---|
| Device ID | CIE (x, y) | λmax (nm) | FWHM (nm) | Voltage (V) | LE (cd/A) | EQE (%) | LT97 (h) |
| Example 1 | (0.43, 0.55) | 554 | 81 | 4.25 | 79.65 | 23.26 | 139 |
| Comparative Example 1 | (0.43, 0.55) | 554 | 81 | 5.07 | 51.25 | 14.91 | 29 |

Discussion:

From the device data in table 2, both devices showed yellow emission color from Compound YD. However, the inventive compound showed advantages over the comparative compound in various aspect. For example, the inventive example had much lower driving voltage than the comparative example, 4.25 V vs. 5.07 V, indicating the hole injection using the inventive compound is much more efficient than the comparative compound. The inventive example also had high LE, EQE and longer device lifetime than the comparative example.

It is understood that the various embodiments described herein are by way of example only and are not intended to limit the scope of the invention. The present invention as claimed may therefore include variations from the particular examples and preferred embodiments described herein, as will be apparent to one of skill in the art. Many of the materials and structures described herein may be substituted with other materials and structures without deviating from the spirit of the invention. It is understood that various theories as to why the invention works are not intended to be limiting.

What is claimed is:

1. An organic electroluminescent device comprising:
   an anode,
   a cathode, and
   a hole injection layer disposed between the anode and cathode, wherein the hole injection layer comprises a compound selected from the group consisting of:

Compound 8

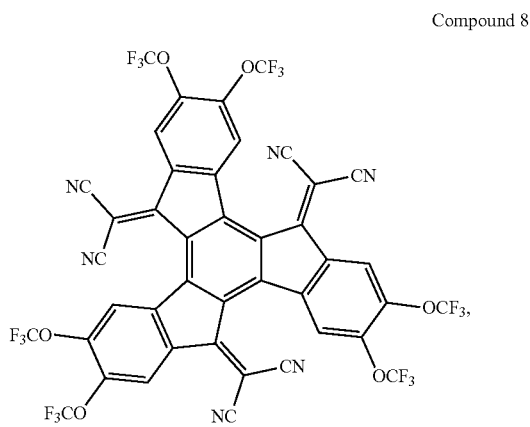

-continued
Compound 9
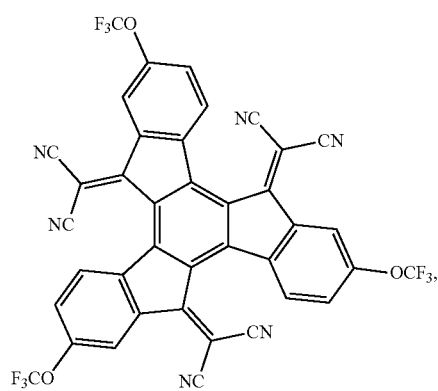
Compound 10
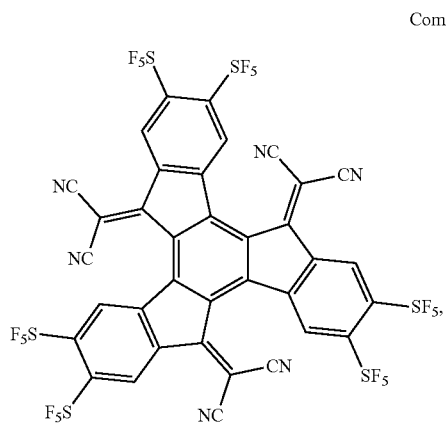
Compound 11
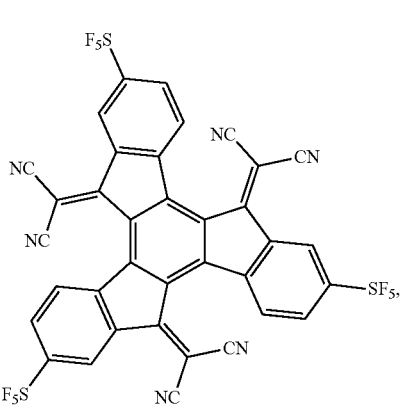
Compound 12
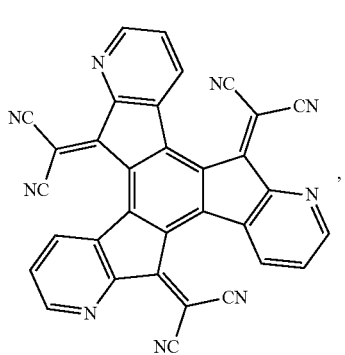
Compound 13
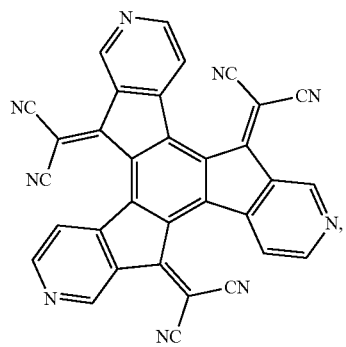
Compound 14
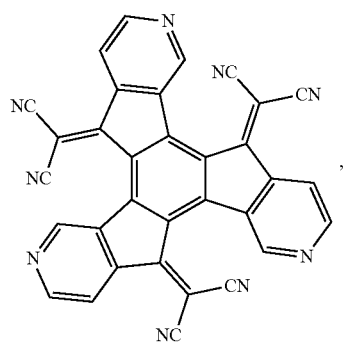
Compound 15
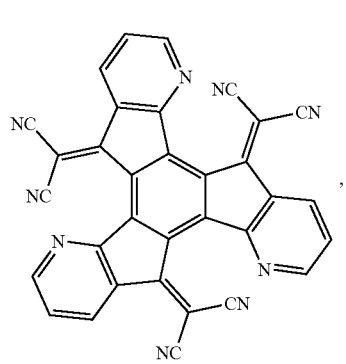
Compound 16
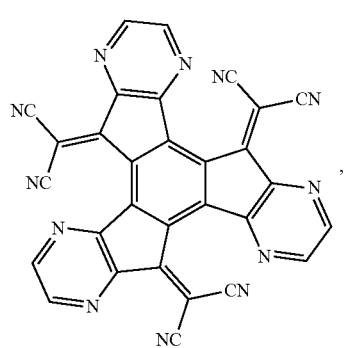

Compound 17

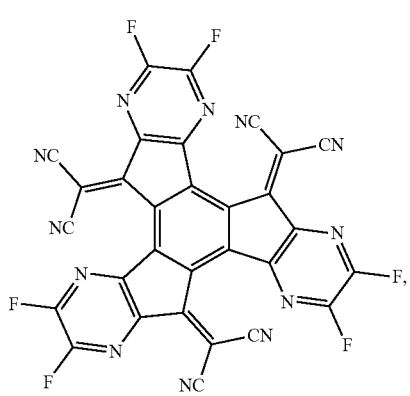

Compound 18

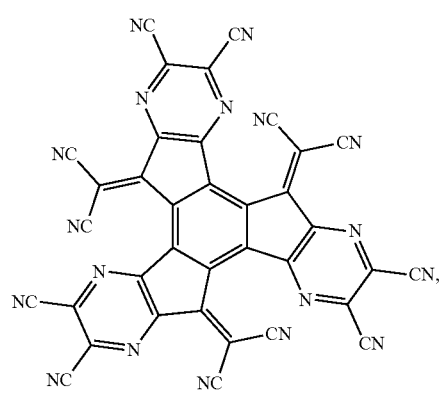

Compound 19

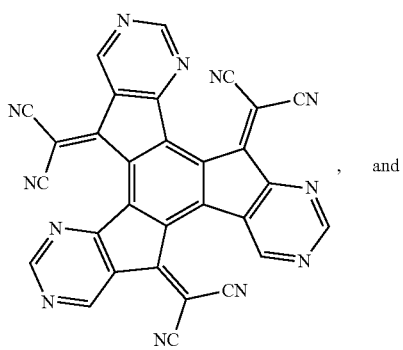

, and

Compound 20

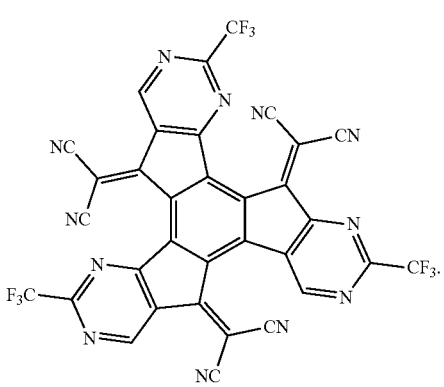

2. The device of claim 1, wherein the hole injection layer comprising the compound is in contact with the anode.

3. The device of claim 1, wherein the hole injecting layer is a layer consisting entirely of the compound.

4. The device of claim 1, wherein the hole injection layer further comprises an aromatic amine compound, and wherein the aromatic amine compound is doped with the compound.

5. The device of claim 4, wherein the aromatic amine compound is selected from the group consisting of:

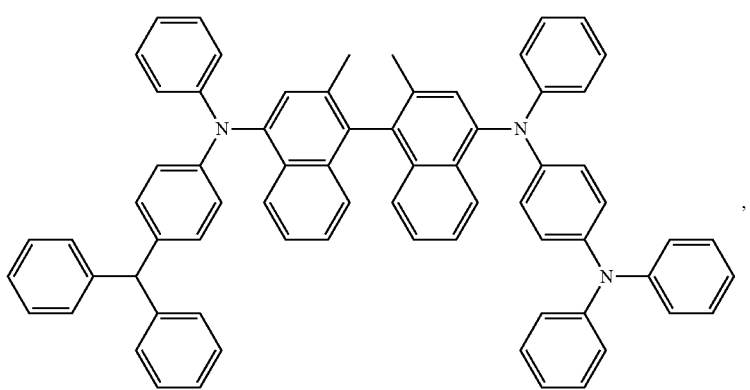

-continued
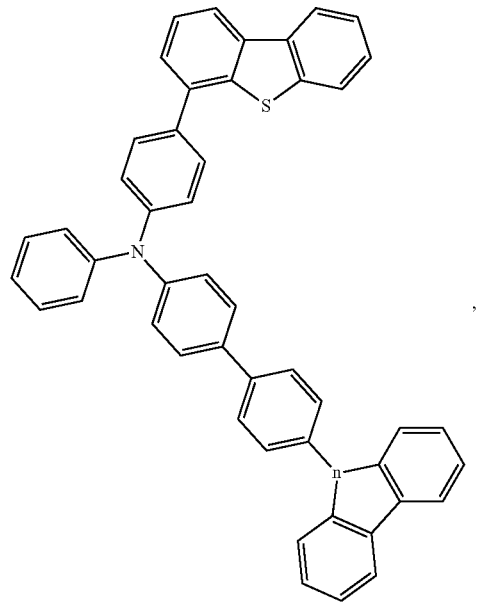
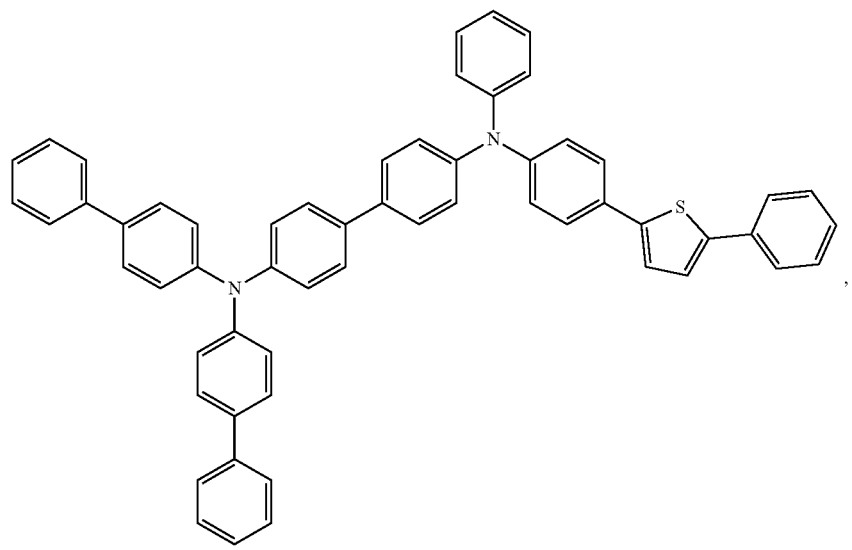
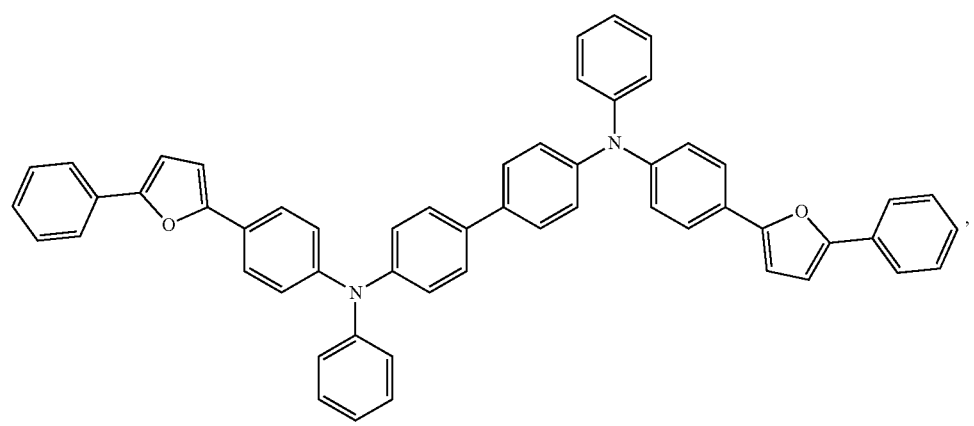

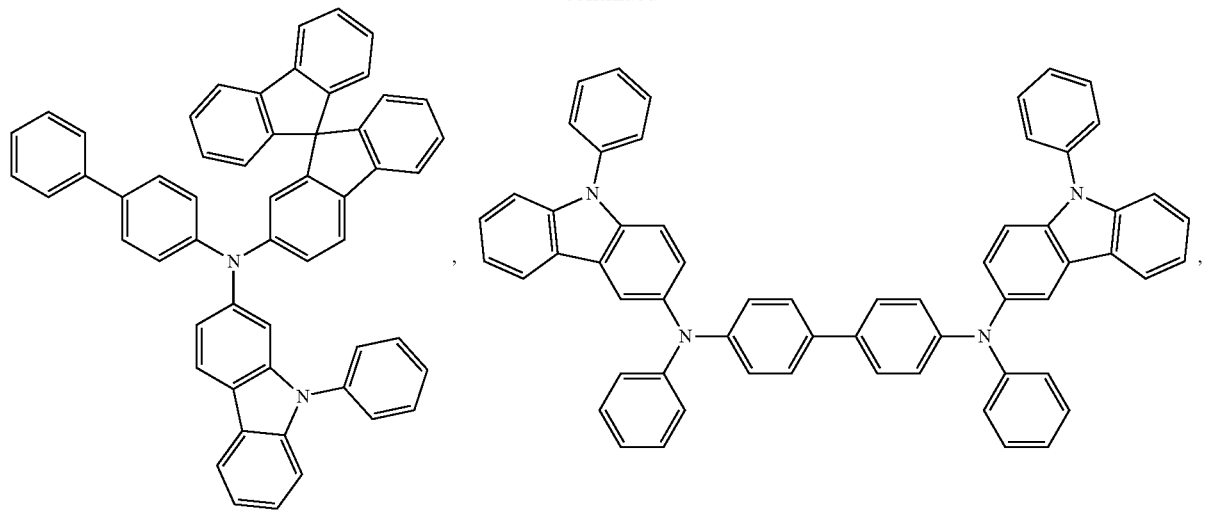
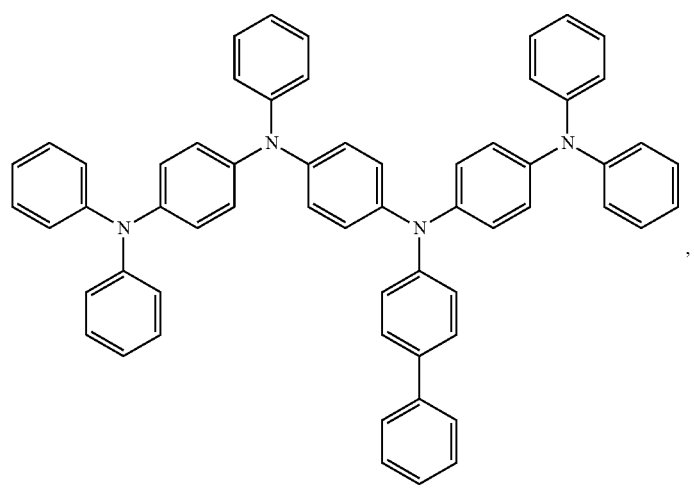
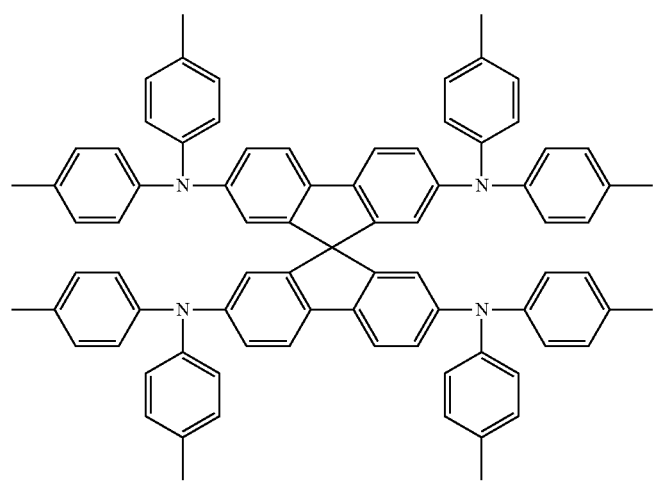

-continued
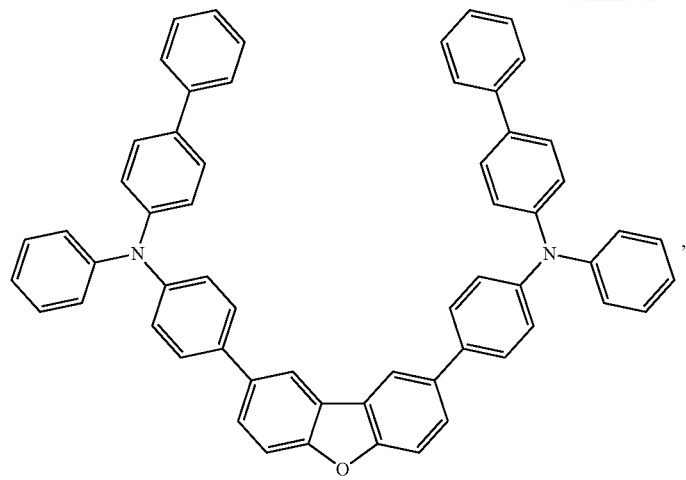
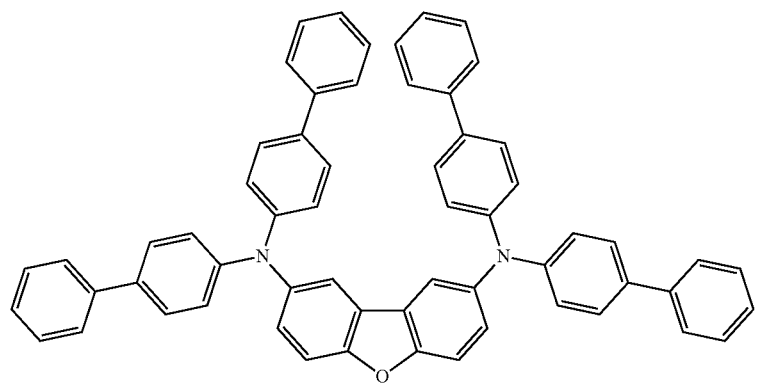
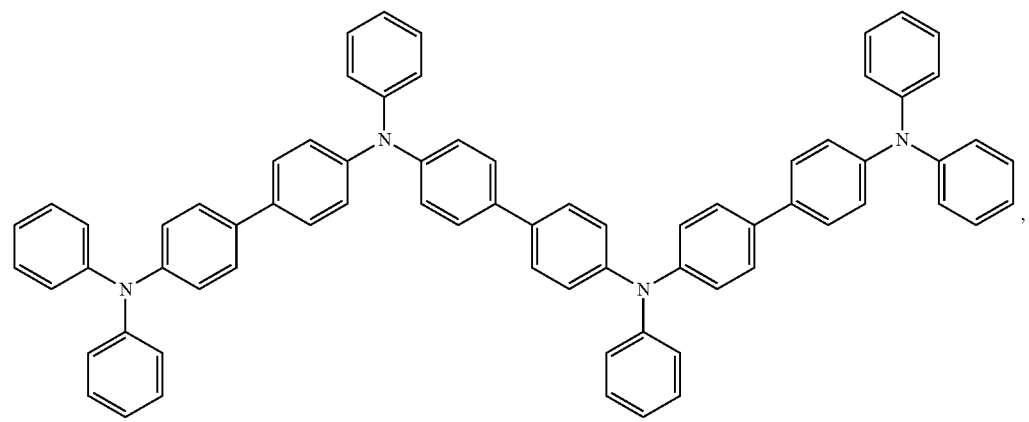

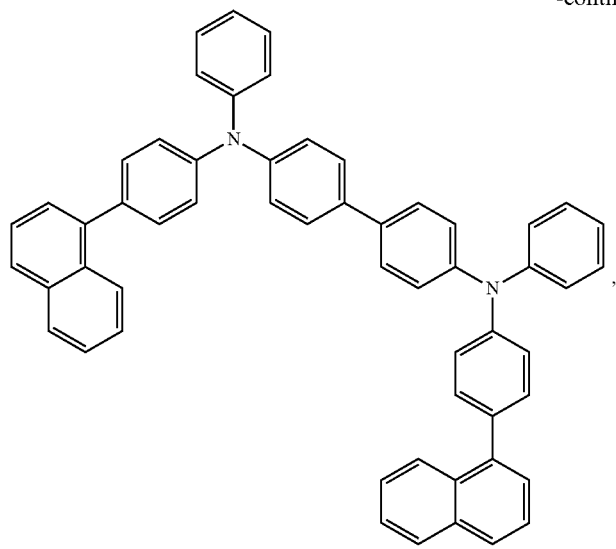
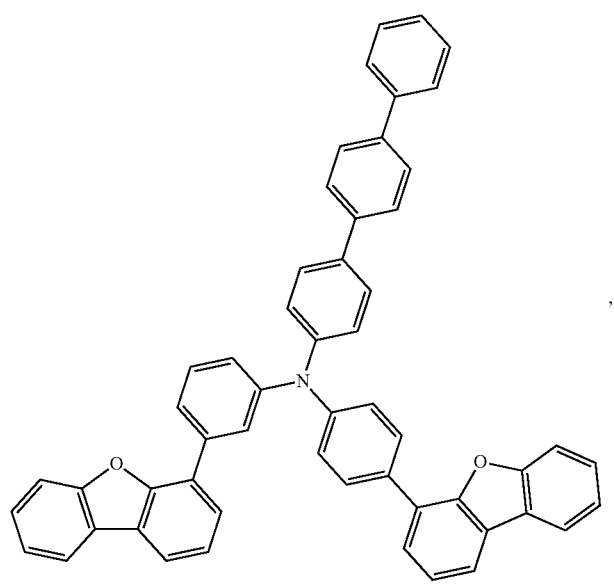
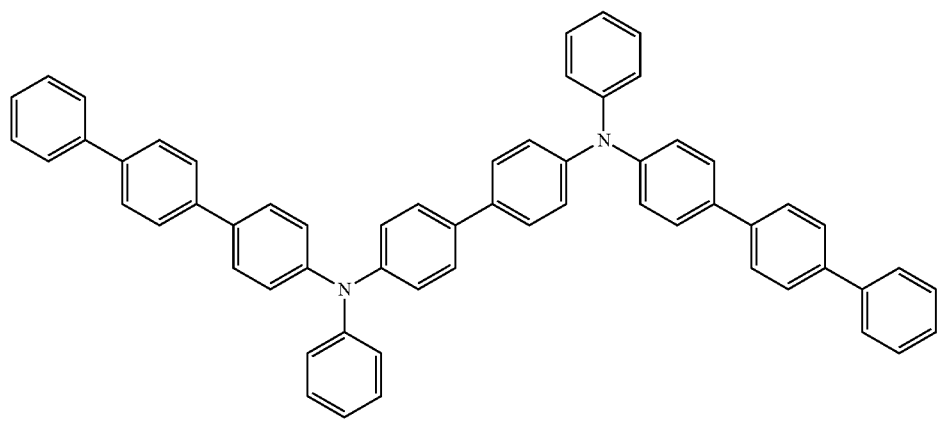

-continued
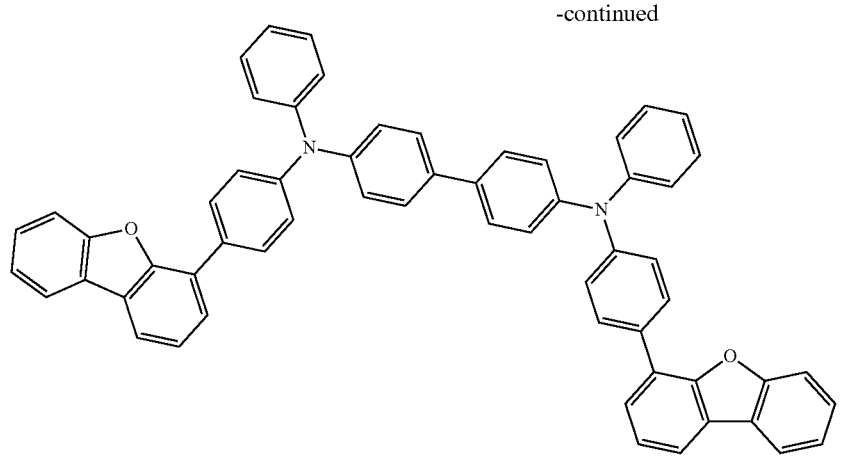
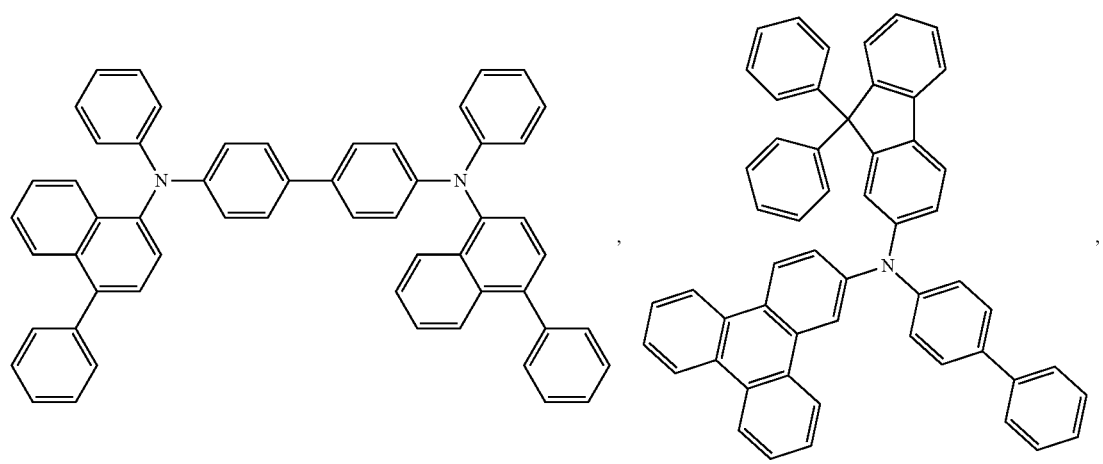
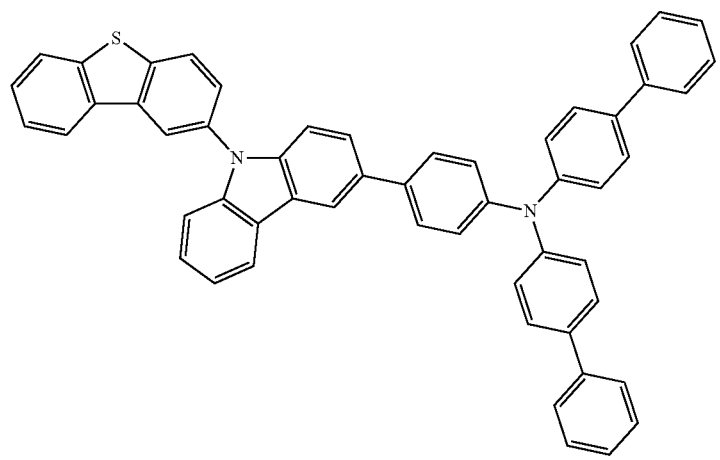

87
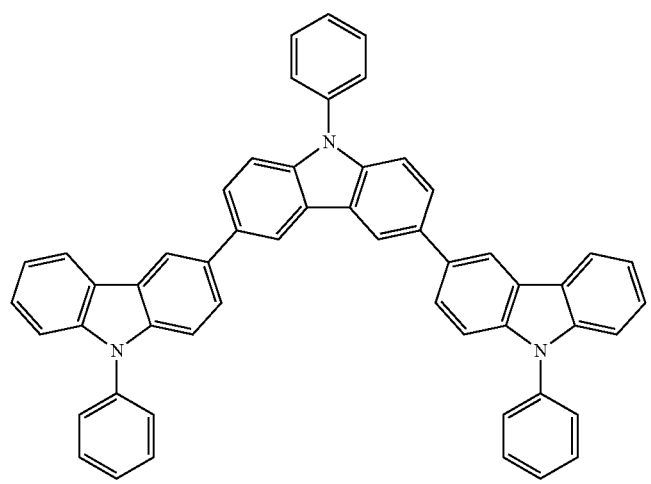
,
88
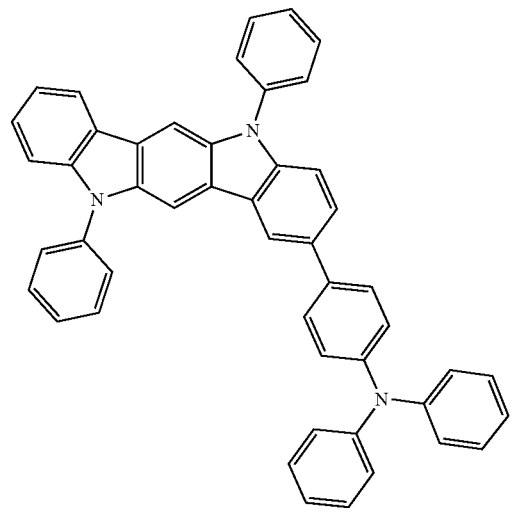
,
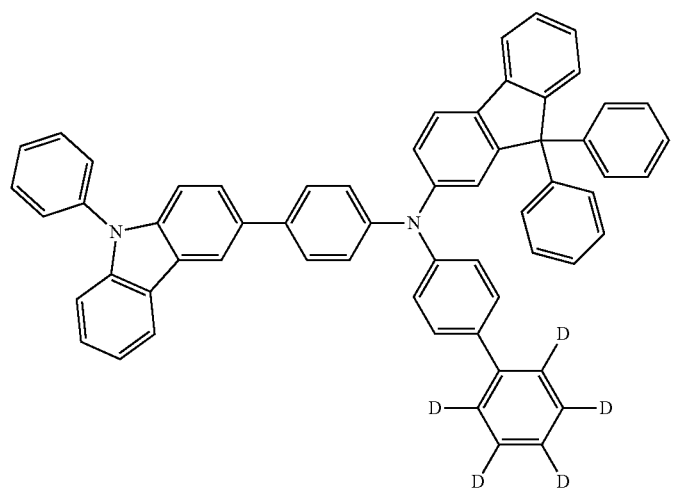
,
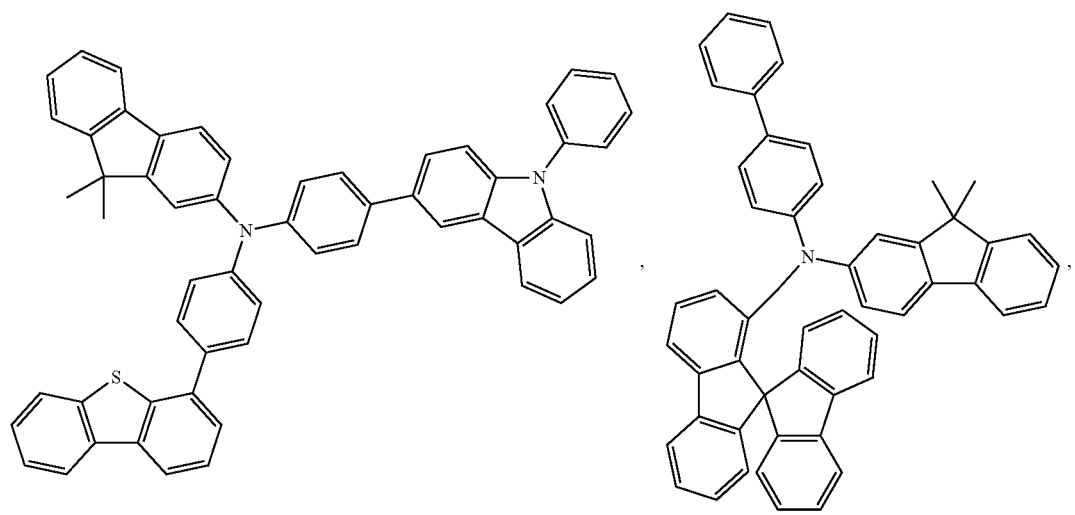

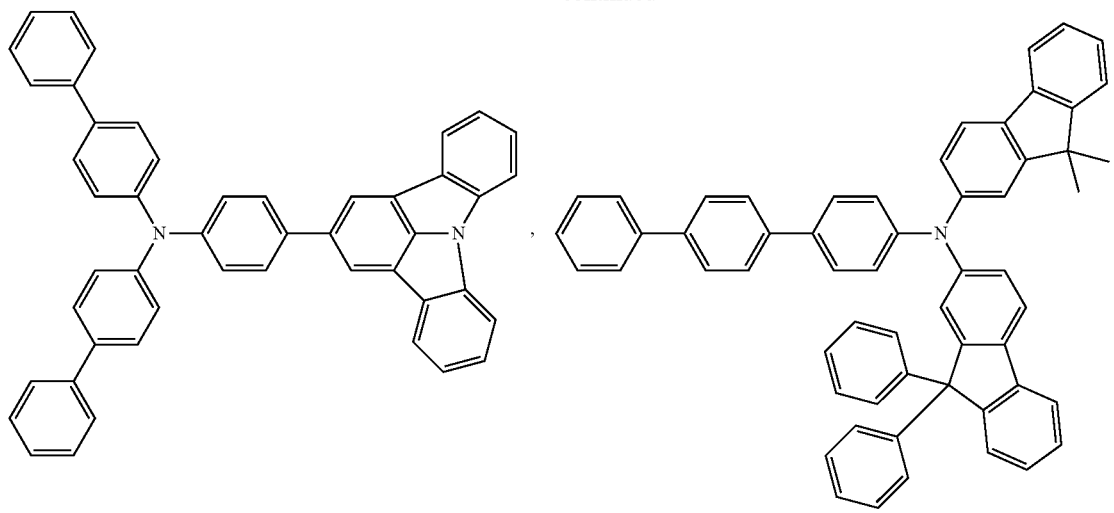
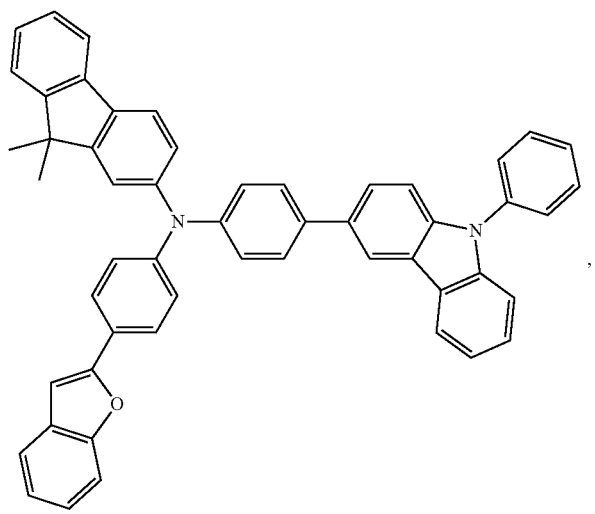
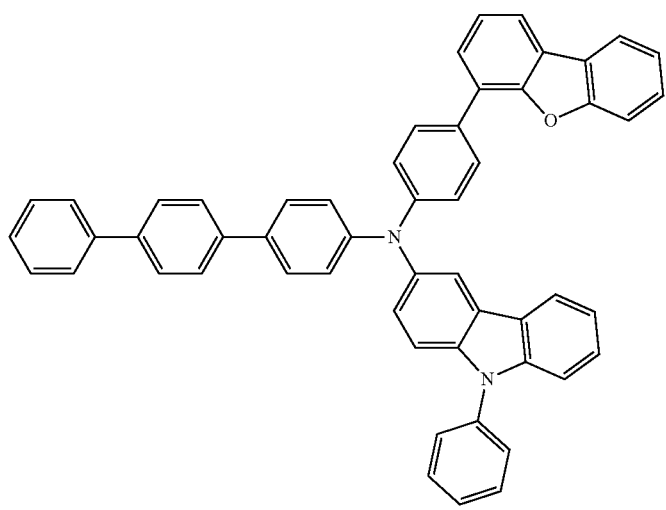

-continued
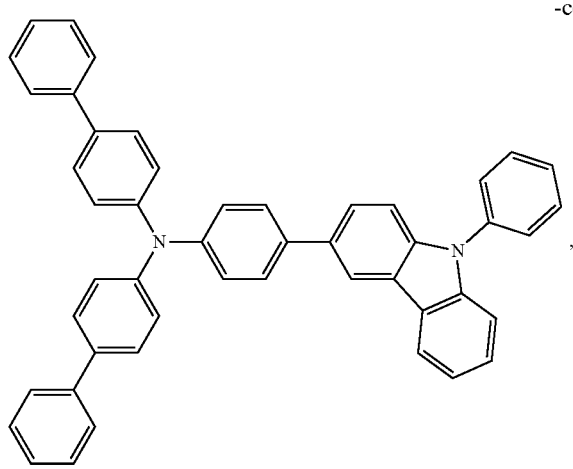
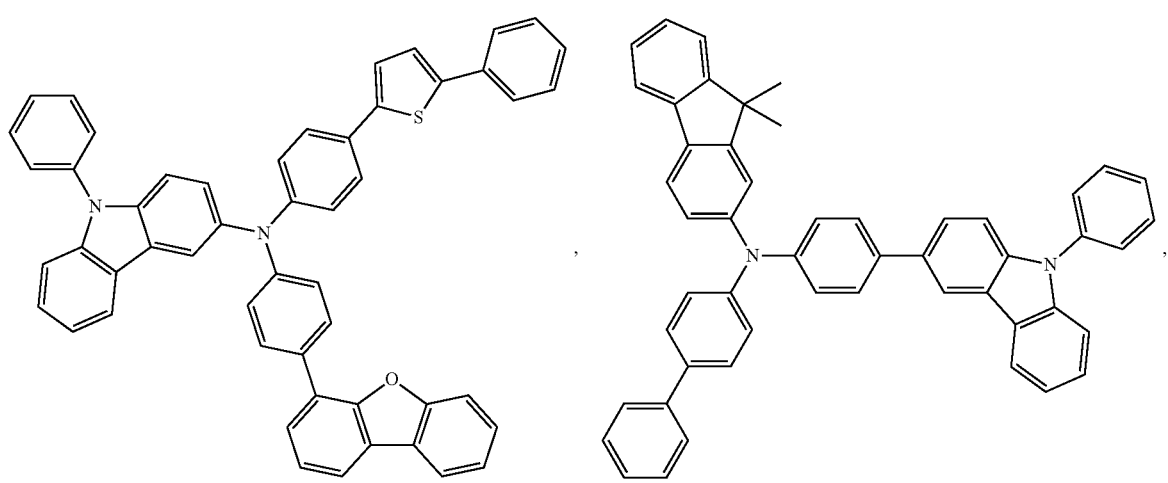
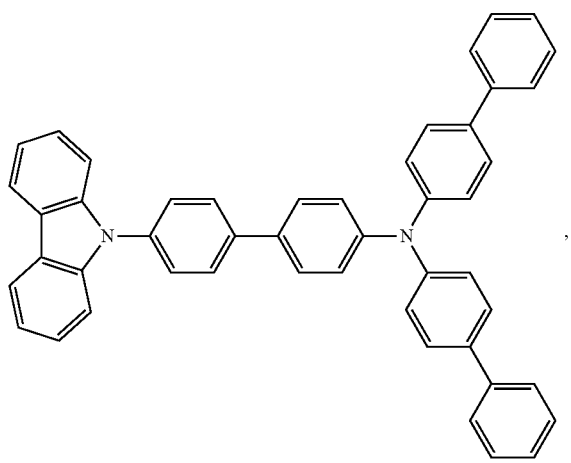

-continued
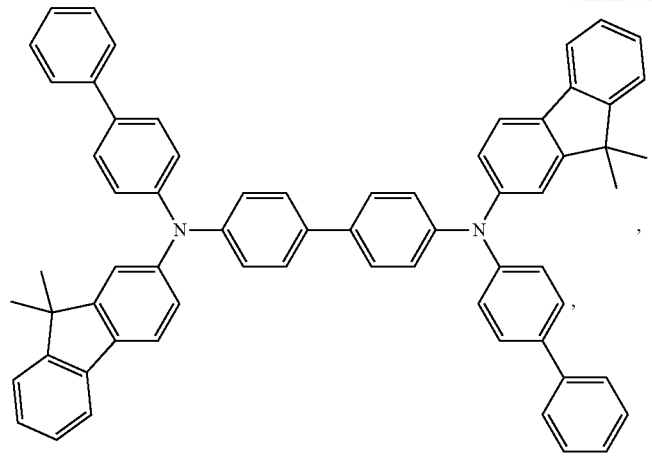
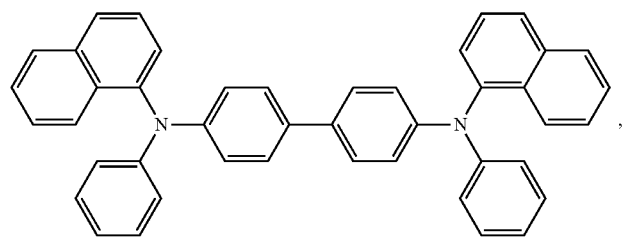
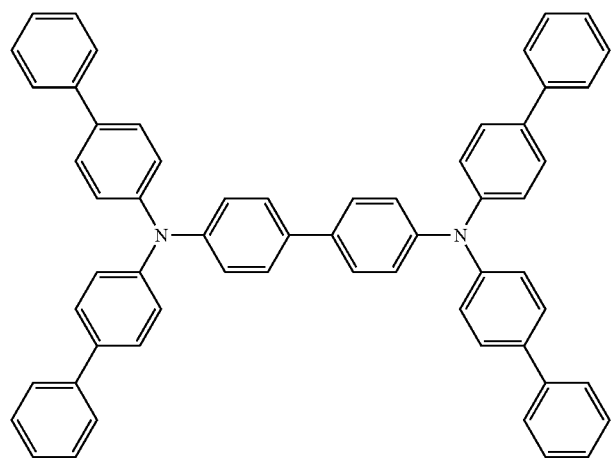
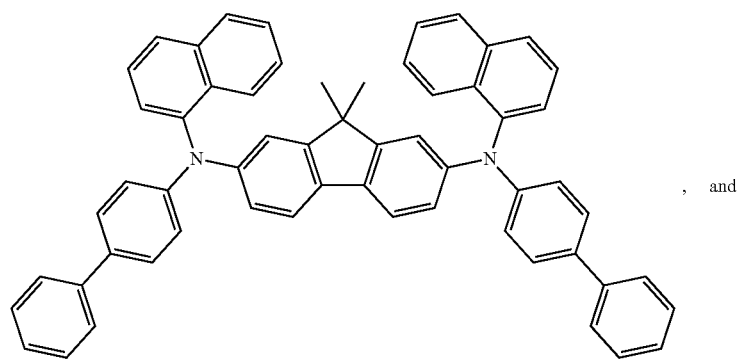
and

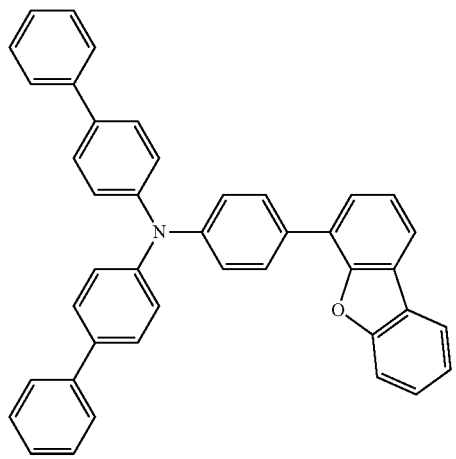
6. A tandem organic electroluminescent device comprises:
an anode,
a cathode,
a charge generation layer disposed between the anode and cathode, wherein the charge generation layer comprises a compound selected from the group consisting of:
Compound 8
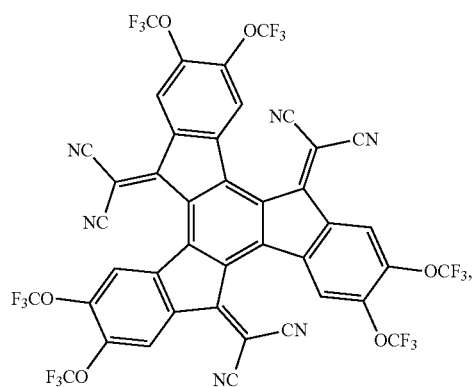
Compound 9
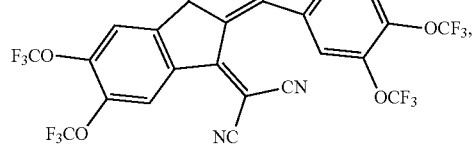
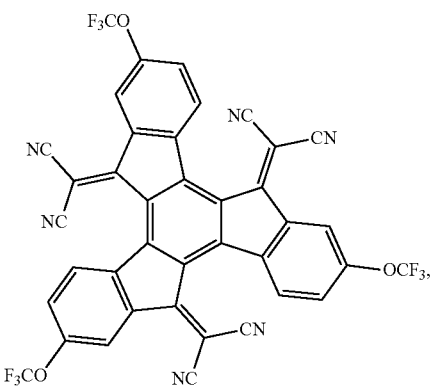
Compound 10
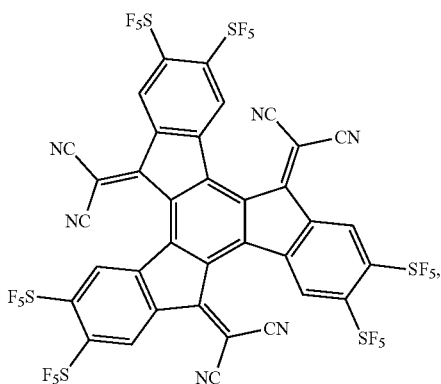
Compound 11
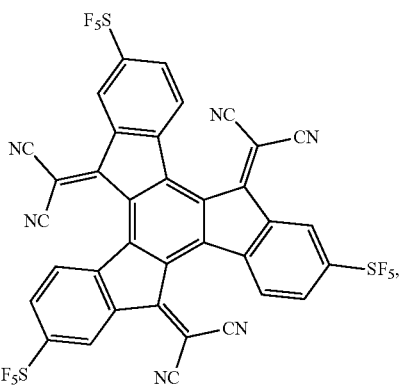
Compound 12
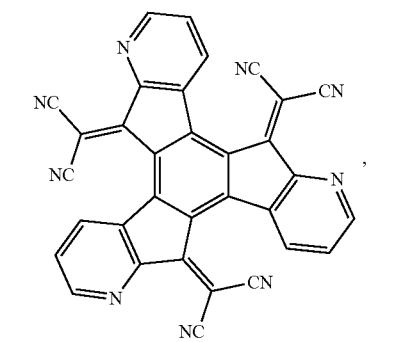

Compound 13
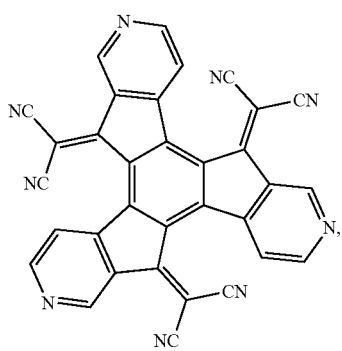
Compound 14
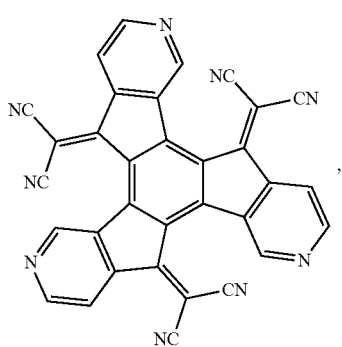
Compound 15
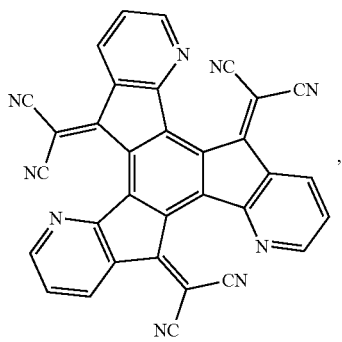
Compound 16
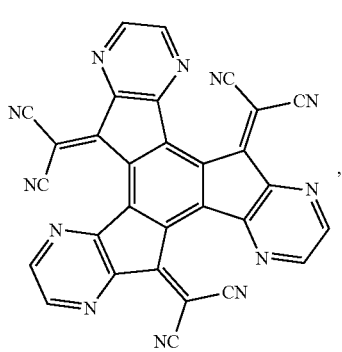
Compound 17
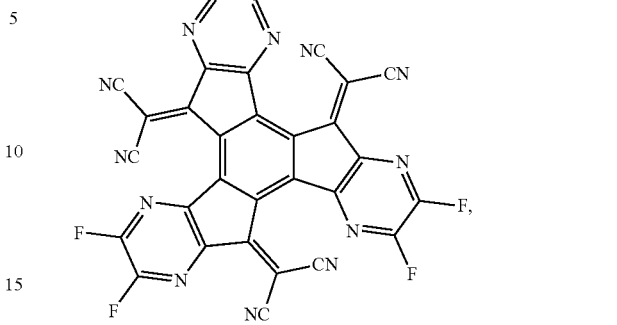
Compound 18
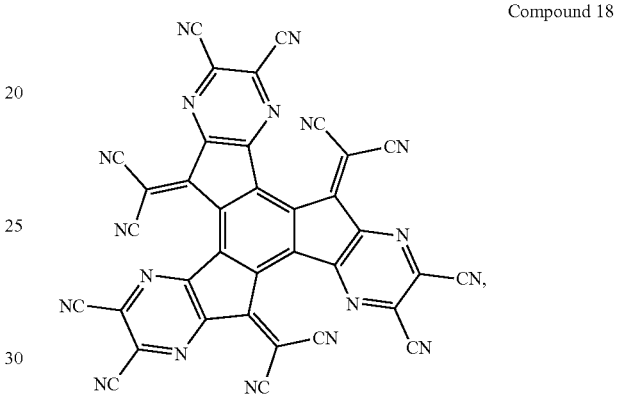
Compound 19
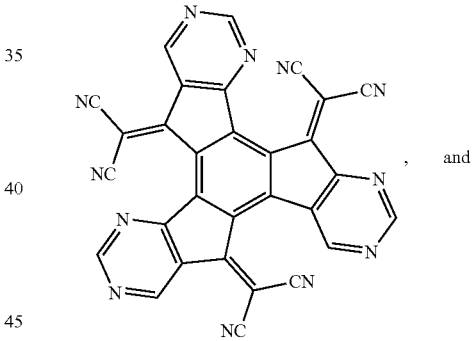
and
Compound 20
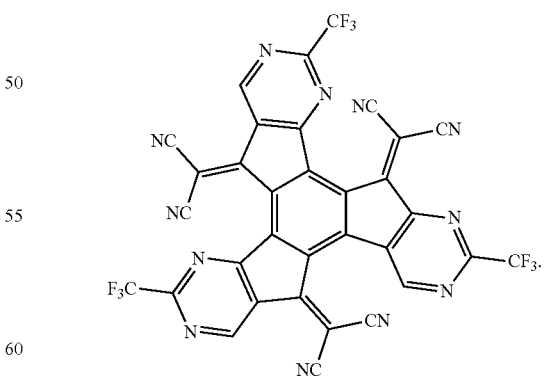
7. The device of claim 6, wherein the charge generation layer is a layer consisting entirely of the compound.
8. The device of claim 6, wherein the charge generation layer is a P-type charge generation layer.

9. The device of claim 6, wherein the charge generation layer further comprises an aromatic amine compound.
10. The device of claim 9, wherein the aromatic amine compound is selected from the group consisting of:
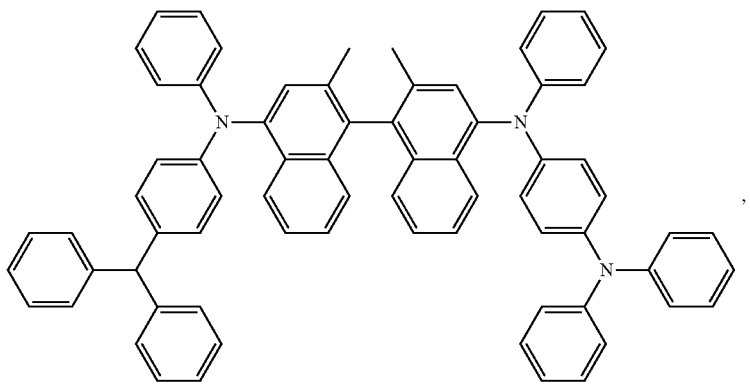
,
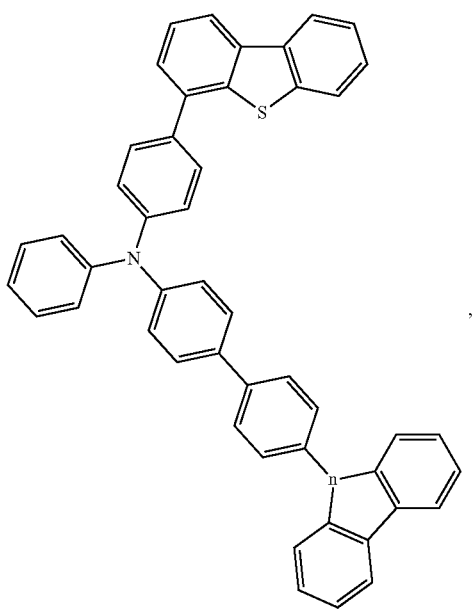
,
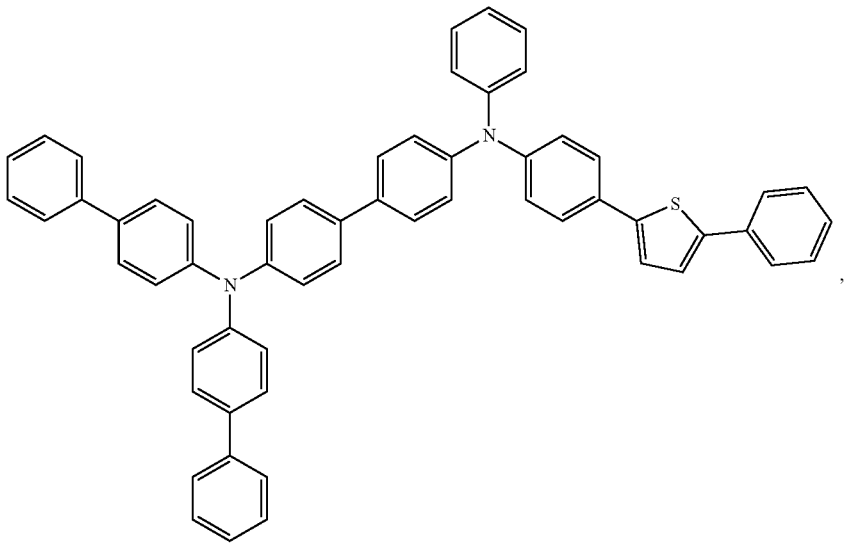
, 101
102
-continued
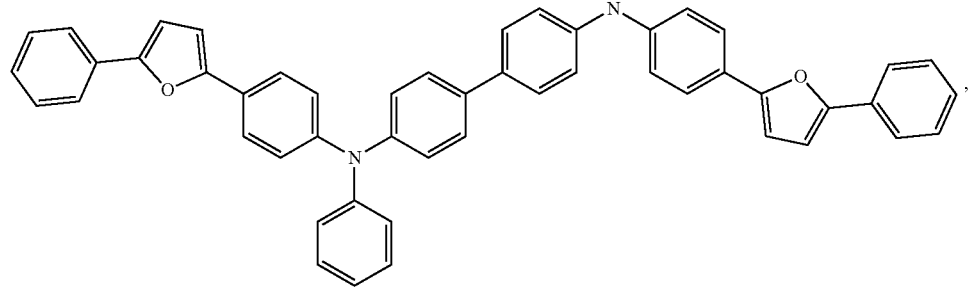
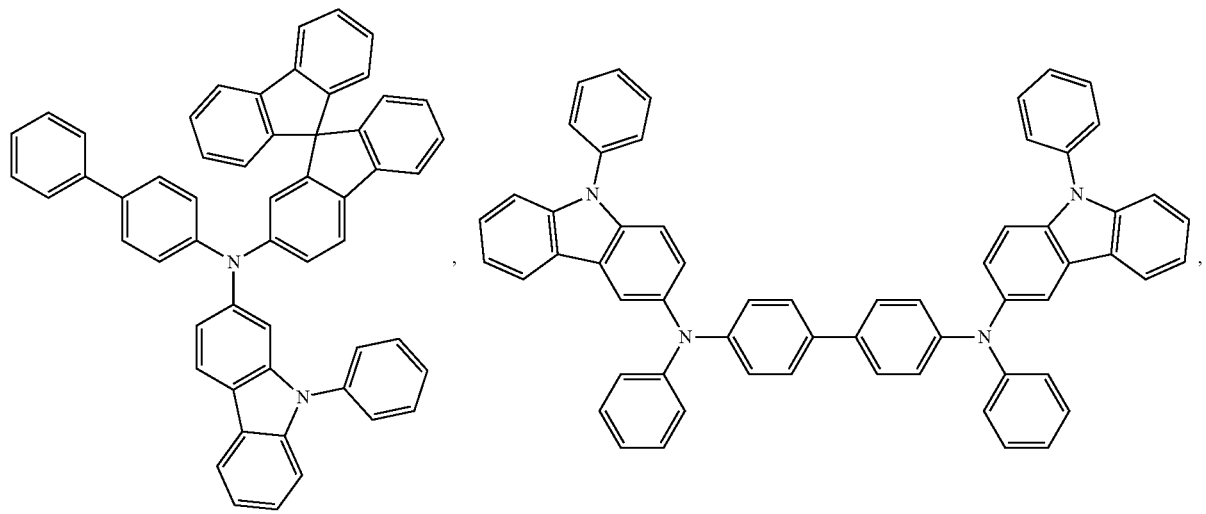
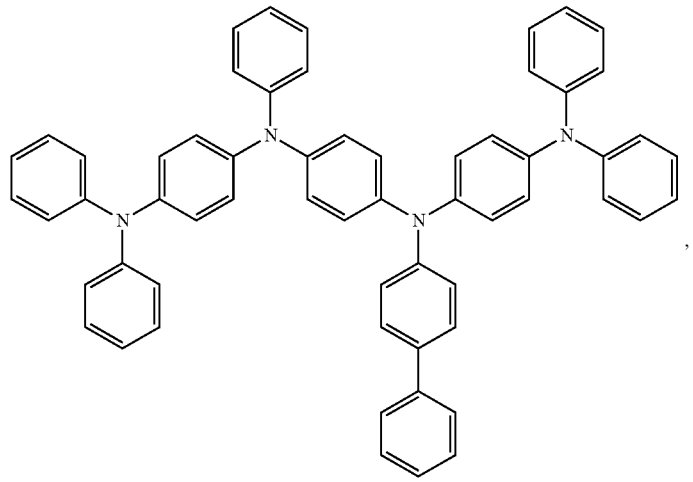

-continued
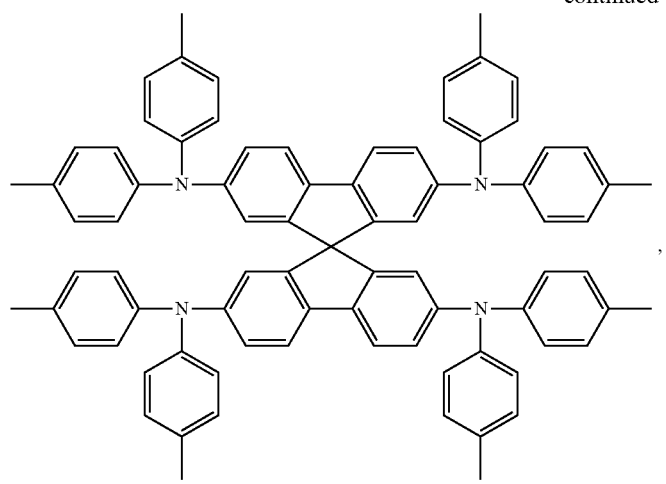
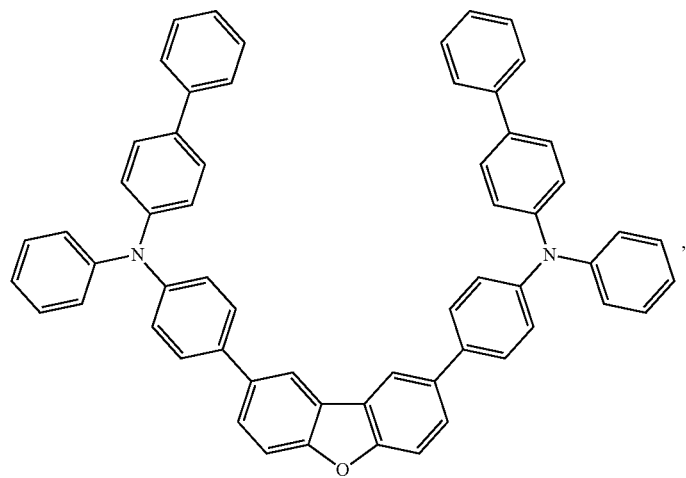
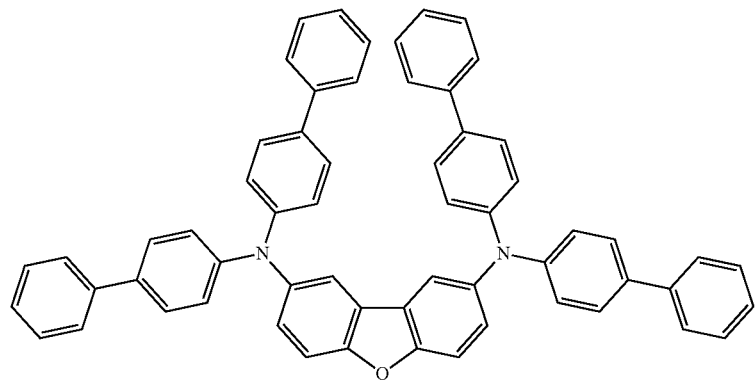

105 106
-continued
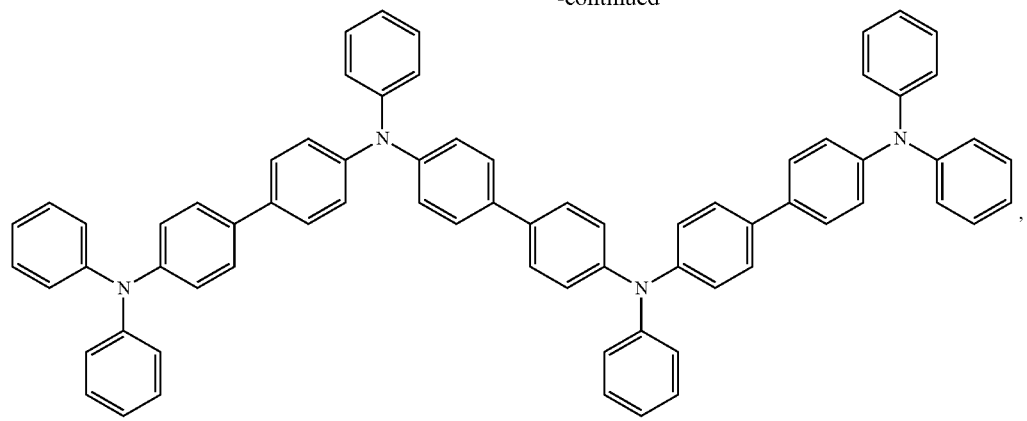
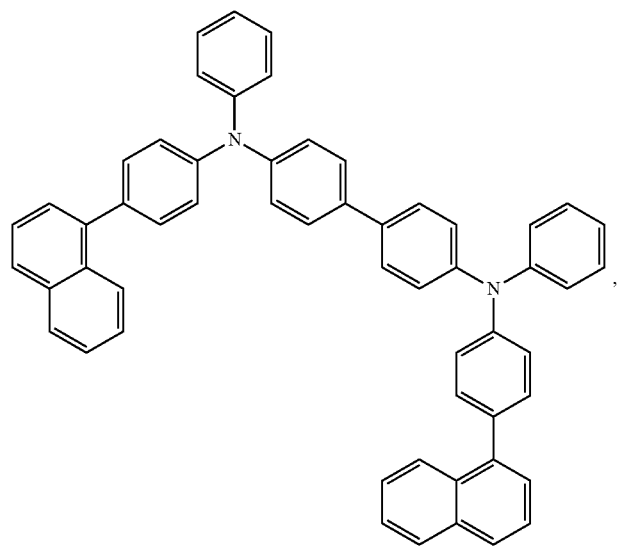
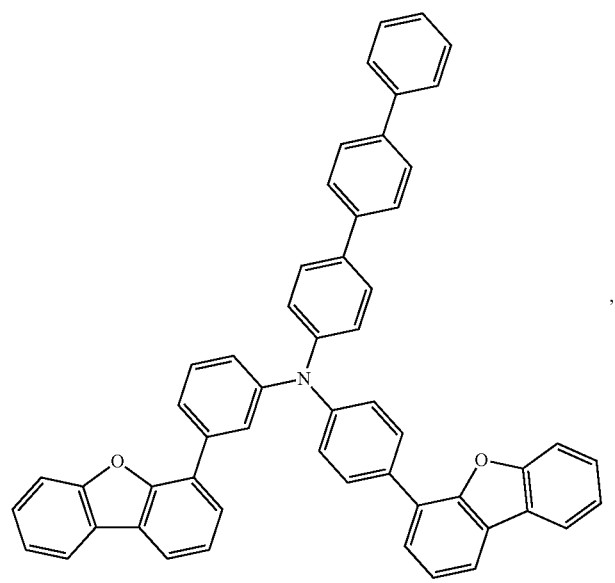

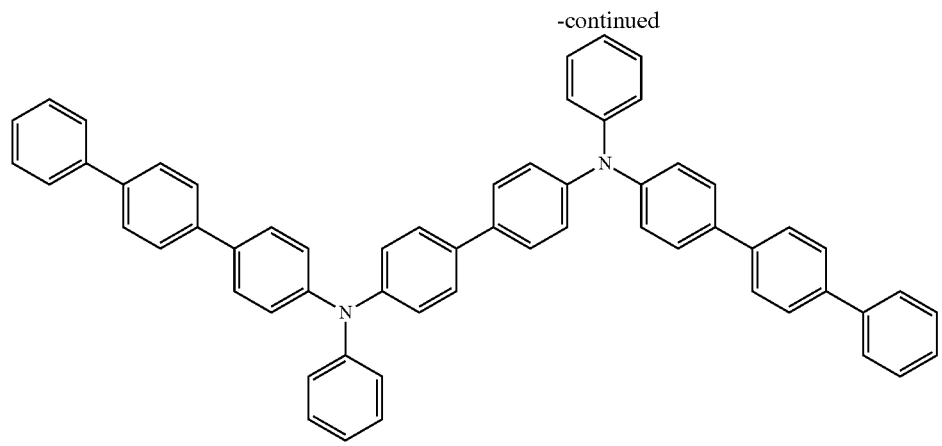
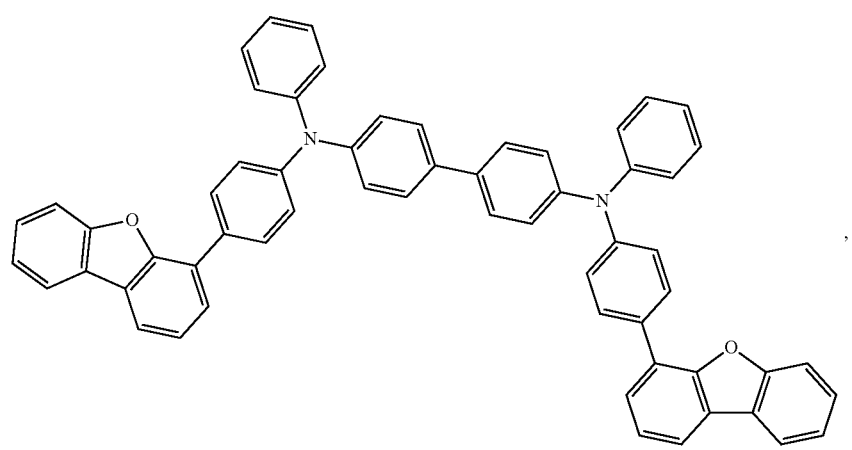
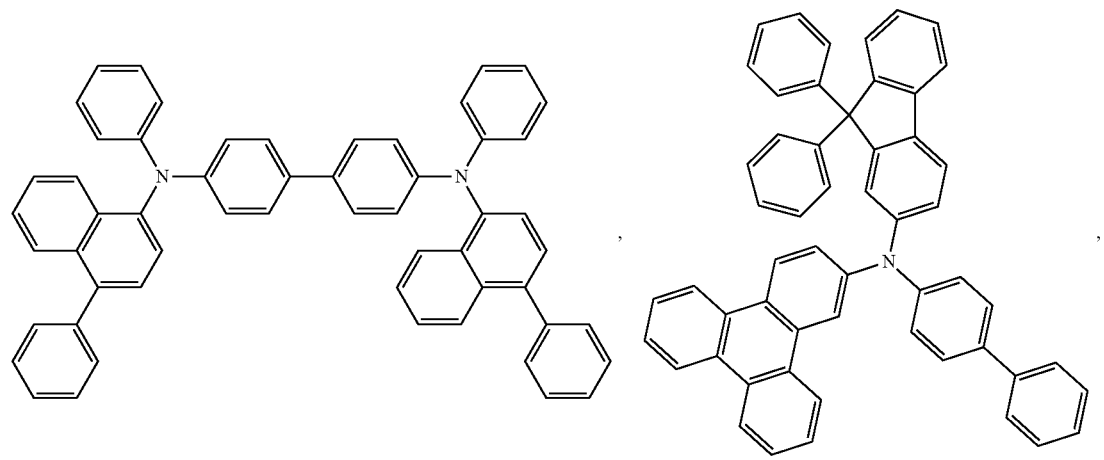

-continued
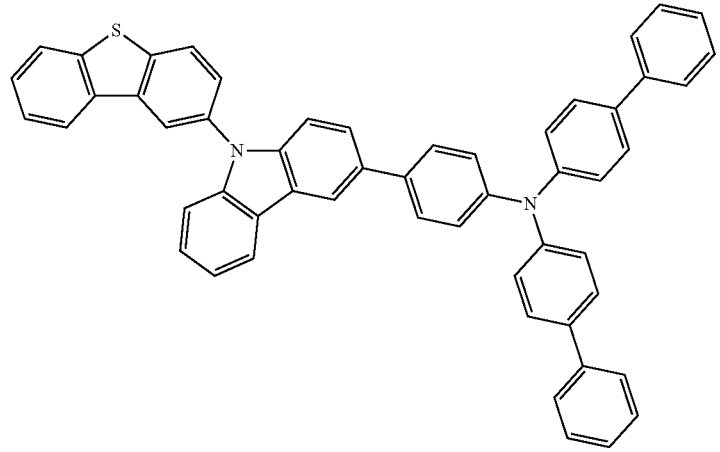
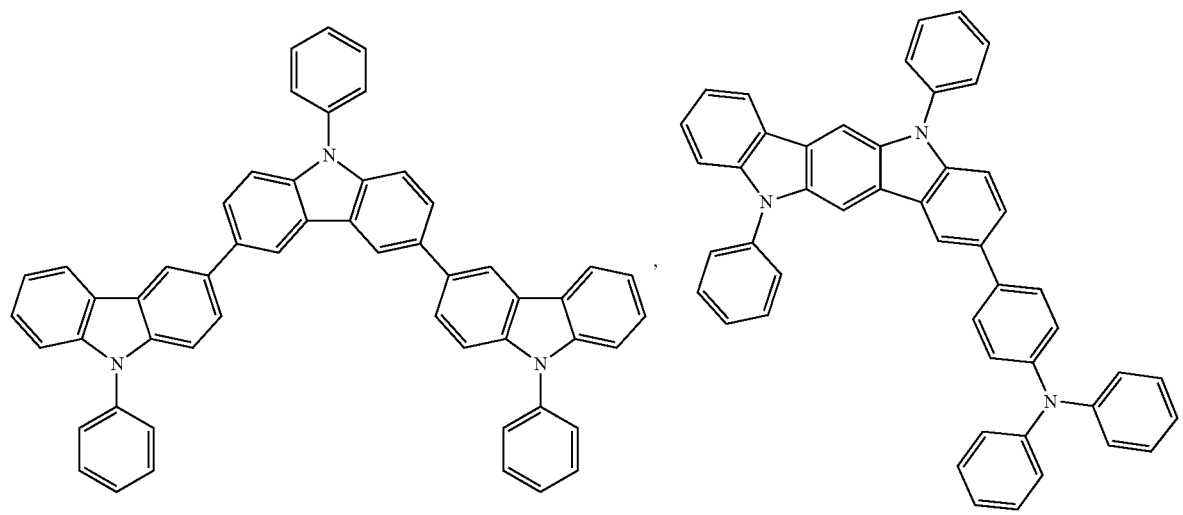
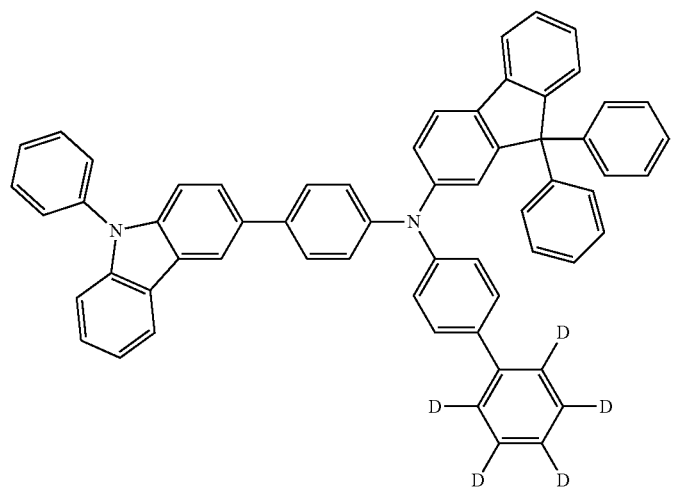

111 112
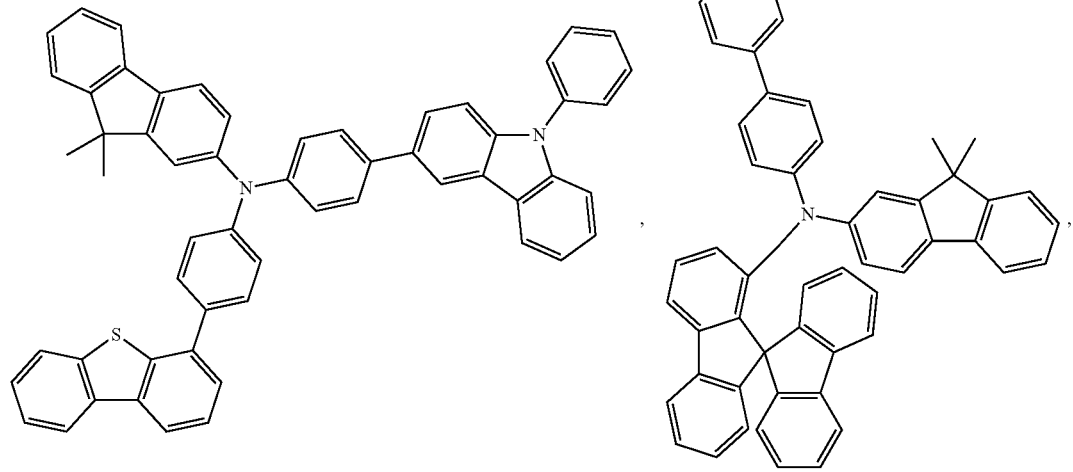
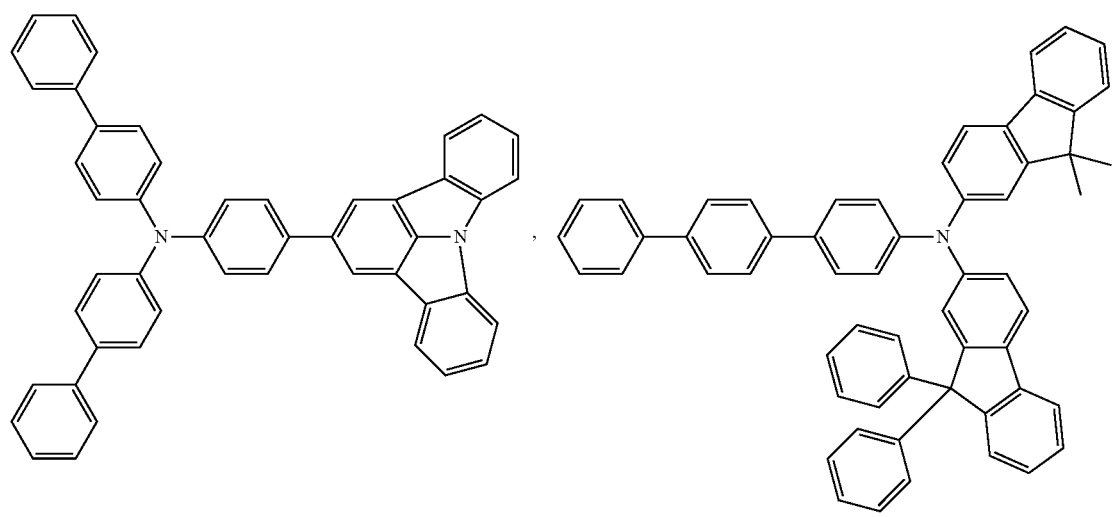
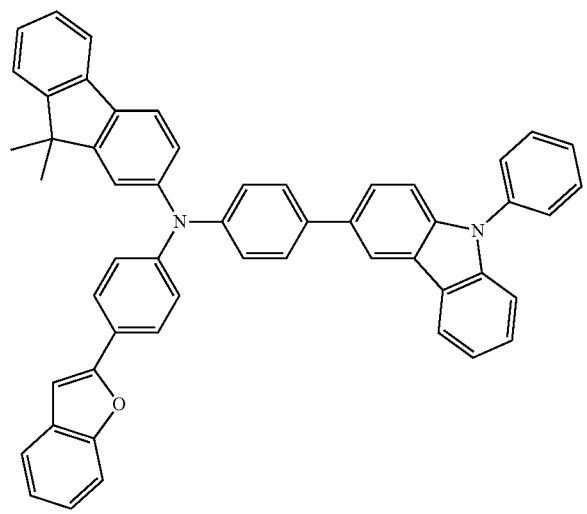

-continued
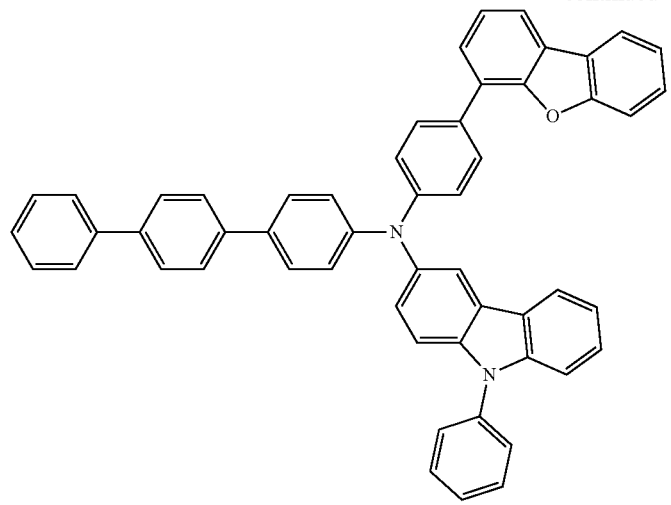
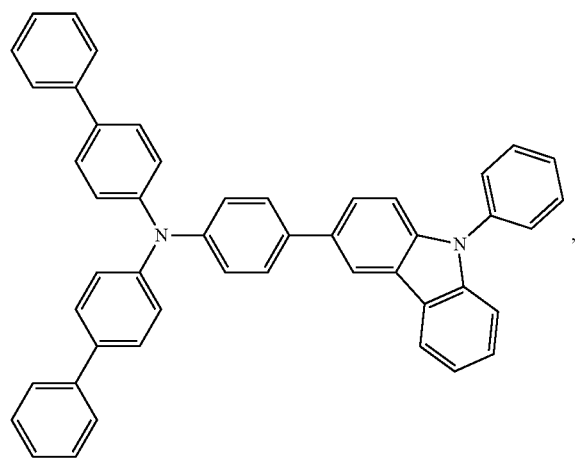
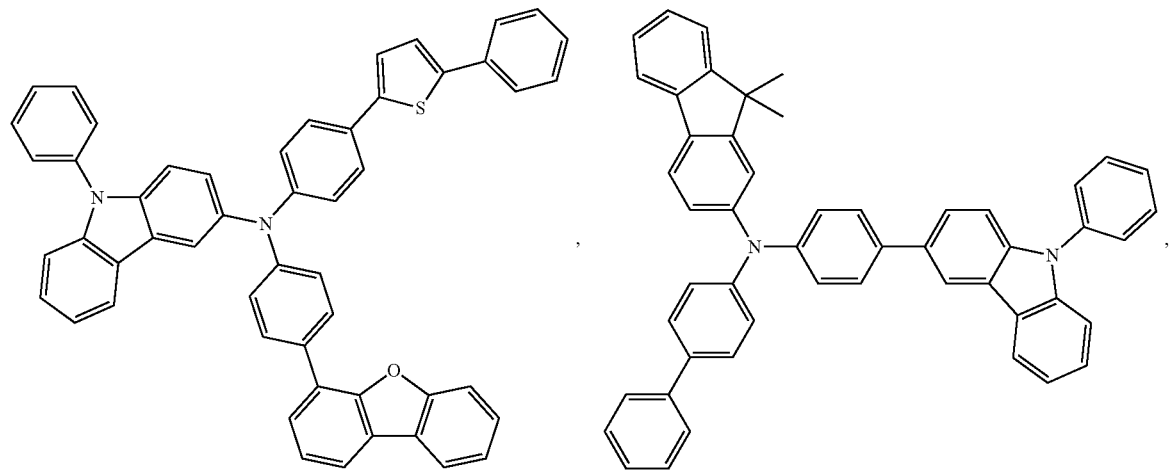

-continued
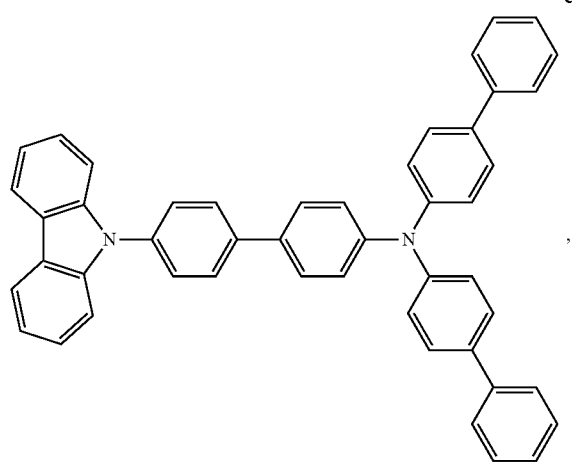
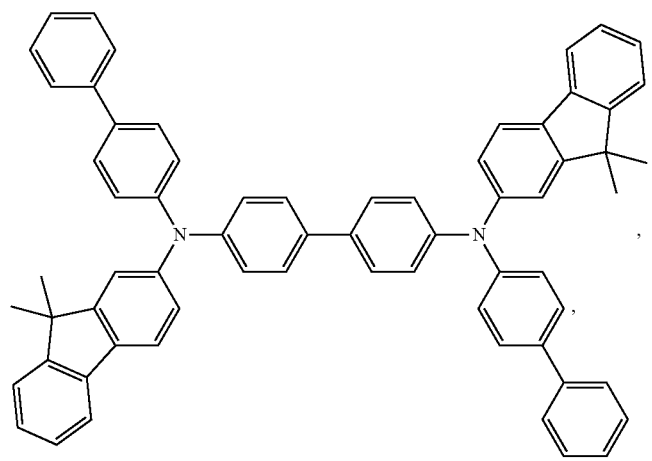
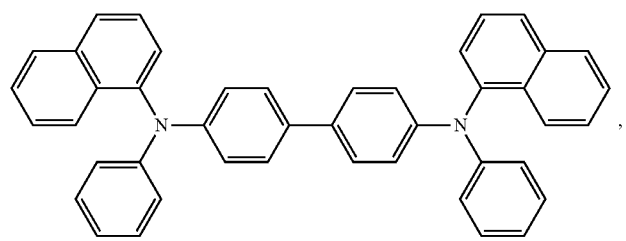
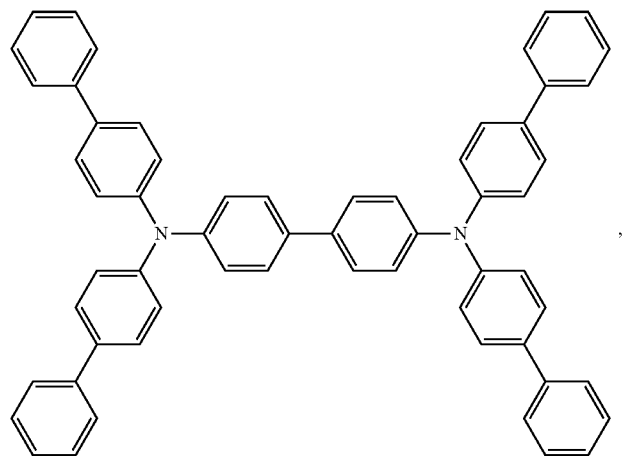

-continued
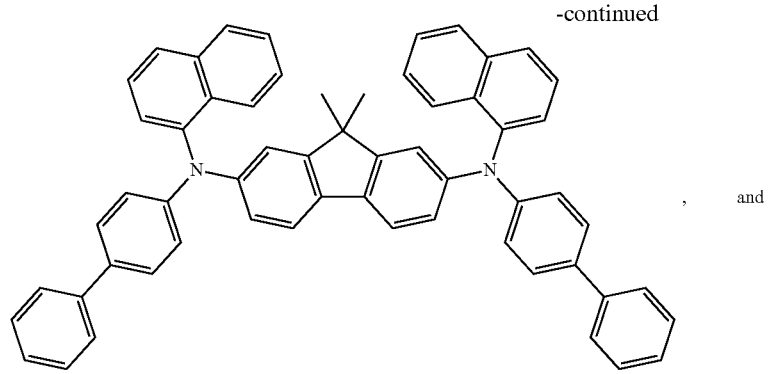
, and
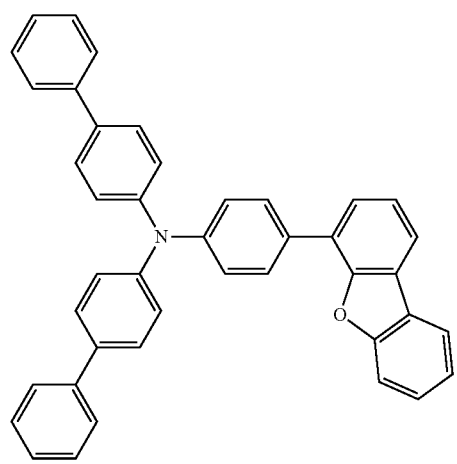
.
11. A compound having a structure selected from the group consisting of:
-continued
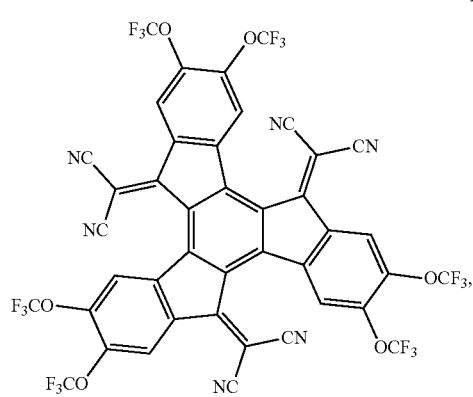
Compound 8
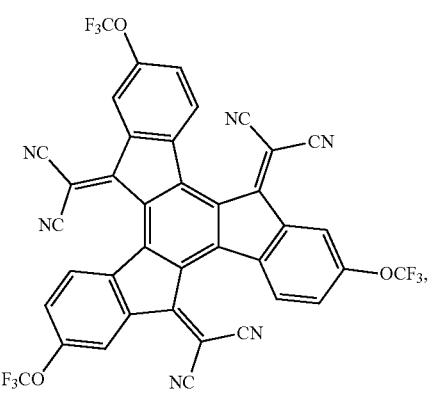
Compound 9

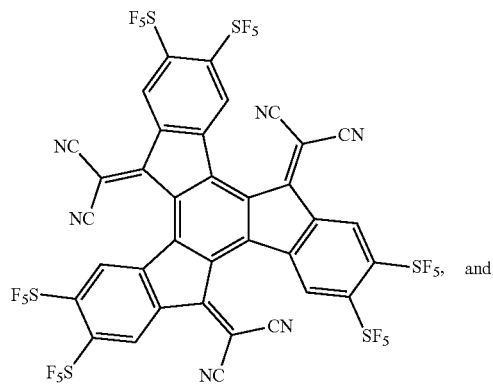
Compound 10
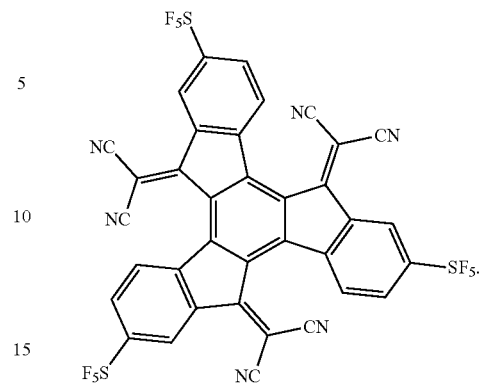
Compound 11
12. The device of claim 1, wherein the device further includes a hole transport layer.
* * * * *